US008852553B2

(12) United States Patent
Cesati et al.

(10) Patent No.: US 8,852,553 B2
(45) Date of Patent: Oct. 7, 2014

(54) N-ALKOXYAMIDE CONJUGATES AS IMAGING AGENTS

(71) Applicant: Lantheus Medical Imaging, Inc., North Billerica, MA (US)

(72) Inventors: Richard R. Cesati, Pepperell, MA (US); Thomas D. Harris, Salem, NH (US); Simon P. Robinson, Stow, MA (US); Richard J. Looby, Reading, MA (US); Edward H. Cheesman, Lunenburg, MA (US); Padmaja Yalamanchili, Princeton, NJ (US); David S. Casebier, Carlisle, MA (US)

(73) Assignee: Lantheus Medical Imaging, Inc., North Billerica, MA (US)

(*) Notice: Subject to any disclaimer, the term of this patent is extended or adjusted under 35 U.S.C. 154(b) by 102 days.

(21) Appl. No.: 13/723,333

(22) Filed: Dec. 21, 2012

(65) Prior Publication Data
US 2013/0315822 A1   Nov. 28, 2013

Related U.S. Application Data

(63) Continuation of application No. 12/350,628, filed on Jan. 8, 2009, now Pat. No. 8,361,438.

(60) Provisional application No. 61/019,627, filed on Jan. 8, 2008.

(51) Int. Cl.
| A61K 49/00 | (2006.01) |
| A61K 49/04 | (2006.01) |
| A61K 51/04 | (2006.01) |
| C07C 271/22 | (2006.01) |
| C07D 403/12 | (2006.01) |
| C07C 259/14 | (2006.01) |
| C07D 257/02 | (2006.01) |
| C07D 213/56 | (2006.01) |
| C07D 209/20 | (2006.01) |
| A61K 49/10 | (2006.01) |

(52) U.S. Cl.
CPC .............. *A61K 49/106* (2013.01); *A61K 51/04* (2013.01); *C07C 271/22* (2013.01); *C07D 403/12* (2013.01); *C07C 259/14* (2013.01); *C07D 257/02* (2013.01); *C07D 213/56* (2013.01); *C07D 209/20* (2013.01); *A61K 49/103* (2013.01)
USPC ........... 424/1.65; 424/9.1; 424/9.36; 424/9.4; 424/9.44; 540/465; 540/474

(58) Field of Classification Search
USPC .............. 424/1.65, 9.1, 9.3, 9.361, 9.4, 9.44; 540/465, 474
See application file for complete search history.

(56) References Cited

U.S. PATENT DOCUMENTS

| 4,859,777 | A  | 8/1989  | Toner |
| 5,064,956 | A  | 11/1991 | Kruper, Jr. |
| 5,087,440 | A  | 2/1992  | Cacheris et al. |
| 5,089,043 | A  | 2/1992  | Hayase et al. |
| 5,155,215 | A  | 10/1992 | Ranney |
| 5,274,129 | A  | 12/1993 | Natale et al. |
| 5,362,475 | A  | 11/1994 | Gries et al. |
| 5,869,651 | A  | 2/1999  | Himmelsbach et al. |
| 5,874,573 | A  | 2/1999  | Winchell et al. |
| 6,461,587 | B1 | 10/2002 | Platzek et al. |
| 6,656,448 | B1 | 12/2003 | Carpenter, Jr. et al. |
| 6,676,929 | B2 | 1/2004  | McMurry et al. |
| 6,869,590 | B2 | 3/2005  | Edwards et al. |
| 6,974,567 | B2 | 12/2005 | Edwards et al. |
| 7,060,250 | B2 | 6/2006  | McMurry et al. |
| 8,361,438 | B2 | 1/2013  | Cesati, III et al. |
| 2002/0002152 | A1 | 1/2002 | Craig et al. |
| 2005/0025702 | A1 | 2/2005 | Decicco et al. |
| 2005/0106100 | A1 | 5/2005 | Harris et al. |
| 2005/0287074 | A1 | 12/2005 | Carpenter, Jr. et al. |
| 2006/0155120 | A1 | 7/2006 | Amedio et al. |
| 2007/0014721 | A1 | 1/2007 | Harris et al. |
| 2007/0142417 | A1 | 6/2007 | Haddad et al. |
| 2007/0189969 | A1 | 8/2007 | Schirmer et al. |
| 2012/0328514 | A1 | 12/2012 | Cesati, III et al. |

FOREIGN PATENT DOCUMENTS

| CN | 1189105 A   | 7/1998 |
| CN | 101970015 A | 2/2011 |
| EP | 0 233 607 A2 | 8/1987 |
| EP | 0 337 348 A2 | 10/1989 |

(Continued)

OTHER PUBLICATIONS

Knobler et al., Reaction of N-carboxy-α-amino-acid anhydrides with hydrochlorides of hydroxylamine, O-alkylhydroxylamines, and amines; syntheses of amino-hydroxamic acids, amido-oxy-peptides, and α-amino-acid amides. J Chem Soc. 1964, pp. 3941-3951.

(Continued)

*Primary Examiner* — Michael G Hartley
*Assistant Examiner* — Jagadishwar Samala
(74) *Attorney, Agent, or Firm* — Wolf, Greenfield & Sacks, P.C.

(57) ABSTRACT

The present disclosure is directed to compounds, diagnostic agents, and related methods. In some cases, methods for treating patients are provided. More specifically, the disclosure provides compounds, diagnostic agents, and kits for detecting and/or imaging and/or monitoring elastin rich tissues. In addition, the disclosure provides methods of detecting and/or imaging and/or monitoring the presence of coronary plaque, carotid plaque, iliac/femoral plaque, aortic plaque, renal artery plaque, plaque of any arterial vessel, aneurism, vasculitis, other diseases of the arterial wall, and/or damage or structural changes in ligaments, uterus, lungs or skin, as indicated by changes in total vessel wall area, internal lumen size, and exterior arterial perimeter.

21 Claims, 1 Drawing Sheet

(56) References Cited

FOREIGN PATENT DOCUMENTS

| | | |
|---|---|---|
| JP | S51-22885 A | 2/1976 |
| JP | 52-015824 A | 2/1977 |
| JP | 04-091070 A | 3/1992 |
| JP | 08-231500 A | 9/1996 |
| JP | 10512241 T2 | 11/1998 |
| WO | WO 96/20918 A1 | 7/1996 |
| WO | WO 01/60416 A | 8/2001 |
| WO | WO 02/074981 A2 | 9/2002 |
| WO | WO 03/011115 A2 | 2/2003 |
| WO | WO 2005/001415 A2 | 1/2005 |
| WO | WO 2005/020973 A2 | 3/2005 |
| WO | WO 2009/089022 A1 | 7/2009 |
| WO | WO 2011/000532 A2 | 4/2011 |

OTHER PUBLICATIONS

European Examination Report for EP EP 09700768.6 mailed Nov. 12, 2012.
International Search Report and Written Opinion for PCT/US2009/000096, mailed Apr. 22, 2009.
International Preliminary Report on Patentability for PCT/US2009/000096, mailed Jul. 22, 2010.
International Search Report and Written Opinion for PCT/US2010/001926, mailed Feb. 24, 2011.
International Preliminary Report on Patentability for PCT/US2010/001926, mailed Jan. 19, 2012.
Andrews et al., Reaction of aziridinium ions with organometallic reagents: optimization of the key step of ecopipam synthesis. Tetrahedron Lett. Aug. 25, 2002;43(35):6121-5.
Anelli et al., L-Glutamic acid and L-lysine as useful building blocks for the preparation of bifunctionalDTPA-like ligands. Bioconjug Chem. Jan.-Feb. 1999;10(1):137-40.
Bousquet et al., Gd-DOTA: characterization of a new paramagnetic complex. Radiology. Mar. 1988;166(3):693-8.
Breichbiel et al., Backbone-substituted DTPA ligands for yttrium-90 radioimmunotherapy. Bioconj Chem. May 1991;2(3):187-94.
Carpino, O-Acylhydroxylamines. II. O-Mesitylenesulfonyl-, O-p-Toluenesulfonyl- and O-Mesitoylhydroxylamine. J Am Chem Soc. 1960;82(12):3133-5.
Chang et al., Synthesis of optically active α-aminobenzolactam via an oxidative-cyclization reaction. Tetrahedron: Assymetry. 2003;14:2081-5.
Charreyre et al., Synthesis of a hexyl methacrylate-terminated disaccharide monomer and study of its radically initiated homo- and copolymerization with styrene. Mak Chem. 1993;194(1):117-35.
Cheung et al., N-Methylamino acids in peptide synthesis. V. The synthesis of N-tert-butyloxycarbonyl, N-methylamino acids by N-methylation. Can J Chem. 1977;55(5):906-10.
Cho et al., NMR studies on turn mimetic analogs derived from melanocyte-stimulating hormones. J Biochem Mol Biol. Nov. 30, 2003;36(6):552-7.
Degrado et al., Polymer-bound oxime esters as supports for solid-phase peptide synthesis. The preparation of protected peptide fragments. J Org Chem. 1980;45(7):1295-1300.
Deshpande et al., Yttrium-90-Labeled Monoclonal Antibody for Therapy: Labeling by a New Macrocyclic Bifunctional Chelating Agent. J Nucl Med. 1990;43:473-9.
Freidinger et al., Synthesis of 9-fluorenylmethyloxycarbonyl-protected N-alkyl amino acids by reduction of oxazolidinones. J Org Chem. 1983;48(1):77-81.
Groves et al., Catalytic unfolding and proteolysis of cytochrome C induced by synthetic binding agents. J Am Chem Soc. Oct. 13, 2004;126(40):12833-42.
Imamura et al., Structure-activity relationships of trans-3,5-disubstituted pyrrolidinylthio-1beta-methylcarbapenems. Part 1: J-111,347 and related compounds. Bioorg Med Chem Lett. Jan. 17, 2000;10(2):109-13.
Kang et al., Synthesis and antibacterial activity of new carbapenems containing isoxazole moiety. Bioorg Med Chem Lett. 2000;10(2000):95-99.
Krause, O-Mesitylenesulfonylhydroxylamine. Synthesis. 1972;3:140.
Magerstädt et al., Gd(DOTA): An alternative to Gd(DTPA) as a T1,2 relaxation agent for NMR imaging or spectroscopy. Magn Reson Med. Oct. 1986;3(5):808-12.
Merrifield, Solid phase peptide synthesis. I. The synthesis of a tetrapeptide J Am Chem Soc. 1963;85(14): 2149-54.
Rozsondai et al., The molecular structures of divinyl sulfide and divinyl sulfoxide in the gas phase from electron diffraction. J Chem Soc Perkins Trans. 1992;1:1175-80.
Runge et al., MR imaging of rat brain glioma: Gd-DTPA versus Gd-DOTA. Radiology. Mar. 1988; 166(3): 835-8.
Sheppard et al., 3-Amino-2-hydroxyamides and related compounds as inhibitors of methionine aminopeptidase-2. Bioorg Med Chem Lett. Feb. 23, 2004;14(4):865-8.
Suits et al., Synthesis and chemistry of an unusual bridgehead alkene. J Org Chem. 1983;48(25):5120-3.
Wei et al., Structure-activity relationships of novel endomorphin-2 analogues with N-O turns induced by alpha-aminoxy acids. Bioorg Med Chem Lett. Jun. 15, 2005;15(12):2986-9.
Williams et al., Synthesis of enantiomerically pure diethylenetriaminepentaacetic acid analogs. L-Phenylalanine as the educt for substitution at the central acetic acid. J Org Chem. 1993;58(5):1151-8.
Yang et al., A new strategy to induce gamma-turns: peptides composed of alternating alpha-aminoxy acids and alpha-amino acids. J Am Chem Soc. Oct. 29, 2003;125(43):13018-9.
Examination Report for European Application No. EP09700768.6 mailed Mar. 18, 2014.
Barlaam et al., New alpha-substituted succinate-based hydroxamic acids as TNFalpha convertase inhibitors. J Med Chem. Nov. 18, 1999;42(23):4890-908.
Barlaam et al., New hydroxylamines for the synthesis of hydroxamic acids. Tetrahedron Letters. Oct. 22, 1998; 39(43):7865-8.
Chen et al., Synthesis of a Cyclen-Functionalized α-Amino Acid and its Incorporation into Peptide Sequence. Synthesis. Jan. 1, 2005; 2005(6): 888-92.
Clarkson et al., Experimental assessment of the efficacy of sensitised emission in water from a europium ion, following intramolecular excitation by a phenanthridinyl group. New Journal of Chemistry. Jan. 1, 2000; 24(6):377-86.
Flipo et al., A library of novel hydroxamic acids targeting the metalloprotease family: design, parallel synthesis and screening. Bioorg Med Chem. Jan. 1, 2007;15(1):63-76. Epub Oct. 12, 2006.
Knör et al., Synthesis of novel 1,4,7,10-tetraazacyclodecane-1,4,7,10-tetraacetic acid (DOTA) derivatives for chemoselective attachment to unprotected polyfunctionalized compounds. Chemistry. 2007;13(21):6082-90.
Pirrung et al., High-throughput catch-and-release synthesis of oxazoline hydroxamates. Structure-activity relationships in novel inhibitors of *Escherichia coli* LpxC: in vitro enzyme inhibition and antibacterial properties. J Am Chem Soc. Feb. 12, 2003;125(6):1575-86.
Ritter et al., Chiral NADH model systems functionalized with Zn(II)-cyclen as flavin binding site. Tetrahedron. May 30, 2005; 61(22): 5241-51.

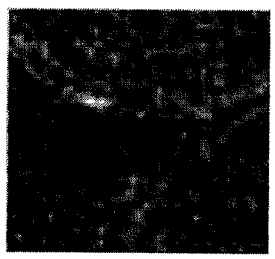  
PRE-INJECTION     10-25 MIN POST-INJECTION     30-50 MIN POST-INJECTION

N-ALKOXYAMIDE CONJUGATES AS IMAGING AGENTS

RELATED APPLICATIONS

This application is a continuation and claims priority to co-pending U.S. application Ser. No. 12/350,628, filed Jan. 8, 2009, which claims the benefit of U.S. Provisional Application Ser. No. 61/019,627, filed Jan. 8, 2008. The entire disclosure of these applications are relied upon and incorporated by reference herein.

FIELD OF THE INVENTION

The present invention relates to compounds and diagnostic agents, and related methods.

BACKGROUND OF THE INVENTION

Cardiovascular diseases are the leading cause of death in the United States, accounting annually for more than one million deaths. Atherosclerosis is the major contributor to coronary heart disease and a primary cause of non-accidental death in Western countries. Considerable effort has been made in defining the etiology and potential treatment of atherosclerosis and its consequences, including myocardial infarction, angina, organ failure, and stroke. Despite this effort, there are many unanswered questions including how and when atherosclerotic lesions become vulnerable and life-threatening, the best point of intervention, and how to detect and monitor the progression of lesions.

In the last two decades, many radiotracers have been developed based on several molecules and cell types involved in atherosclerosis. In general, radiolabeled proteins and platelets have shown some clinical potential as imaging agents of atherosclerosis, but due to poor target/background and target/blood ratios, these agents are not ideal for imaging coronary or even carotid lesions. Radiolabeled peptides, antibody fragments, and metabolic tracers like FDG appear to offer new opportunities for nuclear scintigraphic techniques in the non-invasive imaging of atherothrombosis. However, a non-invasive method to diagnose and monitor various cardiovascular diseases is needed.

SUMMARY OF THE INVENTION

The present invention relates to compounds of Formula (I),

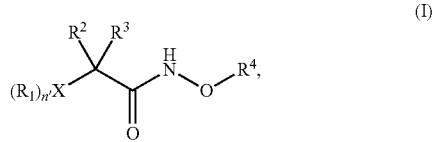

(I)

or a pharmaceutically acceptable salt thereof, wherein:
X is a heteroatom;
$R^1$ is hydrogen, alkyl, alkenyl, arylalkyl, alkylarylalkyl, alkoxyalkyl, heteroalkyl, or heterocyclylalkyl;
$R^2$ and $R^3$ can be the same or different and are hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and
$R^4$ is alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl,
wherein each $R^1$, $R^2$, $R^3$, and $R^4$ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, $-NR^{19}R^{20}$, $-SH$, $-S(Pg)$, $-OH$, $-PR^{19}R^{20}$, $-P(O)R^{21}R^{22}$, $-CO_2H$, =O, halo, trifluoromethyl, cyano, $-CO_2R^{24}$, $-C(=O)R^{24}$, $-C(=O)N(R^{24})_2$, $-CHO$, $-CH_2OR^{24}$, $-OC(=O)R^{24}$, $-OC(=O)OR^{24}$, $-OR^{24}$, $-OC(=O)N(R^{24})_2$, $-NR^{24}C(=O)R^{24}$, $-NR^{24}C(=O)OR^{24}$, $-NR^{24}C(=O)N(R^{24})_2$, $-NR^{24}SO_2N(R^{24})_2$, $-NR^{24}SO_2R^{24}$, $-SO_3H$, $-SO_2R^{24}$, $-SR^{24}$, $-S(=O)R^{24}$, $-SO_2N(R^{24})_2$, $-N(R^{24})_2$, $-NHC(=S)NHR^{24}$, =$NOR^{24}$, $-NO_2$, $-C(=O)NHOR^{24}$, $-C(=O)NHNR^{24}R^{24}$, $-OCH_2CO_2H$, 2-(1-morpholino)ethoxy, or a chelator moiety;

$R^{19}$ and $R^{20}$ are each independently selected from hydrogen, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$.

$R^{21}$ and $R^{22}$ are each independently selected from $-OH$, $C_{1-10}$alkyl substituted with 0-3 $R^{23}$, aryl substituted with 0-3 $R^{23}$, $C_{3-10}$cycloalkyl substituted with 0-3 $R^{23}$ heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;

each $R^{23}$ is independently selected from =O, halo, trifluoromethyl, cyano, $-CO_2R^{24}$, $-C(=O)R^{24}$, $-C(=O)N(R^{24})_2$, $-CHO$, $-CH_2OR^{24}$, $-OC(=O)R^{24}$, $-OC(=O)OR^{24}$, $-OR^{24}$, $-OC(=O)N(R^{24})_2$, $-NR^{24}C(=O)R^{24}$, $-NR^{24}C(=O)OR^{24}$, $-NR^{24}C(=O)N(R^{24})_2$, $-NR^{24}SO_2N(R^{24})_2$, $-NR^{24}SO_2R^{24}$, $-SO_3H$, $-SO_2R^{24}$, $-SR^{24}$, $-S(=O)R^{24}$, $-SO_2N(R^{24})_2$, $-N(R^{24})_2$, $-NHC(=S)NHR^{24}$, =$NOR^{24}$, $-NO_2$, $-C(=O)NHOR^{24}$, $-C(=O)NHNR^{24}R^{24}$, $-OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0-2 $R^{24}$, and heterocyclyl;

each $R^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl;

Pg is a thiol protecting group; and
n' is an integer from 0-4,
wherein the compound comprises at least one chelator moiety.

In some embodiments, X is nitrogen. In some embodiments, X is oxygen. In some embodiments, X is sulfur. In some embodiments, X is phosphorus.

In some embodiments, n' is an integer from 0-3.
In some embodiments, each $R^{24}$ is independently hydrogen, $C_{1-6}$alkyl, phenyl, benzyl, or $C_{1-6}$ alkoxy.

In one set of embodiments,
X is nitrogen;
$R^1$ is hydrogen, alkyl, arylalkyl, or alkylarylalkyl;
$R^2$ and $R^3$ can be the same or different and are hydrogen, alkyl, alkylaryl, aryl, arylalkyl, alkylarylalkyl, or heterocyclylalkyl;
$R^4$ is alkyl, alkylaryl, aryl, arylalkyl, or alkylarylalkyl, wherein at least one of $R^1$, $R^2$, $R^3$, and $R^4$ is substituted with a chelator moiety;

In any of the foregoing embodiments, $R^2$ or $R^3$ can comprise the following structure,

wherein
n is 0-6; and
$R^z$ is selected from alkyl, aryl, cycloalkenyl, cycloalkyl, heteroaryl, and heterocyclyl.

In any of the foregoing embodiments, $R^2$ or $R^3$ can also comprise the following structure,

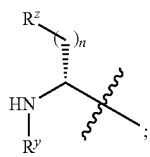

wherein n is 0-6;

$R^y$ is selected from hydrogen, alkenyl, and alkyl; and $R^z$ is selected from alkyl, aryl, cycloalkenyl, cycloalkyl, heteroaryl, and heterocyclyl.

In one set of embodiments, n is 1 or 2;

$R^y$ is hydrogen; and $R^z$ is selected from alkyl, aryl, cycloalkyl, and heteroaryl.

In some embodiments, $R^1$ comprises the at least one chelator moiety. In some embodiments, $R^2$ or $R^3$ comprises the at least one chelator moiety. In some embodiments, $R^4$ comprises the at least one chelator moiety.

In one set of embodiments, the compound has a structure as in Formula (II),

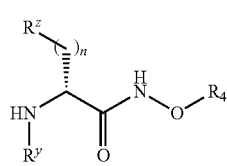

or a pharmaceutically acceptable salt thereof; wherein $R^4$ is alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, substituted with the at least one chelator moiety;

n is 0-6;

$R^Y$ is selected from hydrogen, alkenyl, and alkyl; and $R^z$ is selected from alkyl, aryl, cycloalkenyl, cycloalkyl, heteroaryl, and heterocyclyl.

In another set of embodiments, the compound has a structure as in Formula (III),

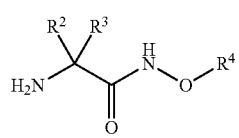

or a pharmaceutically acceptable salt thereof, wherein $R^2$ and $R^3$ can be the same or different and are hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl, and at least one of $R^2$ and $R^3$ is substituted with the at least one chelator moiety; and $R^4$ is alkyl or arylalkyl.

In another set of embodiments, the compound has a structure as in Formula (IV),

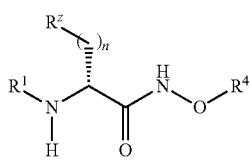

or a pharmaceutically acceptable salt thereof; wherein $R^1$ is alkyl, alkenyl, cycloalkyl, arylalkyl, alkoxyalkyl, heteroalkyl, or heterocyclylalkyl, substituted with the at least one chelator moiety;

n is 0-6;

$R^z$ is selected from alkyl, aryl, cycloalkenyl, cycloalkyl, heteroaryl, and heterocyclyl; and $R^4$ is alkyl or arylalkyl.

In any of the foregoing embodiments, the at least one chelator moiety has the structure,

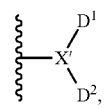

wherein X' is a heteroatom; and $D^1$ and $D^2$ can be the same or different and are hydrogen or a chelator moiety. In some embodiments, the at least one chelator moiety has the structure,

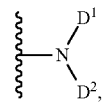

wherein $D^1$ and $D^2$ can be the same or different and are hydrogen or a chelator moiety. In some embodiments, one of $D^1$ and $D^2$ is a hydrogen and the other is a chelator moiety. The chelator moiety may be selected from

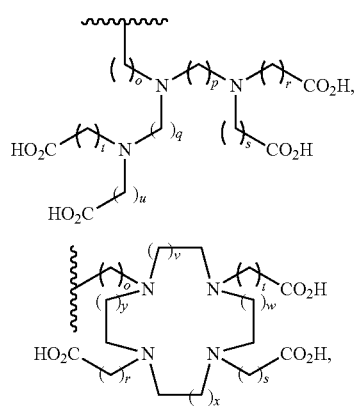

5
-continued

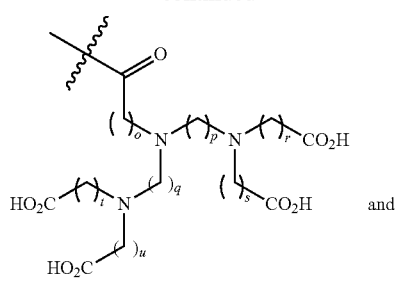

and

6
-continued

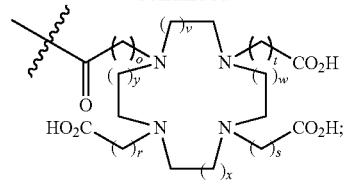

wherein o, p, q, r, s, t, and u are each independently 1-6; and v, w, x, and y are each independently 1-3. In some embodiments, o, r, s, t, and u are each 1; and p and q are each 2. In some embodiments, o, r, s, t, v, w, x and y are each 1.

In one embodiment, the compound has the structure,

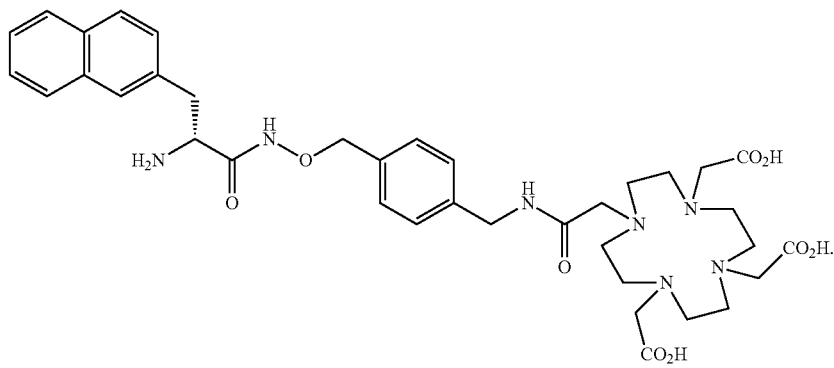 [SMILES: N[C@H](Cc1ccc2ccccc2c1)C(=O)NOCc1ccc(CNC(=O)CN2CCN(CC(=O)O)CCN(CC(=O)O)CCN(CC(=O)O)CC2)cc1]

In another embodiment, the compound has the structure,

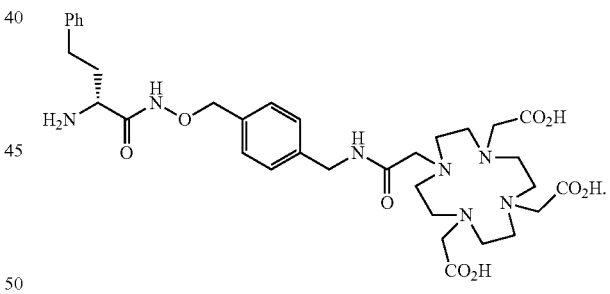

In another embodiment, the compound has the structure,

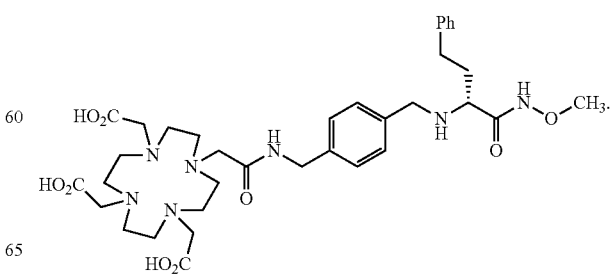

In another embodiment, the compound has the structure,

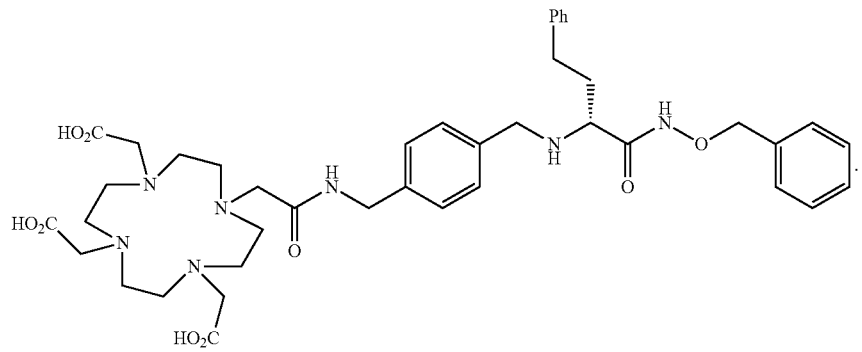 [SMILES: O=C(O)CN1CCN(CC(=O)O)CCN(CC(=O)NCc2ccc(CN[C@H](CCc3ccccc3)C(=O)NOCc3ccccc3)cc2)CCN(CC(=O)O)CC1]

In another embodiment, the compound has the structure,

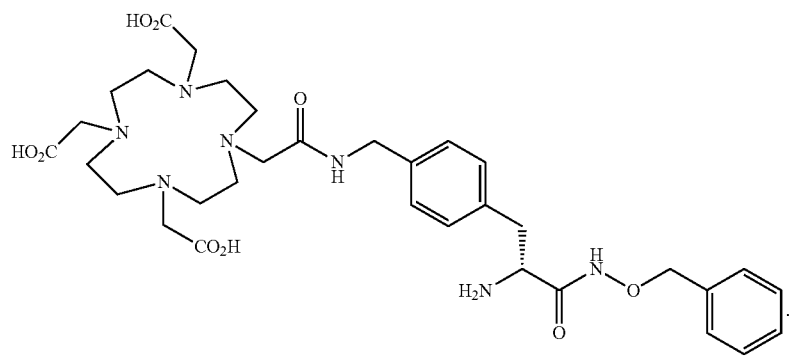 [SMILES: N[C@H](Cc1ccc(CNC(=O)CN2CCN(CC(=O)O)CCN(CC(=O)O)CCN(CC(=O)O)CC2)cc1)C(=O)NOCc1ccccc1]

In another embodiment, the compound has the structure,

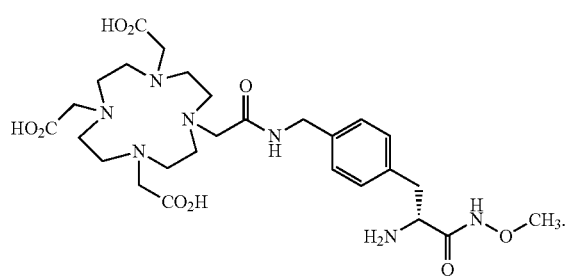 [SMILES: CONC(=O)[C@H](N)Cc1ccc(CNC(=O)CN2CCN(CC(=O)O)CCN(CC(=O)O)CCN(CC(=O)O)CC2)cc1]

In one aspect of the present disclosure is provided a compound of Formula (I-A),

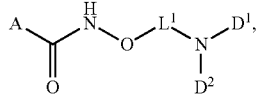

(I-A)

or a pharmaceutically acceptable salt thereof; wherein

A is a D-amino acid residue or a peptide consisting of a D-amino acid residue and a second D-amino acid;

$D^1$ and $D^2$ are independently selected from hydrogen, a chelator moiety, and an imaging moiety; and $L^1$ is a linker; or $L^1$ and $D^2$, together with the nitrogen atom to which they are attached, form a five- to seven-membered ring.

In a first embodiment of the first aspect $L^1$ is a linker selected from alkenylene, alkylarylalkylene, alkylene, arylalkylene, heteroalkylene, and heterocyclylene. In a second embodiment of the first aspect $L^1$ is alkylene. In a third embodiment of the first aspect $L^1$ is arylalkylene. In a fourth embodiment of the first aspect $L^1$ is alkylarylalkylene.

In a fifth embodiment of the first aspect A is a D-amino acid residue. In a sixth embodiment of the first aspect A is

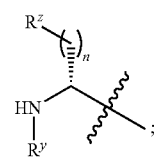

wherein n is 0-6;

$R^y$ is selected from hydrogen, alkenyl, and alkyl; and $R^z$ is selected from alkyl, aryl, cycloalkenyl, cycloalkyl, heteroaryl, and heterocyclyl. In a seventh embodiment of the first aspect n is 1 or 2; $R^y$ is hydrogen; and $R^z$ is selected from alkyl, aryl, cycloalkyl, and heteroaryl.

In an eighth embodiment of the first aspect the present disclosure provides a compound wherein one of $D^1$ and $D^2$ is a hydrogen and the other is a chelator moiety. In a ninth embodiment of the first aspect one of $D^1$ and $D^2$ is hydrogen and the other is a chelator moiety selected from

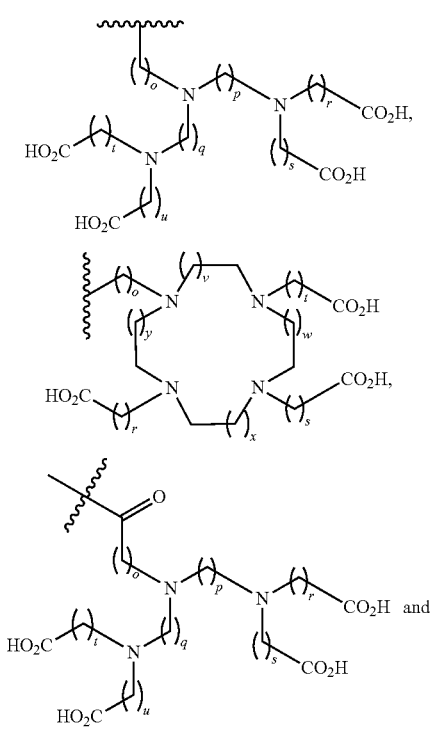

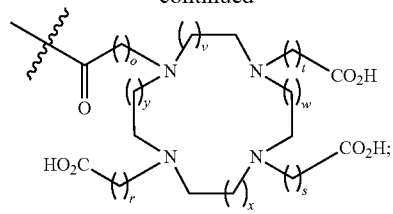

-continued wherein
o, p, q, r, s, t, and u are each independently 1-6; and
v, w, x, and y are each independently 1-3.

In a tenth embodiment o, r, s, t, and u are each 1; and p and q are each 2.

In an eleventh embodiment o, r, s, t, v, w, x and y are each 1.

The present invention also provides diagnostic agents comprising a compound described in any of the foregoing aspects and embodiments; and an imaging agent bound to the at least one chelator moiety. In some embodiments, the imaging agent is an echogenic substance, an optical reporter, a boron neutron absorber, a paramagnetic metal ion, a ferromagnetic metal, a gamma-emitting radioisotope, a positron-emitting radioisotope, or an x-ray absorber. In one set of embodiments, the imaging agent is a paramagnetic metal ion. In a particular embodiment, the paramagnetic metal ion is Gd(III). In another set of embodiments, the imaging agent is a gamma-emitting radioisotope or positron-emitting radioisotope selected from $^{111}$In, $^{62}$Cu, $^{64}$Cu, $^{67}$Ga, $^{68}$Ga, and $^{153}$Gd.

In one embodiment, the diagnostic agent has the structure,

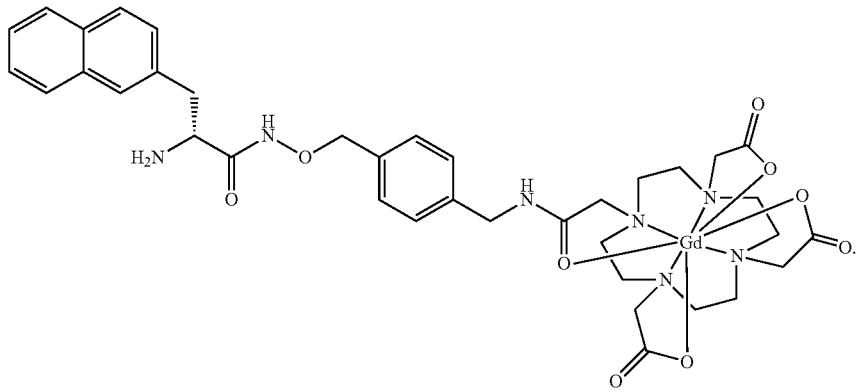

In another embodiment, the diagnostic agent has the structure,

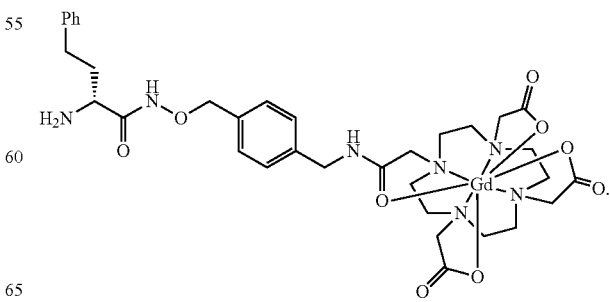

In another embodiment, the diagnostic agent has the structure,
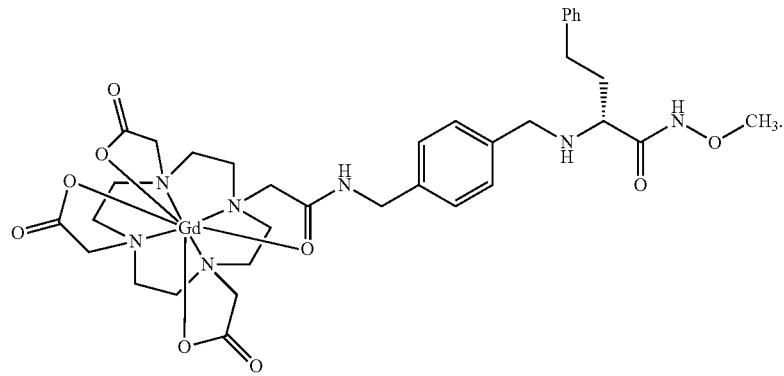
In another embodiment, the diagnostic agent has the structure,
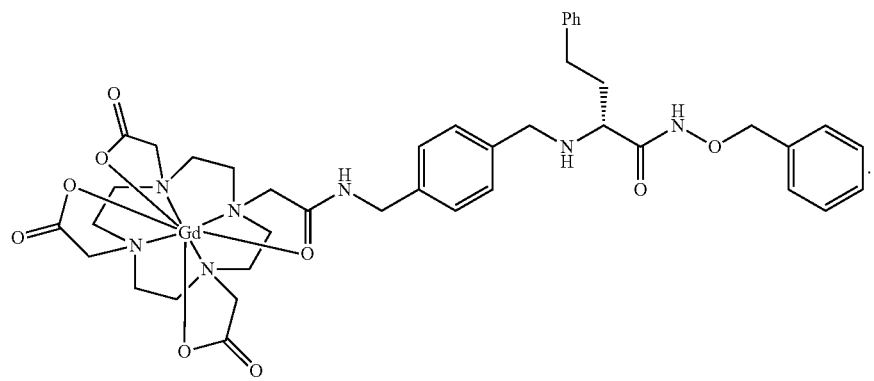
In another embodiment, the diagnostic agent has the structure,
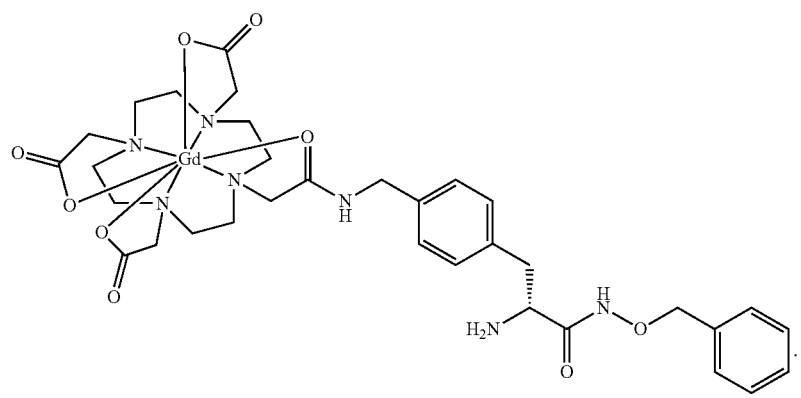

In another embodiment, the diagnostic agent has the structure,

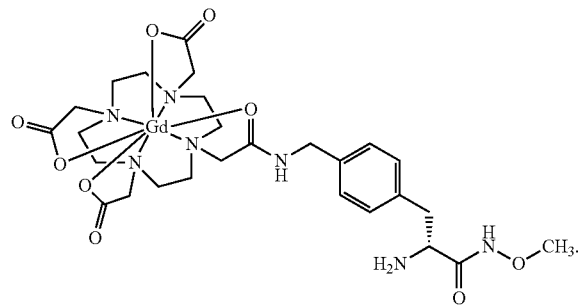

In a second aspect the present disclosure provides a diagnostic agent comprising:

a. a compound of Formula (I-B)

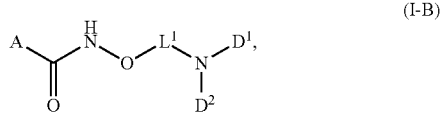

(I-B)

or a pharmaceutically acceptable salt thereof; wherein

A is a D-amino acid residue or a peptide consisting of a D-amino acid residue and a second D-amino acid;

$D^1$ and $D^2$ are independently selected from hydrogen and a chelator moiety;

$L^1$ is a linker; or $L^1$ and $D^2$, together with the nitrogen atom to which they are attached, form a five- to seven-membered ring; and b. an imaging agent bound to the diagnostic agent.

In some embodiments, the imaging agent is bound to the diagnostic agent via a chelator moiety.

In a first embodiment of the second aspect the imaging agent is an echogenic substance, an optical reporter, a boron neutron absorber, a paramagnetic metal ion, a ferromagnetic metal, a gamma-emitting radioisotope, a positron-emitting radioisotope, or an x-ray absorber. In a second embodiment of the second aspect the imaging agent is a paramagnetic metal ion. In a third embodiment of the second aspect the paramagnetic metal ion is Gd(III).

In a fourth embodiment of the second aspect the imaging agent is a gamma-emitting radioisotope or positron-emitting radioisotope selected from $^{111}$In, $^{62}$Cu, $^{64}$Cu, $^{67}$Ga, $^{68}$Ga, and $^{153}$Gd.

In a third aspect the present disclosure provides a compound selected from

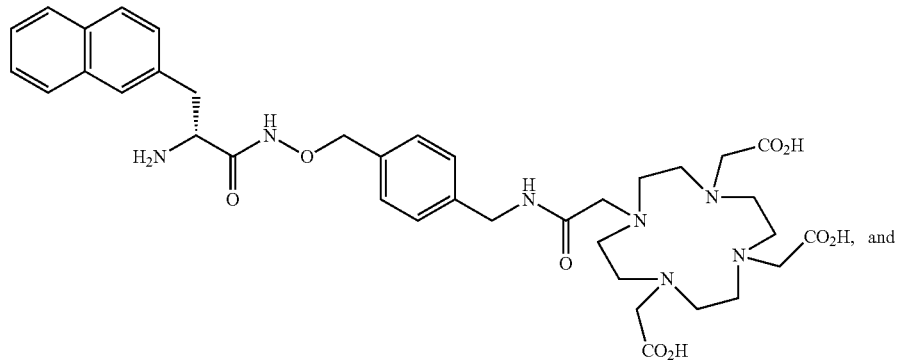

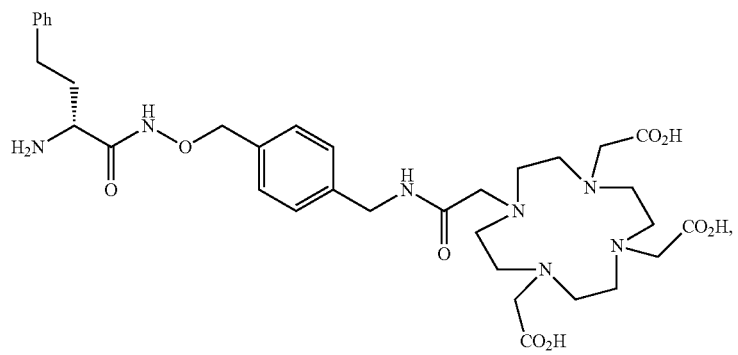

or a pharmaceutically acceptable salt thereof.

In a fourth aspect the present disclosure provides a compound selected from

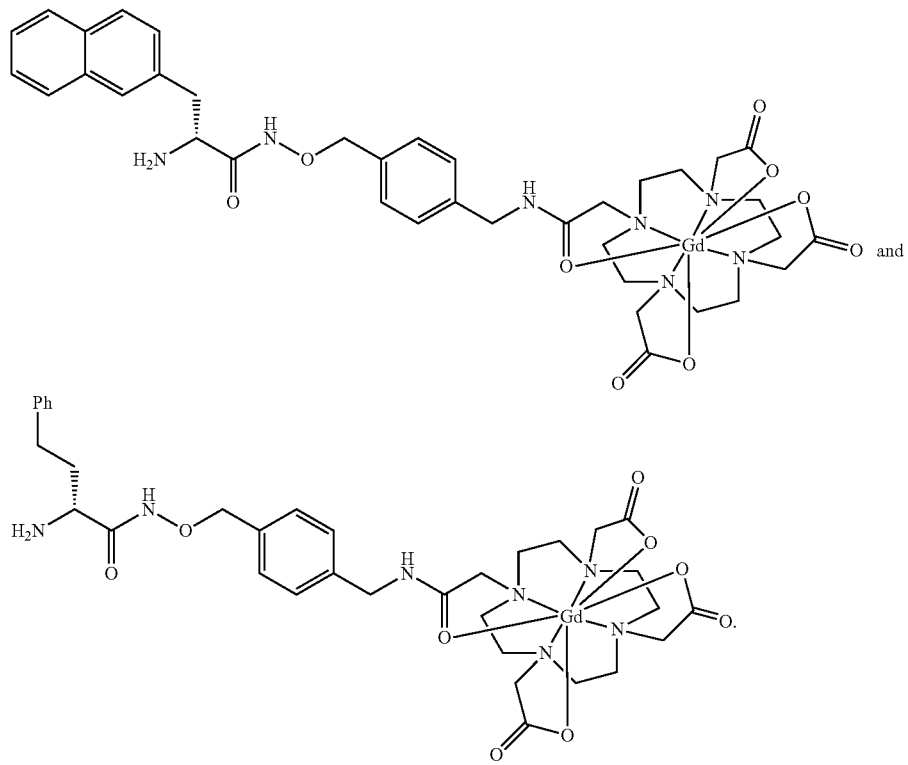

In a fifth aspect the present disclosure provides a method of detecting, imaging, and/or monitoring elastin rich tissues in a patient comprising the steps of:
 a. administering to the patient a diagnostic agent comprising:
  1. a compound of Formula (I-B)

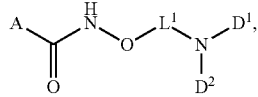

(I-B)

or a pharmaceutically acceptable salt thereof; wherein
 A is a D-amino acid residue or a peptide consisting of a D-amino acid residue and a second D-amino acid;
 $D^1$ and $D^2$ are independently selected from hydrogen and a chelator moiety;
 $L^1$ is a linker; or
 $L^1$ and $D^2$, together with the nitrogen atom to which they are attached, form a five- to seven-membered ring; and
  2. an imaging agent; and
 b. acquiring an image of a site of concentration of the compound in the patient by a diagnostic imaging technique.
In a first embodiment of the fifth aspect the elastin rich tissues are the arterial wall, uterus, lung, skin, and/or ligaments.
In a sixth aspect the present disclosure provides a method of detecting, imaging, and/or monitoring the presence of coronary plaque, carotid plaque, iliac/femoral plaque, aortic plaque, renal artery plaque, plaque of any arterial vessel, aneurism, vasculitis, other diseases of the arterial wall, and/or damage or structural changes in ligaments, uterus, lungs or skin in a patient comprising the steps of:
 a. administering to the patient a diagnostic agent comprising:
  1. a compound of Formula (I-B)

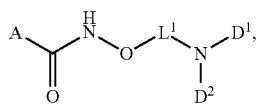

(I-B)

or a pharmaceutically acceptable salt thereof; wherein
 A is a D-amino acid residue or a peptide consisting of a D-amino acid residue and a second D-amino acid;
 $D^1$ and $D^2$ are independently selected from hydrogen and a chelator moiety;
 $L^1$ is a linker; or
 $L^1$ and $D^2$, together with the nitrogen atom to which they are attached, form a five- to seven-membered ring; and
  2. an imaging agent; and
 b. acquiring an image of a site of concentration of the compound in the patient by a diagnostic imaging technique.
The present invention also provides compounds of Formula (V),

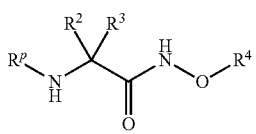

(V)

or a pharmaceutically acceptable salt thereof; wherein
R$^P$ is a hydrogen or an α-amino protecting group;
R$^2$ and R$^3$ can be the same or different and are hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and
R$^4$ is hydrogen, alkyl, alkylaryl, or alkylarylalkyl,
wherein each R$^2$, R$^3$, and R$^4$ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —NR$^{19}$R$^{20}$, —SH, —S(Pg), —OH, —PR$^{19}$R$^{20}$, —P(O)R$^{21}$R$^{22}$, —CO$_2$H, =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, NO$_2$, —C(=O)NHOR$^{24}$, —C(=O)NHNR$^{24}$R$^{24}$, —OCH$_2$CO$_2$H, 2-(1-morpholino) ethoxy, or a chelator moiety;
R$^{19}$ and R$^{20}$ are each independently selected from hydrogen, C$_{1-10}$alkyl substituted with 0-3 R$^{23}$, aryl substituted with 0-3 R$^{23}$, C$_{3-10}$cycloalkyl substituted with 0-3 R$^{23}$ heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$.
R$^{21}$ and R$^{22}$ are each independently selected from —OH, C$_{1-10}$alkyl substituted with 0-3 R$^{23}$, aryl substituted with 0-3 R$^{23}$, C$_{3-10}$cycloalkyl substituted with 0-3 R$^{23}$, heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$ each R$^{23}$ is independently selected from =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, —NO$_2$, —C(=O)NHOR$^{24}$, —C(=O)NHNR$^{24}$R$^{24}$, —OCH$_2$CO$_2$H, 2-(1-morpholino) ethoxy, C$_{1-5}$alkyl, C$_{2-4}$alkenyl, C$_{3-6}$cycloalkyl, C$_{3-6}$cycloalkylmethyl, C$_{2-6}$alkoxyalkyl, aryl substituted with 0-2 R$^{24}$, and heterocyclyl;
each R$^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and
Pg is a thiol protecting group.
In some embodiments, each R$^{24}$ is independently hydrogen, C$_{1-6}$alkyl, phenyl, benzyl, or C$_{1-6}$alkoxy.
In some embodiments, R$^P$ is hydrogen, Boc, or Fmoc; and R$^4$ is hydrogen, alkyl, or alkylarylalkyl, substituted with an amino group. For example, R$^4$ can be

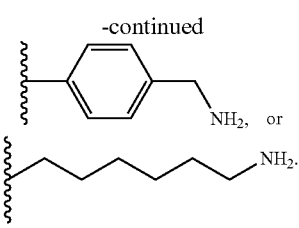

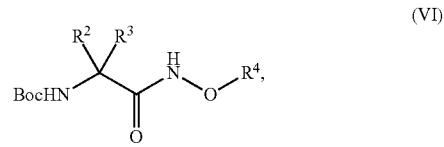

In one set of embodiments, the compound has a structure as in Formula (VI),

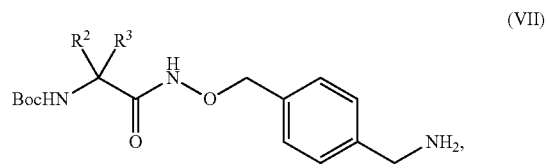

or a pharmaceutically acceptable salt thereof; wherein R$^2$, R$^3$, and R$^4$ are defined herein.

In another set of embodiments, the compound has a structure as in Formula (VII),

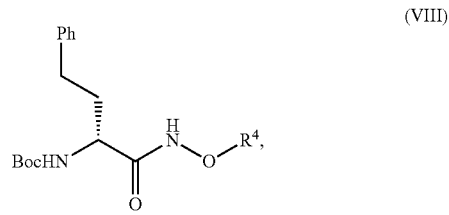

or a pharmaceutically acceptable salt thereof; wherein R$^2$ and R$^3$ are defined herein.

In another set of embodiments, the compound has a structure as in Formula (VIII)

(VIII)

or a pharmaceutically acceptable salt thereof; wherein R$^4$ is defined herein.

In one embodiment, the compound has the structure,

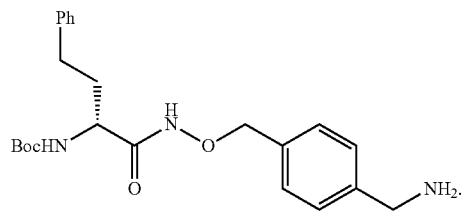 [SMILES: CC(C)(C)OC(=O)N[C@H](CCc1ccccc1)C(=O)NOCc1ccc(CN)cc1]

In another embodiment, the compound has the structure,

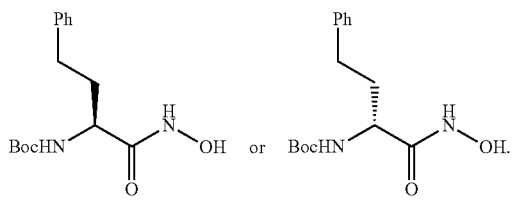 [SMILES: CC(C)(C)OC(=O)N[C@@H](CCc1ccccc1)C(=O)NO ; "or" ; CC(C)(C)OC(=O)N[C@H](CCc1ccccc1)C(=O)NO]

In any of the forgoing aspects and embodiments, an alkyl group may be $C_{1-20}$alkyl, $C_{1-10}$alkyl, $C_{1-6}$alkyl, or $C_{1-5}$alkyl; a cycloalkyl group may be $C_{1-16}$cycloalkyl, $C_{3-14}$cycloalkyl, $C_{3-10}$cycloalkyl, or $C_{3-6}$cycloalkyl; an alkylaryl group may be $C_{1-10}$alkyl-$C_{6-10}$aryl; an alkenyl group may be $C_{2-4}$alkenyl; an aryl group may be $C_{6-10}$ aryl; an arylalkyl group may be $C_{6-10}$aryl-$C_{1-10}$alkyl; an alkoxy group may be $C_{1-6}$alkoxy; an alkoxyalkyl group may be $C_{2-6}$alkoxyalkyl; a heterocyclyl group may be a five-, six-, or seven-membered ring; and a heterocyclylalkyl group may be a heterocyclyl-$C_{1-10}$alkyl.

In any of the forgoing aspects and embodiments, the pharmaceutically acceptable salt may be any salt listed on pages 27-28 of the disclosure, or otherwise disclosed herein.

In any of the forgoing aspects and embodiments, the diagnostic agent may be provided in the absence of a counterion (e.g., as a free base).

The present invention also provides methods for synthesizing any of the foregoing compounds according to the methods described herein. In some embodiments, the method may comprise reacting a compound with an imaging agent to form a diagnostic agent. In another embodiment, the method may comprise reacting an intermediate molecule to produce a compound of the invention. In some embodiments, the method may further comprise isolating and/or purifying the compound and/or diagnostic agent. The method may also comprise characterization of the compound and/or diagnostic agent.

The present invention also provides methods of treating a patient. The method may comprise the steps of administering to the patient a diagnostic agent as in any foregoing diagnostic agent embodiments; and acquiring an image of a site of concentration of the diagnostic agent in the patient by a diagnostic imaging technique. In some embodiments, the treating may comprise detecting, imaging, and/or monitoring elastin-rich tissues in a patient. The elastin-rich tissues may be located within the arterial wall, uterus, lung, skin, and/or ligaments. In some embodiments, the treating may comprise detecting, imaging, and/or monitoring the presence and/or amount of coronary plaque, carotid plaque, iliac/femoral plaque, aortic plaque, renal artery plaque, plaque of any arterial vessel, aneurism, vasculitis, other diseases of the arterial wall, and/or damage or structural changes in ligaments, uterus, lungs or skin in a patient.

Other aspects of the invention may include suitable combinations of embodiments and aspects disclosed herein.

BRIEF DESCRIPTION OF THE DRAWINGS

FIG. 1 shows transaxial MR images of rabbit abdominal aorta using an imaging agent described herein.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present disclosure is directed to compounds, diagnostic agents, and related methods. In some embodiments, methods for synthesizing compounds and/or diagnostic agents are provided. In some embodiments, methods for treating a patient are provided. For example, compounds, diagnostic agents, compositions, and kits for detecting and/or imaging and/or monitoring a pathological disorder associated with coronary plaque, carotid plaque, iliac/femoral plaque, aortic plaque, renal artery plaque, plaque of the arterial vessel, aneurism, vasculitis, other diseases of the arterial wall, and/or damage or structural changes in ligaments, uterus, lungs or skin, are provided. In addition, the disclosure provides methods of detecting and/or imaging and/or monitoring changes in the arterial wall, including expansive and constrictive remodeling, total vessel wall area, internal lumen size, and exterior arterial perimeter. Other aspects and embodiments may be found in the description provided herein.

Unless otherwise specifically noted herein, the terms set forth below will have the following definitions.

In some instances, the number of carbon atoms in any particular group is denoted before the recitation of the group. For example, the term "$C_{6-10}$ aryl" denotes an aryl group containing from six to ten carbon atoms, and the term "$C_{6-10}$ aryl-$C_{1-10}$ alkyl," refers to an aryl group of six to ten carbon atoms attached to the parent molecular moiety through an alkyl group of one to ten carbon atoms. Where these designations exist they supersede all other definitions contained herein.

As used herein, the singular forms "a," "an," and "the" include plural reference unless the context clearly dictates otherwise.

The term "alkenyl," as used herein, refers to a straight or branched chain hydrocarbon of two to fourteen carbon atoms containing at least one carbon-carbon double bond.

The term "alkenylene," as used herein, refers to a divalent group derived from a straight or branched chain hydrocarbon of two to fourteen carbon atoms containing at least one carbon-carbon double bond.

The term "alkoxy," as used herein refers to an alkyl group attached to the parent molecular moiety through an oxygen atom.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon.

The term "alkylaryl," as used herein, refers to an alkyl group attached to the parent molecular moiety through an aryl group.

The term "alkylcarbonyl," as used herein, refers to an alkyl group attached to the parent molecular moiety through a carbonyl group.

The term "alkylene," as used herein, refers to a divalent group derived from a straight or branched chain saturated hydrocarbon of one to fourteen carbon atoms.

As used herein, the phrase "amino acid residue" means a moiety derived from a naturally-occurring or synthetic organic compound containing an amino group (—$NH_2$), a carboxylic acid group (—COOH), and any of various side groups, especially any of the 20 compounds that have the basic formula $NH_2CHRCOOH$, and that link together by peptide bonds to form proteins or that function as chemical messengers and as intermediates in metabolism. For example, in compound X

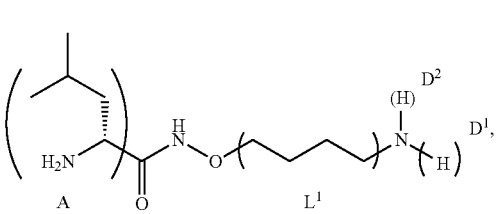

the portion of the molecule denoted as "A" is a residue of the amino acid D-leucine.

The term "aryl," as used herein, refers to a phenyl group, or a bicyclic fused ring system wherein one or more of the rings is a phenyl group. Bicyclic fused ring systems consist of a phenyl group fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl.

The term "arylalkyl," as used herein, refers to an aryl group attached to the parent molecular moiety through an alkyl group.

The term "arylalkylene," as used herein, refers to a divalent arylalkyl group, where one point of attachment to the parent molecular moiety is on the aryl portion and the other is on the alkyl portion.

The term "alkylarylalkyl," as used herein, refers to an alkylaryl group attached to the parent molecular moiety through an alkyl group.

The term "arylene," as used herein, refers to a divalent aryl group.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl.

The term "cycloalkylene," as used herein, refers to a divalent cycloalkyl group.

The term "cycloalkylmethyl," as used herein, refers to a cycloalkyl group attached to the parent molecular moiety through a —$CH_2$— group.

The term "heteroalkyl," as used herein, refers to an alkyl group wherein one to seven of the carbon atoms are replaced by a heteroatom selected from O, NH, and S.

The term "heteroalkylene," as used herein, refers to an alkylene group wherein one to seven of the carbon atoms are replaced by a heteroatom selected from O, NH, and S.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to a heterocyclyl group attached to the parent molecular moiety through an alkyl group.

The term "heterocyclylalkylene," as used herein, refers to a divalent heterocyclylalkyl group, where one point of attachment to the parent molecular moiety is on the heterocyclyl portion and the other is on the alkyl portion.

The term "heterocyclylene," as used herein, refers to a divalent heterocyclyl group.

The term "halo," as used herein, refers to Br, Cl, F, or I.

The term "carbonyl," as used herein, refers to —C(O)—.

The term "cyano," as used herein, refers to —CN.

The term "amino," as used herein, refers to —$NR^{19}R^{20}$, wherein $R^{19}$ and $R^{20}$ are defined herein.

As used herein, the phrase "donor atom" refers to the atom directly attached to a metal by a chemical bond.

The term "linker," as used herein, refers to a portion of a molecule that serves as a spacer between two other portions of the molecule. Linkers may also serve other functions as described herein.

The terms "chelator" and "chelator moiety," as used herein, refer to the moiety or group on a molecule that binds to a metal ion through one or more donor atoms. The chelator is optionally attached to the parent molecular moiety through a linker, $L^2$.

Examples of suitable $L^2$ groups include, but are not limited to, —C(O)$CH_2$—Ar—$CH_2$NHC(O)—, where Ar is an arylene group; —C(O)—; —C(O)—Het-NHNHC(O)—, where Het is heteroarylene; —$CH_2$—Ar—$CH_2$—, where Ar is an arylene group; —C(O)—Het-; as well as other groups disclosed herein. In certain embodiments of the compounds and/or diagnostic agents of the disclosure, the chelator is a surfactant capable of forming an echogenic substance-filled lipid sphere or microbubble.

In certain other embodiments, the chelator moiety has a formula selected from

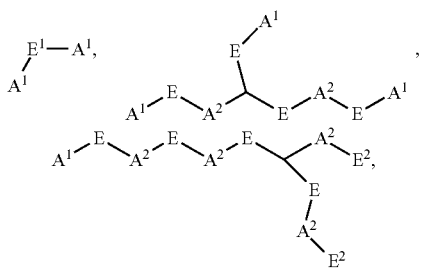

-continued

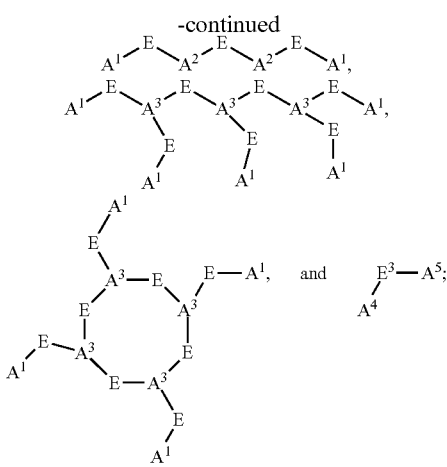

wherein
each $A^1$ is independently selected from —$NR^{19}R^{20}$, —$N(R^{26})_2$, —SH, —S(Pg), —OH, —$PR^{19}R^{20}$, —P(O)$R^{21}R^{22}$, —$CO_2H$, a bond to the parent molecular moiety, and a bond to $L^2$;
each $A^2$ is independently selected from $N(R^{26})$, $N(R^{19})$, S, O, $P(R^{19})$, and —OP(O)($R^{21}$)O—;
$A^3$ is N;
$A^4$ is selected from OH and OC(=O)$C_{1-20}$ alkyl;
$A^5$ is OC(=O)$C_{1-20}$ alkyl;
each E is independently selected from $C_{1-16}$alkylene substituted with 0-3 $R^{23}$, $C_{6-10}$arylene substituted with 0-3 $R^{23}$, $C_{3-10}$cycloalkylene substituted with 0-3 $R^{23}$, heterocyclyl-$C_{1-10}$alkylene substituted with 0-3 $R^{23}$, $C_{6-10}$aryl-$C_{1-10}$alkylene substituted with 0-3 $R^{23}$, $C_{1-10}$alkyl-$C_{6-10}$arylene substituted with 0-3 $R^{23}$, and heterocyclylene substituted with 0-3 $R^{23}$
$E^1$ is selected from a bond and E;
each $E^2$ is independently selected from $C_{1-16}$alkyl substituted with 0-3 $R^{23}$, $C_{6-10}$aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, $C_{1-10}$alkyl-$C_{6-10}$aryl substituted with 0-3 $R^{23}$, and heterocyclyl substituted with 0-3 $R^{23}$;
$E^3$ is $C_{1-10}$alkylene substituted with 1-3 $R^{32}$;
Pg is a thiol protecting group;
$R^{19}$ and $R^{20}$ are each independently selected from a bond to $L^2$, a bond to the parent molecular moiety, hydrogen, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$.
$R^{21}$ and $R^{22}$ are each independently selected from a bond $L^2$, a bond to the parent molecular moiety, —OH, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;
each $R^{23}$ is independently selected from a bond to $L^2$, a bond to the parent molecular moiety, =O, halo, trifluoromethyl, cyano, —$CO_2R^{24}$, —C(=O)$R^{24}$, —C(=O)N($R^{24}$)$_2$, —CHO, —$CH_2OR^{24}$, —OC(=O)$R^{24}$, —OC(=O)O$R^{24}$, —O$R^{24}$, —OC(=O)N($R^{24}$)$_2$, —$NR^{24}$C(=O)$R^{24}$, —$NR^{24}$C(=O)O$R^{24}$, —$NR^{24}$C(=O)N($R^{24}$)$_2$, —$NR^{24}SO_2N(R^{24})_2$, —$NR^{24}SO_2R^{24}$, —$SO_3H$, —$SO_2R^{24}$, —$SR^{24}$, —S(=O)$R^{24}$, —$SO_2N(R^{24})_2$, —N($R^{24}$)$_2$, —NHC(=S)$NHR^{24}$, =$NOR^{24}$, —$NO_2$, —C(=O)$NHOR^{24}$, —C(=O)

$NHNR^{24}R^{24}$, —$OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0-2 $R^{24}$, and heterocyclyl;
each $R^{24}$ is independently selected from a bond to $L^2$, a bond to the parent molecular moiety, hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl;
each $R^{26}$ is independently a coordinate bond to a metal or a hydrazine protecting group;
each $R^{32}$ selected from $R^{34}$, =O, —$CO_2R^{33}$, —C(=O)$R^{33}$, —C(=O)N($R^{33}$)$_2$, —$CH_2OR^{33}$, —$OR^{33}$, —N($R^{33}$)$_2$, and $C_2$-$C_4$ alkenyl;
each $R^{33}$ is independently selected from $R^{34}$, hydrogen, $C_1$-$C_6$ alkyl, phenyl, benzyl, and trifluoromethyl; and
$R^{34}$ is a bond to $L^2$;
wherein at least one of $A^1$, $R^{19}$, $R^{20}$, $R^{21}$, $R^{22}$, $R^{23}$, $R^{24}$, and $R^{34}$ is a bond to $L^2$ or the parent molecular moiety.
In some embodiments, each $R^{24}$ is independently hydrogen, $C_{1-6}$alkyl, phenyl, benzyl, or $C_{1-6}$alkoxy.
In an embodiment of the present disclosure, the chelant is of the formula:

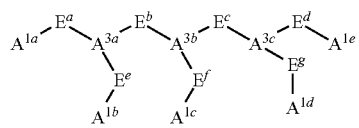

wherein
$A^{1c}$ is a bond to $L^2$;
$A^{1a}$, $A^{1b}$, $A^{1d}$ and $A^{1e}$ are each —$CO_2H$;
$A^{3a}$, $A^{3b}$, and $A^{3c}$ are each N;
$E^b$, and $E^c$ are $C_2$alkylene; and
$E^a$, $E^d$, $E^e$, $E^f$, and $E^g$ are $CH_2$.
In another embodiment of the present disclosure the chelant is of the formula:

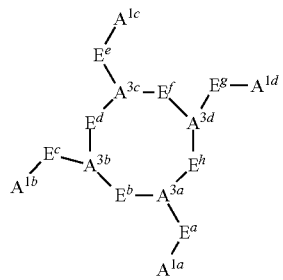

wherein:
$A^{3a}$, $A^{3b}$, $A^{3c}$ and $A^{3d}$ are each N;
$A^{1a}$ is a bond to $L^2$;
$A^{1b}$, $A^{1c}$ and $A^{1d}$ are each —$CO_2H$;
$E^a$, $E^c$, $E^g$ and $E^e$ are each $CH_2$; and
$E^b$, $E^d$, $E^f$ and $E^h$ are each $C_2$alkylene.
In another embodiment of the present disclosure, the chelant is of the formula:

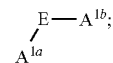

wherein
A$^{1a}$ is —N(R$^{26}$)$_2$;
A$^{1b}$ is NHR$^{19}$;
E is a bond;
R$^{19}$ is a bond to L$^2$; and
each R$^{26}$ is a co-ordinate bond to a metal.

In some embodiments, the chelator moiety comprises one of the following structures,

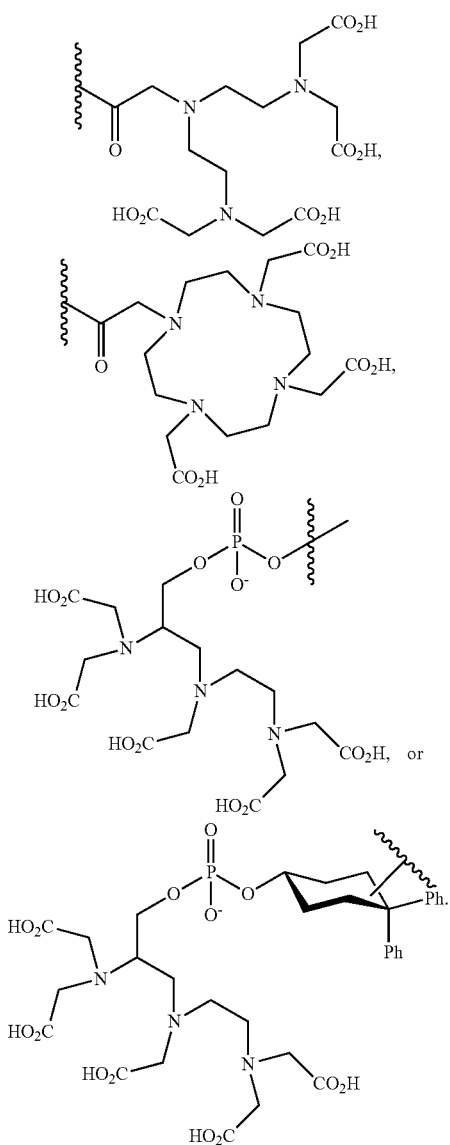

As used herein, the terms "ancillary" and "co-ligands" refers to ligands that serve to complete the coordination sphere of the radionuclide together with the chelator of the reagent. For radiopharmaceuticals comprising a binary ligand system, the radionuclide coordination sphere comprises one or more chelators from one or more reagents and one or more ancillary or co-ligands, provided that there are a total of two types of ligands or chelators. For example, a radiopharmaceutical comprised of one chelator from one reagent and two of the same ancillary or co-ligands and a radiopharmaceutical comprising two chelators from one or two reagents and one ancillary or co-ligand are both considered to comprise binary ligand systems. For radiopharmaceuticals comprising a ternary ligand system, the radionuclide coordination sphere comprises one or more chelators from one or more reagents and one or more of two different types of ancillary or co-ligands, provided that there are a total of three types of ligands or chelators. For example, a radiopharmaceutical comprised of one chelator from one reagent and two different ancillary or co-ligands is considered to comprise a ternary ligand system.

Ancillary or co-ligands useful in the preparation of radiopharmaceuticals and in diagnostic kits useful for the preparation of said radiopharmaceuticals comprise one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator of the reagent or reagents.

As used herein, the term "diagnostic agent" refers to a compound that may be used to detect, image and/or monitor the presence and/or progression of a condition(s), pathological disorder(s) and/or disease(s). It should be understood that all compounds of the present invention that contain an imaging agent are diagnostic agents. For example, a compound of Formula (I-A) wherein one of D$^1$ and D$^2$ is an imaging agent is a diagnostic agent.

The term "diagnostic imaging technique," as used herein, refers to a procedure used to detect a diagnostic agent.

The terms "diagnostic kit" and "kit", as used herein, refer to a collection of components in one or more vials that are used by the practicing end user in a clinical or pharmacy setting to synthesize diagnostic agents. The kit provides all the requisite components to synthesize and use the diagnostic agents (except those that are commonly available to the practicing end user such as water or saline for injection), such as a solution of the imaging agent or a precursor thereof, equipment for heating during the synthesis of the diagnostic agent, equipment necessary for administering the diagnostic agent to the patient such as syringes and shielding (if required), and imaging equipment.

The term "imaging moiety," as used herein, refers to a portion or portions of a molecule that contain an imaging agent. The term "imaging agent," as used herein, refers to an element or functional group in a diagnostic agent that allows for the detection, imaging, and/or monitoring of the presence and/or progression of a condition(s), pathological disorder(s), and/or disease(s). The imaging agent may be bound to the diagnostic agent via a bond, such as a covalent bond, an ionic bond, a hydrogen bond, a dative bond (e.g. complexation or chelation between metal ions and monodentate or multidentate ligands), or the like. For example, the imaging agent may be a paramagnetic metal ion bound to the diagnostic agent by chelation of the metal ion to a monodentate or multidentate ligand (e.g., chelating moiety) of the diagnostic agent. The imaging moiety may contain a linker, L$^3$, which connects the imaging agent to the parent molecular moiety. Examples of suitable L$^3$ groups include straight or branched chain alkylene groups, —C(O)—, and the like.

The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber.

Suitable echogenic gases include a sulfur hexafluoride or perfluorocarbon gas, such as perfluoromethane, perfluoroethane, perfluoropropane, perfluorobutane, perfluorocyclobutane, perfluoropentane, or perfluorohexane.

Suitable non-metallic isotopes include $^{11}$C, $^{14}$C, $^{13}$N, $^{18}$F, $^{123}$I, $^{124}$I, and $^{125}$I.

Suitable optical reporters include a fluorescent reporter and chemiluminescent groups.

Suitable radioisotopes include $^{99m}$Tc, $^{95}$Tc, $^{111}$In, $^{62}$Cu, $^{64}$Cu, $^{67}$Ga, $^{68}$Ga, and $^{153}$Gd. In a specific embodiment of the present disclosure suitable radioisotopes include $^{111}$In, $^{62}$Cu, $^{64}$Cu, $^{67}$Ga, $^{68}$Ga, and $^{153}$Gd.

Suitable paramagnetic metal ions include: Gd(III), Dy(III), Fe(III), and Mn(II).

Suitable X-ray absorbers include: Re, Sm, Ho, Lu, Pm, Y, Bi, Pd, Gd, La, Au, Yb, Dy, Cu, Rh, Ag, Ir and I.

As used herein, the term "metallopharmaceutical" means a pharmaceutical comprising a metal. The metal is the origin of the imageable signal in diagnostic applications and the source of the cytotoxic radiation in radiotherapeutic applications.

The term "radiopharmaceutical," as used herein, refers to a metallopharmaceutical in which the metal is a radioisotope.

As used herein, the phrase "pharmaceutically acceptable" refers to those compounds, diagnostic agents, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The compounds and/or diagnostic agents of the present disclosure can exist as pharmaceutically acceptable salts. The term "pharmaceutically acceptable salt," as used herein, represents salts or zwitterionic forms of the compounds and/or diagnostic agents of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds and/or diagnostic agents or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds and/or diagnostic agents by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, meglumine, piperidine, and piperazine.

In some embodiments, the compounds and/or diagnostic agents described herein may be provided in the absence of a counterion (e.g., as a free base).

As used herein, the term "reagent" means a compound of this disclosure capable of direct transformation into a diagnostic agent of this disclosure. Reagents may be utilized directly for the preparation of the diagnostic agents of this disclosure or may be a component in a kit of this disclosure.

As used herein, the term "lyophilization aid" means a component that has favorable physical properties for lyophilization, such as the glass transition temperature, and is added to the formulation to improve the physical properties of the combination of all the components of the formulation for lyophilization.

As used herein, the phrase "solubilization aid" is a component that improves the solubility of one or more other components in the medium required for the formulation.

As used herein, the phrase "stabilization aid" means a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting with species that degrade other components or the metallopharmaceutical.

The term "stable", as used herein, refers to compounds and/or diagnostic agents which possess the ability to allow manufacture and which maintain their integrity for a sufficient period of time to be useful for the purposes detailed herein. Typically, the compounds and/or diagnostic agents of the present disclosure are stable at a temperature of 40° C. or less in the absence of moisture or other chemically reactive conditions for at least a week.

The term "buffer," as used herein, refers to a substance used to maintain the pH of the reaction mixture from about 3 to about 10.

The term "sterile," as used herein, means free of or using methods to keep free of pathological microorganisms.

As used herein, the term "bacteriostat" means a component that inhibits the growth of bacteria in a formulation either during its storage before use of after a diagnostic kit is used to synthesize a diagnostic agent.

The term "carrier", as used herein, refers to an adjuvant or vehicle that may be administered to a patient, together with the compounds and/or diagnostic agents of this disclosure which does not destroy the activity thereof and is non-toxic when administered in doses sufficient to deliver an effective amount of the diagnostic agent and/or compound.

Asymmetric centers exist in the compounds and/or diagnostic agents of the present invention. These centers are designated by the symbols "R" or "S", depending on the configuration of substituents around the chiral carbon atom. It should be understood that the invention encompasses all stereochemical isomeric forms of the present compounds and/or diagnostic agents, or mixtures thereof, unless otherwise specifically stated. Individual stereoisomers of compounds and/or diagnostic agents can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds and/or diagnostic agents of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and/or diagnostic agents and mixtures thereof.

When any variable occurs more than one time in any substituent or in any formula, its definition on each occurrence is independent of its definition at every other occurrence. Thus, for example, if a group is shown to be substituted with 0-2 $R^{23}$, then said group may optionally be substituted with up to two $R^{23}$, and $R^{23}$ at each occurrence is selected independently from the defined list of possible $R^{23}$. Also, by way of example, for the group —$N(R^{24})_2$, each of the two $R^{24}$ substituents on the nitrogen is independently selected from the defined list of possible $R^{24}$. Combinations of substituents and/or variables are permissible only if such combinations result in stable compounds and/or diagnostic agents. When a bond to a substituent is shown to cross the bond connecting two atoms in a ring, then such substituent may be bonded to any atom on the ring.

When the imaging agent is a radioisotope, the compound may further comprise a first ancillary ligand and a second ancillary ligand capable of stabilizing the radioisotope. A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will affect the charge and lipophilicity of the radiopharmaceutical. For example, the use of 4,5-dihydroxy-1,3-benzenedisulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

It should also be understood that the compounds and/or diagnostic agents of this disclosure may adopt a variety of conformational and ionic forms in solution, in pharmaceutical compositions and in vivo. Although the depictions herein of specific compounds and/or diagnostic agents of this disclosure are of particular conformations and ionic forms, other conformations and ionic forms of those compounds and/or diagnostic agents are envisioned and embraced by those depictions.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, TRIS (tris(hydroxymethyl)amino-methane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this disclosure, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

In some cases, depending on the dose and rate of injection, the binding sites on plasma proteins may become saturated with prodrug and activated agent. This leads to a decreased fraction of protein-bound agent and could compromise its half-life or tolerability as well as the effectiveness of the agent. In these circumstances, it is desirable to inject the prodrug agent in conjunction with a sterile albumin or plasma replacement solution. Alternatively, an apparatus/syringe can be used that contains the contrast agent and mixes it with blood drawn up into the syringe; this is then re-injected into the patient.

The compounds, diagnostic agents and pharmaceutical compositions of the present disclosure may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

When administered orally, the pharmaceutical compositions of this disclosure may be administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this disclosure may be prepared by mixing the agent with a suitable non-irritating excipient that is solid at room temperature but liquid at rectal temperature and therefore will melt in the rectum to release the drug. Such materials include cocoa butter, beeswax and polyethylene glycols.

As noted before, the pharmaceutical compositions of this disclosure may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds and/or diagnostic agents of this disclosure include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, typically, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this disclosure are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated and the particular mode of administration. A typical preparation will contain from about 5% to about 95% active compound (w/w). Typically, such preparations contain from about 20% to about 80% active compound.

For intravenous and other types of administration, acceptable dose ranges range from about 0.001 to about 1.0 mmol/kg of body weight, with the typical dose of the active ingredient compound ranging from about 0.001 to about 0.5 mmol/kg of body weight. Even more typical is from about 0.01 to about 0.1 mmol/kg, and the most typical dose of the active ingredient compound is from about 0.0001 and to about 0.05 mmol/kg.

As the skilled artisan will appreciate, lower or higher doses than those recited above may be required. Specific dosage regimens for any particular patient will depend upon a variety of factors, including the activity of the specific compound employed, the age, body weight, general health status, sex, diet, time of administration, rate of excretion, drug combination and the judgment of the treating physician.

Buffers useful in the preparation of diagnostic agents and kits thereof include but are not limited to phosphate, citrate, sulfosalicylate, and acetate. A more complete list can be found in the United States Pharmacopeia.

Lyophilization aids useful in the preparation of diagnostic agents and kits thereof include but are not limited to mannitol, lactose, sorbitol, dextran, Ficoll, and polyvinylpyrrolidine (PVP).

Stabilization aids useful in the preparation of diagnostic agents and kits thereof include but are not limited to ascorbic acid, cysteine, monothioglycerol, sodium bisulfite, sodium metabisulfite, gentisic acid, and inositol.

Solubilization aids useful in the preparation of diagnostic agents and kits thereof include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Typical solubilizing aids are polyethylene glycol, and Pluronics copolymers.

Bacteriostats useful in the preparation of diagnostic agents and kits thereof include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or coligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the diagnostic agent and have a high degree of certainty that the diagnostic agent can be injected safely into a patient and will provide diagnostic information about the disease state of that patient.

The diagnostic kits of the present disclosure can also contain written instructions for the practicing end user to follow to synthesize the diagnostic agents. These instructions may be affixed to one or more of the vials or to the container in which the vial or vials are packaged for shipping or may be a separate insert, termed the package insert.

X-ray contrast agents, ultrasound contrast agents and metallopharmaceuticals for use as magnetic resonance imaging contrast agents are provided to the end user in their final form in a formulation contained typically in one vial, as either a lyophilized solid or an aqueous solution. The end user reconstitutes the lyophilized solid with water or saline and withdraws the patient dose or simply withdraws the dose from the aqueous solution formulation as provided.

These diagnostic agents, whether for gamma scintigraphy, positron emission tomography, MRI, ultrasound or x-ray image enhancement, are useful, inter alia, to detect and monitor changes in cardiovascular diseases over time.

Methods for synthesizing the compounds and diagnostic agents described herein are also provided. In some cases, the method may comprise reacting a compound and/or intermediate described herein, to produce a compound and/or diagnostic agent of the invention. For example, the method may comprise reacting a compound with an imaging agent to form a diagnostic agent, as described herein. In another example, the method may comprise reacting an intermediate molecule to produce a compound of the invention. In some cases, the intermediate molecule may be a compound comprising a hydroxylamine derivative, a hydroxamic acid, a hydroxamate ester, and amine, or the like. Other intermediate molecules are described herein, including the Examples. The method may further comprise isolating and/or purifying the compound and/or diagnostic agent, for example, by chromatography (e.g., column chromatography, HPLC), crystallization, filtration, solvent extraction, and the like. The method may also comprise characterization of the compound and/or diagnostic agent by mass spectrometry, NMR, and the like.

The compounds and/or diagnostic agents of the present disclosure can be prepared following the procedures described herein. In some cases, the compound and/or diagnostic agent may be synthesized by coupling a hydroxylamine derivative with a carbonyl group such as a carboxylic acid, acyl halide, ester, or the like, to form a hydroxamate ester. For example, Scheme 1 shows the condensation of a carboxylic acid moiety with a hydroxylamine derivative (e.g., $H_2NOR^4$) to form the hydroxamate ester.

In some cases, the hydroxylamine derivative may be substituted with a chelator moiety.

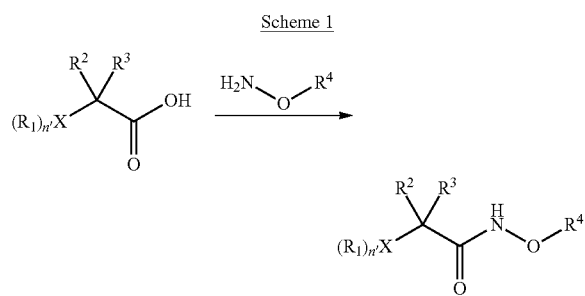

Scheme 1

In some embodiments, the compound and/or diagnostic agent may be synthesized by coupling hydroxylamine with a carbonyl group to form a hydroxamic acid, which may be further substituted with, for example, a chelator moiety. As shown in Scheme 2, reaction of a carboxylic ester moiety with hydroxylamine forms a hydroxyamic acid, which is then substituted at the oxygen with a species comprising a leaving group, i.e., $Y-R^4$, wherein Y is a leaving group and $R^4$ comprises a chelator moiety.

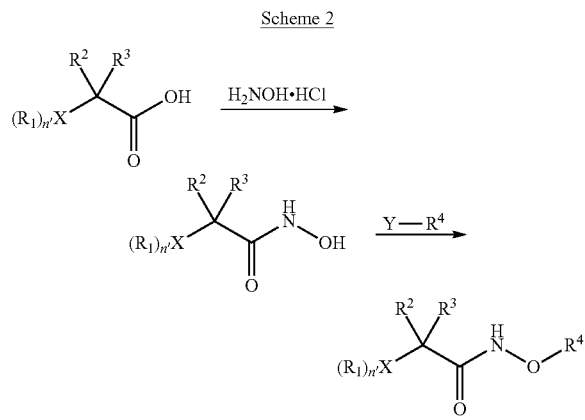

Scheme 2

Compounds and diagnostic agents described herein may also be synthesized using various methods known in the art to form carbon-carbon bonds, carbon-heteroatom bonds, and the like. For example, portions of the compounds and diagnostic agents may be bonded to one another via amino, ether, thioether, ester, thioester, amide, thiourea, or other linkages. In some cases, the chelator moiety may be bonded to the compound or diagnostic agent via an amide linkage.

Those of ordinary skill in the art would be able to select suitable methods for synthesizing a compound or diagnostic agent having a particular linkage. For example, methods for coupling amino acids or peptides, as described more fully below, may be used in the context of the invention to form an amide linkage between portions of the compound or diagnostic agent. In some cases, alkylation of an alcohol or a thiol may be used to form an ether or a thioether, respectively. For example, reaction of a thiol with an alkyl species comprising a leaving group (e.g., halo, tosyl, mesyl, or the like) may result in formation of a bond between the thioether and the alkyl group, i.e., a thioether. In some embodiments, the compounds or diagnostic agent may include a thiourea linkage, which can be formed using various methods known in the art, including an acylation reaction between an amine moiety and a isothiocyanate moiety.

In some cases, the Mitsunobu reaction may be utilized to form a wide ranges of linkages, including esters, phenyl ethers, thioethers, and others, by reaction of a nucleophile (e.g., an acidic nucleophile) with a primary or secondary alcohol in the presence of diethylazodicarboxylate (DEAD). Those of ordinary skill in the art would be able to select the appropriate nucleophile suitable for use in a particular application. For example, reaction between an alcohol and a phenol under Mitsunobu conditions may produce an aryl ether, while reaction between an alcohol an a carboxylic acid or thiol under Mitsunobu conditions may produce an ester or thioester, respectively.

Compounds and diagnostic agents described herein may also comprise a phosphonate ester linkage. In some embodiments, a phosphonate ester may be synthesized by coupling of a phosphonic acid and an alcohol, for example, in the presence of DEAD or dicyclocarbodiimide (DCC). Additional methods for synthesizing phosphonate esters are described in, for example, Savignac, P. et al., *Modern Phosphonate Chemistry*, CRC Press: New York, 2003, the contents of which are incorporated herein by reference.

Other methods for forming carbon-carbon bonds may be used to synthesize compounds or diagnostic agents described herein, such as olefin metathesis. As used herein, "metathesis" or "olefin metathesis" is given its ordinary meaning in the art and refers to a chemical reaction in which two reacting species exchange partners in the presence of a transition-metal catalyst, according to the formula shown in Scheme 3, forming a carbon-carbon double bond between the two reacting species and ethylene as a byproduct. Examples of different kinds of metathesis reactions including cross metathesis, ring-closing metathesis, ring-opening metathesis, acyclic diene metathesis, alkyne metathesis, enyne metathesis, and the like. Typically, metathesis reactions are performed in the presence of a metathesis catalyst, which may comprise ruthenium, molybdenum, or tungsten (e.g., Grubbs' $1^{st}$ generation catalyst, Grubbs' 2nd generation catalyst, Schrock's catalyst).

Scheme 3

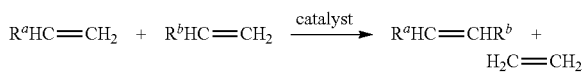

Metal-catalyzed cross-coupling reactions may also be used in the synthesis of compounds and diagnostic agents. For example, aryl halides may be reacted with various species in the presence of a metal catalyst to form linkages including biaryl ethers, acetylenes, alkenylaryls (e.g., styrene and styrene derivatives), arenes, and the like. Examples of cross-coupling reactions suitable for use in the context of the invention include the Ullmann, Sonogashira/Castro-Stevens, Heck, Stille, Suzuki, and other related reactions. Those of ordinary still in the art would be able to select the appropriate reactants, catalysts, and reaction conditions for synthesizing a particular desired compound or diagnostic agent.

Cycloaddition chemistry may also be used to synthesize compounds and diagnostic agents described herein. For example, "click" chemistry may be utilized, wherein a [3+2] cycloaddition between an azide-containing species and an alkyne-containing species may form a triazole linkage between the two species. Such reactions may be performed under mild conditions and with high tolerance for a wide range of functional groups.

In some cases, the compound or diagnostic agent may include a peptide, polypeptide, and/or peptidomimetic, which may be synthesized using various known methods. Generally, peptides, polypeptides and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described in *J. Am. Chem. Soc.*, 1963, 85, 2149-2154.

The peptides, polypeptides and peptidomimetics may also be synthesized using automated synthesizing equipment. In addition to the foregoing, procedures for peptide, polypeptide and peptidomimetic synthesis are described in Stewart and Young, *Solid Phase Peptide Synthesis,* 2nd Ed., Pierce Chemical Co., Rockford, Ill. (1984); Gross, Meienhofer, Udenfriend, Eds., *The Peptides: Analysis, Synthesis, Biology,* Vol. 1, 2, 3, 5, and 9, Academic Press, New York, (1980-1987); Bodanszky, *Peptide Chemistry: A Practical Textbook,* Springer-Verlag, New York (1988); and Bodanszky et al., *The Practice of Peptide Synthesis,* Springer-Verlag, New York (1984).

The coupling between two amino acid derivatives, an amino acid and a peptide, polypeptide or peptidomimetic, two peptide, polypeptide or peptidomimetic fragments, or the cyclization of a peptide, polypeptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole or 1-hydroxy-7-azabenzotriazole. These coupling reactions may be performed either in solution (liquid phase) or on a solid phase, such as polystyrene or a suitable resin (vide infra).

The functional groups of the constituent amino acids or amino acid mimetics are typically protected during the coupling reactions to avoid undesired bonds being formed. The protecting groups that can be used are listed in Greene, *Protective Groups in Organic Synthesis*, John Wiley & Sons, New Jersey (2007) and *The Peptides: Analysis, Synthesis, Biology*, Vol. 3, Academic Press, New York (1981).

The α-carboxyl group of the C-terminal residue may be protected by an ester that can be cleaved to give the carboxylic acid. These protecting groups include:
(1) alkyl esters such as methyl and t-butyl;
(2) aryl esters such as benzyl and substituted benzyl, or
(3) esters that can be cleaved by mild base treatment or mild reductive means such as trichloroethyl and phenacyl esters.

In the solid phase case, the C-terminal amino acid is attached to an insoluble carrier (usually polystyrene). These insoluble carriers contain a group that will react with the carboxyl group to form a bond which is stable to the elongation conditions but readily cleaved later. Examples include: oxime resin (DeGrado and Kaiser (1980) *J. Org. Chem.* 45, 1295-1300) chloro or bromomethyl resin, hydroxymethyl resin, and aminomethyl resin. Many of these resins are commercially available with the desired C-terminal amino acid already incorporated.

The α-amino group of each amino acid is typically protected, e.g., by an α-amino protecting group. Any protecting group known in the art may be used. Examples of these are:
(1) acyl types such as formyl, trifluoroacetyl, phthalyl, and p-toluenesulfonyl;
(2) aromatic carbamate types such as benzyloxycarbonyl (Cbz) and substituted benzyloxycarbonyls, 1-(p-biphenyl)-1-methylethoxycarbonyl, and 9-fluorenyl-methyloxycarbonyl (Fmoc);
(3) aliphatic carbamate types such as tert-butyloxycarbonyl (Boc), ethoxycarbonyl, diisopropylmethoxycarbonyl, and allyloxycarbonyl;
(4) cyclic alkyl carbamate types such as cyclopentyloxycarbonyl and adamantyloxycarbonyl;
(5) alkyl types such as triphenylmethyl and benzyl;
(6) trialkylsilane such as trimethylsilane; and
(7) thiol containing types such as phenylthiocarbonyl and dithiasuccinoyl.

Typical α-amino protecting groups are either Boc or Fmoc. Many amino acid or amino acid mimetic derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

The amino acids or amino acid mimetics bearing side chain functionalities are typically protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide, polypeptide or peptidomimetic. The selection of such a protecting group is important in that it must not be removed during the deprotection and coupling of the α-amino group.

For example, when Boc is chosen for the α-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or tert-butylsulfonyl for cysteine; and the indole of tryptophan can either be left unprotected or protected with a formyl group.

When Fmoc is chosen for the α-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide, polypeptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free α-carboxylate and a free α-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (*Tetrahedron Letters,* 1990, 43, 6121-6124). When the oxime resin is employed, the Boc protection scheme is generally chosen. Then, a typical method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this disclosure can be synthesized by standard methods familiar to those skilled in the art (*The Peptides: Analysis, Synthesis, Biology,* Vol. 5, pp. 342-449, Academic Press, New York (1981)). N-Alkyl amino acids can be prepared using procedures described previously (Cheung et al., *Can. J. Chem.,* 1977, 55, 906; Freidinger et al., *J. Org. Chem.,* 1982, 48, 77).

The chelator is selected to form stable complexes with the metal ion chosen for a particular application. Chelators for diagnostic radiopharmaceuticals are selected to form stable complexes with the radioisotopes that have imageable gamma ray or positron emissions, such as $^{111}$In, $^{62}$Cu, $^{60}$Cu, $^{64}$Cu, $^{67}$Ga, $^{68}$Ga, $^{86}$Y, $^{153}$Gd.

Chelators for copper and gallium isotopes are selected from diaminedithiols, monoamine-monoamidedithiols, triamide-monothiols, monoamine-diamide-monothiols, diaminedioximes, and hydrazines. The chelators are generally tetradentate with donor atoms selected from nitrogen, oxygen and sulfur. The thiol sulfur atoms and the hydrazines may bear a protecting group which can be displaced either prior to using the reagent to synthesize a radiopharmaceutical or more often in situ during the synthesis of the radiopharmaceutical.

Exemplary thiol protecting groups include those listed in Greene and Wuts, *Protective Groups in Organic Synthesis,* John Wiley & Sons, New Jersey (2007). Any thiol protecting group known in the art may be used. Examples of thiol protecting groups include, but are not limited to, the following: acetamidomethyl, benzamidomethyl, 1-ethoxyethyl, benzoyl, and triphenylmethyl.

Chelators and chelator moieties for such metals as indium (e.g. $^{111}$In), yttrium (e.g. $^{86}$Y & $^{90}$Y), and lanthanides (e.g. Eu(III), Gd(III), and Dy(III)) are selected from cyclic and acyclic polyaminocarboxylates such as DTPA, DOTA, DO3A, 2-benzyl-DOTA, alpha-(2-phenethyl) 1,4,7,10-tetraazacyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine. Additional chelators suitable for use in the inventions are described in U.S. Pat. Nos. 5,362,475; 6,676,929; and 7,060,250, each of which is incorporated here by reference in its entirety. Procedures for synthesizing these chelators that are not commercially available can be found in *J. Chem. Soc. Perkin Trans.,* 1992, 1, 1175; *Bioconjugate Chem.,* 1991, 2, 187; *J. Nucl. Med.,* 1990, 31, 473; U.S. Pat. Nos. 5,064,956; and 4,859,777, each of which is incorporated here by reference in its entirety.

The coordination sphere of metal ion includes all the ligands or groups bound to the metal. For a transition metal complex to be stable it typically has a coordination number (number of donor atoms) comprised of an integer greater than or equal to 4 and less than or equal to 8; that is there are 4 to 8 atoms bound to the metal and it is said to have a complete coordination sphere. For a lanthanide series or actinide series metal complex, the metal typically has a coordination number (number of donor atoms) comprised of an integer greater than or equal to 4 and less than or equal to 10; that is there are 4 to 10 atoms bound to the metal and it is said to have a complete coordination sphere. The requisite coordination number for a stable metallopharmaceutical complex is determined by the identity of the element, its oxidation state, and the type of donor atoms. If the chelator does not provide all of the atoms necessary to stabilize the metal complex by completing its coordination sphere, the coordination sphere is completed by donor atoms from other ligands, termed ancillary or co-ligands, which can also be either terminal or chelating.

Ancillary ligands $A_{L1}$ are comprised of one or more hard donor atoms such as oxygen and amine nitrogen (sp$^3$ hybridized). The donor atoms occupy at least one of the sites in the coordination sphere of the radionuclide metal; the ancillary ligand $A_{L1}$ serves as one of the ligands in the ligand system. Examples of ancillary ligands $A_{L1}$ include but are not limited to water, dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2- or 3,4-hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris (methylacetic)acid, 2-benzyl-cyclohexyldiethylenetriaminepentaacetic acid, 2-benzyl-6-methyl-DTPA, and 6,6"- bis[N,N",N",N"-tetra(carboxymethyl)aminomethyl]-4'-(3-amino-4-methoxyphenyl)-2,2':6',2"-terpyridine.

As noted above, methods for treating a patient are provided. The method may comprise administration of a compound or diagnostic agent described herein to a patient and acquiring an image of a site of concentration of the diagnostic agent in the patient by a diagnostic imaging technique. The treatment may include the detection, imaging, and/or monitoring of elastin-rich tissues in a patient, including elastin-rich tissues located within the arterial wall, uterus, lung, skin, and/or ligaments. In some cases, the treatment includes the detection, imaging, and/or monitoring of the presence and/or amount of coronary plaque, carotid plaque, iliac/femoral plaque, aortic plaque, renal artery plaque, plaque of any arterial vessel, aneurism, vasculitis, other diseases of the arterial wall, and/or damage or structural changes in ligaments, uterus, lungs or skin in a patient.

The rate of clearance from the blood is of particular importance for cardiac imaging procedures, since the cardiac blood pool is large compared to the disease foci that one desires to image. For an effective arterial wall imaging agent, the target to background ratios (disease foci-to-blood and disease foci-to-muscle) are typically greater or equal to about 1.5, typically greater or equal to about 2.0, and more typically even greater. Certain pharmaceuticals of the present disclosure have blood clearance rates that result in less than about 5% i.d./g at 1 hour post-injection, measured in a mouse model. In one embodiment diagnostic agents of the present disclosure have blood clearance rates that result in less than about 2% i.d./g at 1 hour post-injection, measured in a mouse model.

The indium, copper, gallium, and yttrium diagnostic agents of the present disclosure can be easily prepared by admixing a salt of a radionuclide and a reagent of the present disclosure in an aqueous solution at temperatures from about 0° C. to about 100° C. These radionuclides are typically obtained as a dilute aqueous solution in a mineral acid, such as hydrochloric, nitric or sulfuric acid. The radionuclides are combined with from one to about one thousand equivalents of the reagents of the present disclosure dissolved in aqueous solution. A buffer is typically used to maintain the pH of the reaction mixture from about 3 to about 10.

The gadolinium, dysprosium, iron and manganese diagnostic agents of the present disclosure can be easily prepared by admixing a salt of the paramagnetic metal ion and a reagent of the present disclosure in an aqueous solution at temperatures from about 0° C. to about 100° C. These paramagnetic metal ions are typically obtained from commercial sources as their oxide, chloride or nitrate salts. The paramagnetic metal ions are combined with from one to about one thousand equivalents of the reagents of the present disclosure dissolved in aqueous solution. A buffer is typically used to maintain the pH of the reaction mixture from about 3 to about 10.

The total time of preparation will vary depending on the identity of the metal ion, the identities and amounts of the reactants and the procedure used for the preparation. The preparations may be complete, resulting in greater than about 80% yield of the radiopharmaceutical, in about 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

The diagnostic radiopharmaceuticals are administered by intravenous injection, usually in saline solution, at a dose of about 1 to about 100 mCi per 70 kg body weight, or typically at a dose of about 5 to about 50 mCi. Imaging is performed using known procedures.

The diagnostic agents of the disclosure containing a magnetic resonance imaging contrast component may be used in a similar manner as other MRI agents as described in U.S. Pat. Nos. 5,155,215; 5,087,440; Magn. Reson. Med., 1986, 3, 808; Radiology, 1988, 166, 835; and Radiology, 1988, 166, 693. Generally, sterile aqueous solutions of the contrast agents are administered to a patient intravenously in dosages ranging from about 0.01 to about 1.0 mmoles per kg body weight.

For use as X-ray contrast agents, the diagnostic agents of the present disclosure should generally have a heavy atom concentration of about 1 mM to about 5 M, typically about 0.1 M to about 2 M. Dosages, administered by intravenous injection, will typically range from about 0.5 mmol/kg to 1.5 mmol/kg, typically about 0.8 mmol/kg to 1.2 mmol/kg. Imaging is performed using known techniques, typically X-ray computed tomography.

The diagnostic agents of the disclosure containing ultrasound contrast components are administered by intravenous injection in an amount of about 10 to about 30 μL of the echogenic gas per kg body weight or by infusion at a rate of about 3 μL/kg/min. Imaging may be performed using known techniques of sonography.

Other features of the disclosure will become apparent in the course of the following descriptions of exemplary embodiments which are given for illustration of the disclosure and are not intended to be limiting thereof. The present disclosure will now be illustrated by reference to the following specific, non-limiting examples. Those skilled in the art of organic synthesis may be aware of still other synthetic routes to the disclosure compounds and/or diagnostic agents. The reagents and intermediates used herein are either commercially available or prepared according to standard literature procedures, unless otherwise described.

This disclosure is intended to encompass compounds having formula (I) when prepared by synthetic processes or by metabolic processes including those occurring in the human or animal body (in vivo) or processes occurring in vitro. For example, compounds of the present disclosure where A is a peptide consisting of a D-amino acid residue and a second D-amino acid may be generated by cleavage of a larger sequence (e.g., a peptide consisting of 3 amino acids and a D-amino acid residue) either synthetically or in vivo.

EXAMPLE 1

2-{[2-({[N-({4-[((2R)-2-amino-4-phenylbutanoyl-aminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

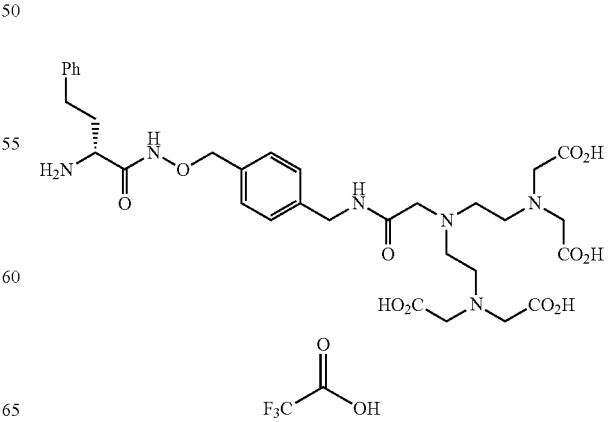

Part A—Preparation of N-(1-(N-hydroxycarbamoyl) (1R)-3-phenylpropyl)(tert-butoxy)-carboxamide

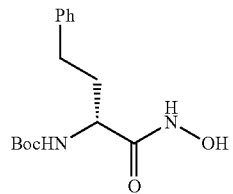 [SMILES: CC(C)(C)OC(=O)N[C@H](CCc1ccccc1)C(=O)NO]

A solution of Boc-DHfe-OH (1.40 g, 5.00 mmol) in 4:1 CH$_2$Cl$_2$/MeOH (25.0 mL) was treated with (trimethylsilyl) diazomethane (6.00 mmol; 3.00 mL of a 2.0 M solution in Et$_2$O) dropwise over 0.25 h at 22° C. CAUTION: vigorous gas evolution. The resulting yellow solution was stirred an additional 0.25 h to ensure complete methylation (R$_f$=0.7 in 1:1 EtOAc/hexanes). Excess (trimethylsilyl)diazomethane was consumed by the dropwise addition of glacial AcOH, then all volatiles removed in vacuo. The crude ester was redissolved in MeOH (25.0 mL), cooled to 0° C. and treated with a previously prepared suspension of H$_2$NOH.HCl (1.04 g, 15.0 mmol) and KOH (1.68 g, 30.0 mmol) in MeOH (25.0 mL); a large bore cannula needle was required for the transfer. The resulting suspension then warmed slowly to 22° C. over 3.5 h as the ice bath melted; the suspension stirred at 22° C. for 0.75 h of the time interval. The suspension was acidified with conc. HCl to pH 4-5 then all volatiles removed in vacuo. The solids were triturated with several portions of hot EtOAc (5×10 mL) and removed by filtration through a scintered glass funnel of medium porosity. The combined filtrates were collected and concentrated in vacuo to an off-white powder (R$_f$=0.7 in 9:1 CH$_2$Cl$_2$/MeOH). Purification through recrystallization from hot EtOAc (150 mL) afforded a white microcrystalline solid (0.893 g, 3.03 mmol; 60.6%). Mp 165.5-166.0° C. $^1$H NMR (DMSO-d$_6$, 300 MHz): δ 10.5 (1H, brs), 8.79 (1H, brs), 7.30-7.25 (2H, m), 7.19-7.14 (3H, m), 6.96 (1H, brd, J=8.1 Hz), 3.82 (1H, dt, J=7.5, 7.5 Hz), 2.66-2.45 (2H, m), 1.87-1.74 (2H, m), 1.39 (9H, s). $^{13}$C NMR (DMSO-d$_6$, 75 MHz): δ 168.8, 155.2, 141.3, 128.3, 128.2, 125.7, 77.9, 51.8, 33.8, 31.6, 28.2. HRMS calcd for C$_{15}$H$_{22}$N$_2$O$_4$ (M+Na): 317.1472. Found: 317.1466. The optical purity of the product was established by chiral GLC analysis (99.9% D-homophenylalanine).

part B—Preparation of N-{[4-(hydroxymethyl)phenyl]methyl}prop-2-enyloxycarboxamide

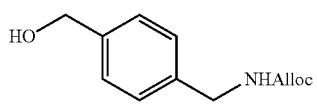

A suspension of methyl 4-(aminomethyl)benzoate hydrochloride (1.01 g, 5.00 mmol) in THF (50.0 mL) was treated with i-Pr$_2$NEt (2.09 mL, 12.0 mmol) then cooled to 0° C. Allyl chloroformate (638 μL, 6.00 mmol) was then added over 10 min and the resulting suspension stirred 50 min at 0° C. The reaction mixture was diluted with H$_2$O (50 mL), the layers separated and the aqueous layer washed with Et$_2$O (3×50 mL). The combined THF and Et$_2$O solutions were dried over MgSO$_4$, filtered and concentrated in vacuo to a white solid (R$_f$=0.5 in 1:1 hexanes/EtOAc) which was used without further purification in the subsequent reduction step.

The crude ester (5.00 mmol theoretical) was dissolved in dry THF (20.0 mL), cooled to 0° C. and treated with LiAlH$_4$ (5.00 mmol; 5.00 mL of a 1 M solution in THF) dropwise over 0.25 h using a syringe pump. The resulting solution was stirred 0.25 h at 0° C. to ensure complete reduction. Excess LiAlH$_4$ was consumed by the careful addition of H$_2$O (200 μL). The resulting white suspension was successively treated with 15% aqueous NaOH (200 μL) and H$_2$O (600 μL) then stirred for 0.25 h to a fine white slurry. The resulting mixture was filtered through a pad of Celite and concentrated in vacuo. The crude oil was purified by chromatography on silica (40×185 mm) using 1:1 hexanes/EtOAc (R$_f$=0.3). The main product eluted between 430-680 mL, was collected and concentrated to afford a white crystalline solid (0.923 g, 4.17 mmol; 83.4% over two steps). Mp 80.0-81.0° C. $^1$H NMR (CDCl$_3$, 300 MHz): δ 7.32 (2H, AB, J$_{AB}$=8.2 Hz), 7.26 (2H, AB, J$_{AB}$=8.2 Hz), 5.91 (1H, ddt, J=17.2, 10.4, 5.6 Hz), 5.30 (1H, dq, J=17.2, 1.4 Hz), 5.20 (1H, dq, J=10.5, 1.3 Hz), 4.65 (2H, s), 4.58 (2H, brdt, J=5.6, 1.3 Hz), 4.34 (2H, brd, J=5.7 Hz), 1.85 (1H, s). $^{13}$C NMR (CDCl$_3$, 75 MHz): δ 156.3, 140.3, 137.8, 132.8, 127.7, 127.3, 117.7, 65.7, 64.9, 44.8. HRMS calcd for C$_{12}$H$_{15}$NO$_3$ (M+H): 222.1125. Found: 222.1124.

part C—Preparation of N-{[4-(bromomethyl)phenyl]methyl}prop-2-enyloxycarboxamide

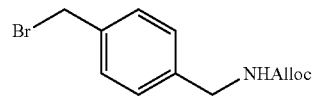

A solution of the product of Part 1B (0.664 g, 3.00 mmol) and CBr$_4$ (1.19 g, 3.60 mmol) in dry CH$_2$Cl$_2$ (30.0 mL) was cooled to 0° C. and treated with PPh$_3$ (0.905 g, 3.45 mmol) portion-wise over 5 min. After 10 min at 0° C., the solution was warmed to 22° C., stirred 20 min then concentrated in vacuo. The crude residue was purified by chromatography on silica (25×170 mm) using 3:2 hexanes/EtOAc (R$_f$=0.6 in 1:1 hexanes/EtOAc). The main product eluted between 95-185 mL, was collected and concentrated to afford a white crystalline solid (0.738 g, 2.60 mmol; 86.6%). Mp 80.0-82.0° C. $^1$H NMR (CDCl$_3$, 300 MHz): δ 7.36 (2H, AA'BB'. J$_{AB}$=8.2 Hz, J$_{AA'}$=1.9 Hz), 7.26 (2H, AB, J$_{AB}$=8.1 Hz), 5.92 (1H, ddt, J=17.2, 10.4, 5.6 Hz), 5.30 (1H, brd, J=17.0 Hz), 5.21 (1H, dq, J=10.4, 1.3 Hz), 4.59 (2H, brdt, J=5.6, 1.2 Hz), 4.47 (2H, s), 4.36 (2H, d, J=6.1 Hz). $^{13}$C NMR (CDCl$_3$, 75 MHz): δ 156.2, 138.9, 137.1, 132.8, 129.4, 127.9, 117.8, 65.8, 44.7, 33.1. HRMS calcd for C$_{12}$H$_{14}$BrNO$_2$ (M+H): 284.0281. Found: 284.0280.

part D—Preparation of (2R)-N-{[4-(aminomethyl)phenyl]methoxy}-2-[(tert-butoxy)carbonyl-amino]-4-phenylbutanamide, trifluoroacetic acid salt

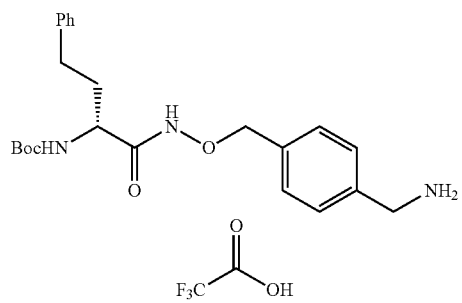

A solution of the product of Part 1A (0.662 g, 2.25 mmol) in dry DMF (9.00 mL) was treated with $K_2CO_3$ (0.373 g, 2.70 mmol) and cooled to 0° C. Part 1C (0.256 g, 0.900 mmol) was then added in one portion and the resulting suspension warmed slowly to 22° C. overnight as the ice bath melted. After 13 h total, the reaction mixture was partitioned between EtOAc (150 mL) and $H_2O$ (50 mL) with transfer to a separatory funnel. The layers were separated and the EtOAc layer washed with saturated aqueous NaCl (3×50 mL) then dried over $MgSO_4$, filtered and concentrated in vacuo to a white powder that was used without further purification in the subsequent deprotection step ($R_f$=0.4 in 1:1 hexanes/EtOAc).

The crude hydroxamate ester (0.900 mmol theoretical) was dissolved in 2:1 $MeCN/H_2O$ (9.00 mL) and successively treated with 51.2 mg TPPTS (90.0 µmol; 10 mol %), $Et_2NH$ (233 µL, 2.25 mmol) and 10.1 mg $Pd(OAc)_2$ (45.0 µmol; 5 mol %) at 22° C. Complete deprotection was observed within 0.5 h. The amber solution was filtered through a 0.45 µm Acrodisk then directly purified by HPLC on a Phenomenex Luna C18 column (21.2×250 mm) using a 1%/min gradient from 0-40% MeCN containing 0.1% TFA and 10% $H_2O$ at 20 mL/min. The main product peak eluting at 32 min was collected and lyophilized to a white powder (158 mg, 0.300 mmol; 33.3%). $^1H$ NMR (DMSO-$d_6$, 600 MHz): δ 11.25 (1H, brs), 8.20 (3H, brs), 7.44 (4H, brs), 7.27 (2H, dd, J=7.6, 7.6 Hz), 7.17 (1H, t, J=7.3 Hz), 7.15 (2H, d, J=7.3 Hz), 7.08 (1H, brd, J=7.6 Hz), 4.78 (2H, brs), 4.02 (2H, brs), 3.76 (1H, dt, J=7.3, 7.1 Hz), 2.60-2.55 (1H, m), 2.50-2.45 (1H, m), 1.81-1.77 (2H, m), 1.39 (9H, s). $^{13}C$ NMR (DMSO-$d_6$, 151 MHz): δ 169.0, 157.8 (q, J=31.1 Hz), 155.2, 141.2, 136.3, 133.8, 128.8, 128.7, 128.2, 125.8, 117.2, (q, J=300 Hz), 78.1, 76.3, 51.9, 42.0, 33.5, 31.5, 28.2. HRMS calcd for $C_{23}H_{31}N_3O_4$ (M+H): 414.2387. Found: 414.2392.

part E—Preparation of 2-{[2-({[N-({4-[((2R)-2-amino-4-phenylbutanoylaminooxy)methyl]-phenyl}methyl)carbamoyl]methyl}{2-bis(carboxymethyl)amino]ethyl}amino)ethyl]-(carboxymethyl)amino}acetic acid, trifluoroacetic acid salt

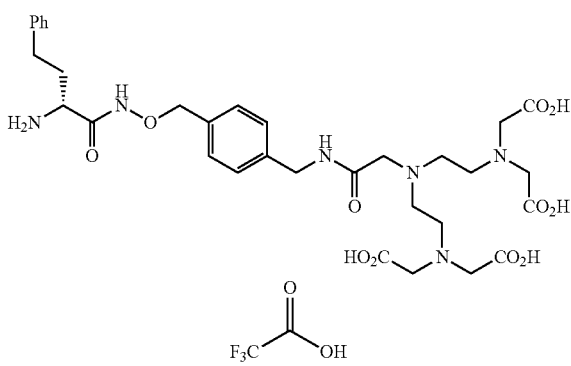

A solution of 2-{bis[2-(bis{[(tert-butyl)oxycarbonyl]methyl}amino)ethyl]amino}acetic acid (24.2 mg, 39.2 µmol; for leading references on the synthesis and characterization of DTPA and related analogs, see: a) Williams, M. A.; Rapoport, H. *J. Org. Chem.* 1993, 58, 1151. b) Anelli, P. L.; Fedeli, F.; Gazzotti, O.; Lattuada, L.; Lux, G.; Rebasti, F. *Bioconjugate Chem.* 1999, 10, 137.) in dry DMF (3.27 mL) was successively treated with HOBt (6.0 mg, 39 µmol), i-$Pr_2NEt$ (14 µL, 78 µmol) and HBTU (14.9 mg, 39.2 µmol) at 22° C. After 0.25 h, the solution was transferred using a cannula to the product of Part 1D (15.0 mg, 32.7 µmol) and the resulting solution stirred 0.25 h. To complete conversion, the solution was further treated with HBTU (7.43 mg, 19.6 µmol) and i-$Pr_2NEt$ (28.0 µL, 161 µmol), stirred 0.25 h, then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of $NaHCO_3$ and NaCl (3×30 mL each) then dried over $MgSO_4$, filtered and concentrated in vacuo to a colorless oil which was used without further purification in the subsequent deprotection step ($R_f$=0.4 in 9:1 $CH_2Cl_2$/MeOH).

The protected conjugate (32.7 µmol theoretical) was dissolved in dioxane (650 µL) then successively treated with $H_2O$ (3 µL) and HCl (2.60 mmol; 0.650 mL of a 4 M solution in dioxane) at 22° C. The resulting pale yellow solution was stirred and monitored over 4 h during which time a heavy white precipitate formed. Upon complete deprotection, the volatiles were removed under a stream of $N_2$ and the white solid residue redissolved in $H_2O$ containing 0.1% TFA (8.50 mL) then directly purified by HPLC on a Phenomenex Luna C18 column (21.2×250 mm) using a 1%/min gradient from 0-40% MeCN containing 0.1% TFA and 10% $H_2O$ at 20 mL/min. The main product peak eluting at 25 min was collected and lyophilized to a white powder (22.8 mg, 22.1 µmol; 67.6%). $^1H$ NMR (DMSO-$d_6$, 300 MHz): δ 11.77 (1H, brs), 8.95 (1H, brt, J=4.9 Hz), 8.35 (3H, brs), 7.40 (2H, AB, $J_{AB}$=8.0 Hz), 7.32-7.27 (4H, m), 7.20 (1H, dd, J=7.4, 7.4 Hz), 7.13 (2H, AB, $J_{AB}$=7.2 Hz), 4.84 (2H, AB, J=11.6 Hz), 4.34 (2H, brd, J=5.6 Hz), 4.25 (2H, s), 3.64 (1H, brs), 3.50 (8H, s), 3.38 (4H, brt, J=5.6 Hz), 3.05 (4H, brt, J=5.7 Hz), 2.55-2.50 (2H, m), 1.97-1.90 (2H, m). $^{13}C$ NMR (DMSO-$d_6$, 151 MHz): δ 172.7, 165.3, 164.8, 158.0 (q, J=32.4 Hz), 140.2, 138.7, 134.3, 129.0, 128.5, 128.1, 127.3, 126.2, 116.8 (q, J=298 Hz), 76.9, 54.3, 53.9, 52.2, 50.3, 48.6, 42.1, 32.8, 30.3. HRMS calcd for $C_{32}H_{44}N_6O_{11}$ (M+Na): 711.2960. Found: 711.2964. The optical purity of the product was established by chiral GLC analysis (99.8% D-homophenylalanine).

EXAMPLE 2

2-(7-{[N-({4-[((2R)-2-amino-4-phenylbutanoylaminooxy)methyl]phenyl}methyl)carbamoyl]methyl}-1,4,7,10-tetraaza-4,10-bis(carboxymethyl)cyclododecyl)acetic acid, trifluoroacetic acid salt

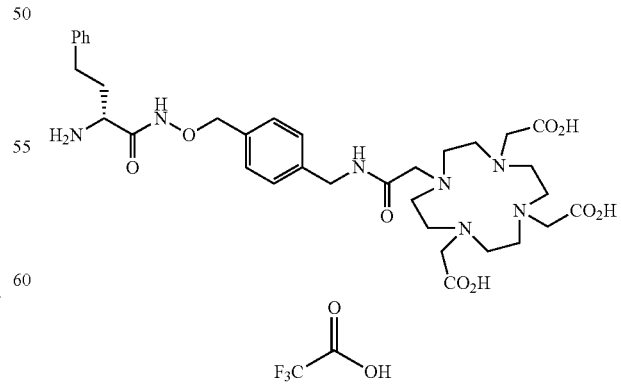

A solution of 2-(1,4,7,10-tetraaza-4,7,10-tris{[(tert-butyl)oxycarbonyl]methyl}-cyclododecyl)acetic acid (109 mg, 0.190 mmol) in dry DMF (10.0 mL) was successively treated with HOBt (29.0 mg, 0.190 mmol), HBTU (71.9 mg, 0.190 mmol) and i-Pr$_2$NEt (40.8 μL, 0.234 mmol) at 22° C. After 0.25 h, the solution was treated with the product of Part 1D (0.158 mmol; 5.80 mL of a 0.027 M solution in DMF) and the resulting solution stirred 3 h. To complete conversion the solution was further treated with 30 mol % of the active ester, stirred 0.25 h, then diluted with EtOAc (75 mL) with transfer to a separatory funnel. The EtOAc solution was washed with 0.1 M citric acid (3×75 mL), followed by saturated aqueous solutions of NaHCO$_3$ and NaCl (3×75 mL each), then dried over MgSO$_4$, filtered and concentrated in vacuo to a colorless oil which was used without further purification in the subsequent deprotection step.

The protected conjugate (0.158 mmol theoretical) was dissolved in dioxane (3.16 mL) then successively treated with H$_2$O (15 μL) and HCl (12.6 mmol; 3.16 mL of a 4 M solution in dioxane) at 22° C. The resulting pale yellow solution was stirred 16 h, during which time a heavy white precipitate formed. Upon complete deprotection, the volatiles were removed under a stream of N$_2$ and the white solid residue redissolved in H$_2$O (8.00 mL) then directly purified by HPLC on a Phenomenex Luna C18 column (21.2×250 mm) using a 1%/min gradient from 0-40% MeCN containing 0.1% TFA and 10% H$_2$O at 20 mL/min. The main product peak eluting at 25 min was collected and lyophilized to a white powder (43.0 mg, 41.3 μmol; 26.1%). $^1$H NMR (DMSO-d$_6$, 600 MHz): δ 9.04 (1H, brt, J=6.0 Hz), 7.46 (2H, AB, J$_{AB}$=8.0 Hz), 7.38 (2H, AB, J$_{AB}$=8.0 Hz), 7.28-7.25 (3H, m), 7.20-7.16 (3H, m), 5.01 (2H, AB, J$_{AB}$=11.6 Hz), 4.47 (2H, brd, J=5.7 Hz), 4.13 (1H, t, J=6.6 Hz), 3.86 (4H, s), 3.85 (2H, s), 3.73 (2H, s), 3.16 (10H, brs), 3.08 (2H, brs), 2.81-2.76 (2H, m), 2.30-2.21 (2H, m). $^{13}$C NMR (DMSO-d$_6$, 151 MHz): δ 171.5, 165.3, 157.8 (q, J=31.4 Hz), 140.2, 138.8, 134.3, 128.9, 128.5, 128.0, 127.4, 126.2, 117.1 (q, J=299 Hz), 76.9, 54.8, 54.0, 53.1, 50.6, 50.4, 50.2, 48.8, 42.0, 32.8, 30.3. HRMS calcd for C$_{34}$H$_{49}$N$_7$O$_9$ (M+H): 700.3665. Found: 700.3659.

EXAMPLE 3

2-{[2-({[N-({4-[((2S)-2-amino-4-phenylbutanoylaminooxy)methyl]-phenyl}methyl)carbamoyl]methyl}{2-[bis(carboxymethyl)amino]ethyl}amino)ethyl]-(carboxymethyl)amino}acetic acid, trifluoroacetic acid salt

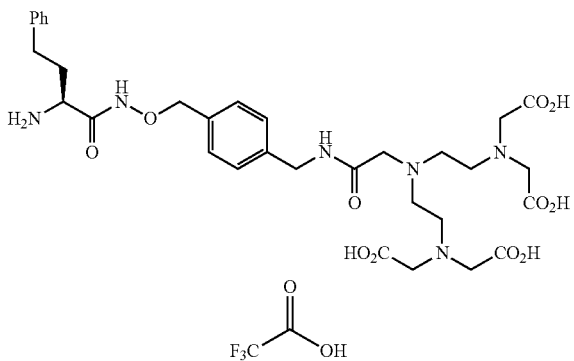

part A—Preparation of N-(1-(N-hydroxycarbamoyl)(1S)-3-phenylpropyl)(tert-butoxy)-carboxamide

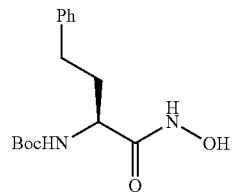 [SMILES: CC(C)(C)OC(=O)N[C@@H](CCc1ccccc1)C(=O)NO]

A suspension of H-Hfe-OH (1.79 g, 10.0 mmol) in 2:1 THF/H$_2$O (50.0 mL) was treated with Na$_2$CO$_3$ (2.54 g, 24.0 mmol) followed by Boc$_2$O (2.62 g, 12.0 mmol) in one portion at 22° C. After 1 h the heavy suspension was acidified to pH 3-4 using 0.1 M HCl, and the resulting homogeneous solution transferred to a separatory funnel and washed with EtOAc (4×50 mL). The combined EtOAc washes were dried over MgSO$_4$, filtered and concentrated in vacuo to a colorless oil that was used without further purification in subsequent reactions.

A solution of crude Boc-Hfe-OH (10.0 mmol theoretical) in 4:1 CH$_2$Cl$_2$/MeOH (50.0 mL) was treated with (trimethylsilyl)diazomethane (12.0 mmol; 6.00 mL of a 2.0 M solution in Et$_2$O) dropwise over 0.25 h at 22° C. CAUTION: vigorous gas evolution. The resulting yellow solution was stirred an additional 0.25 h to ensure complete methylation. Excess (trimethylsilyl)diazomethane was consumed by the dropwise addition of glacial AcOH, then all volatiles removed in vacuo. The crude ester was redissolved in MeOH (50.0 mL), cooled to 0° C. and treated with a previously prepared suspension of H$_2$NOH.HCl (2.08 g, 30.0 mmol) and KOH (3.37 g, 60.0 mmol) in MeOH (50.0 mL); a large bore cannula needle was required for the transfer. The resulting suspension then warmed slowly to 22° C. overnight as the ice bath melted. After 14 h, the suspension was acidified with conc. HCl to pH 4-5 then all volatiles removed in vacuo. The solids were triturated with several portions of hot EtOAc (5×10 mL) and removed by filtration through a scintered glass funnel of medium porosity. The combined filtrates were collected and concentrated in vacuo to an off-white powder. Purification through recrystallization from hot EtOAc (200 mL) afforded a white microcrystalline solid (1.47 g, 4.99 mmol, 49.9%). The spectral data obtained for this material are in accord with that described for the product of Part 1A.

part B—Preparation of (2S)-N-{[4-(aminomethyl)phenyl]methoxy}-2-[(tert-butoxy)carbonyl-amino]-4-phenylbutanamide, formic acid salt

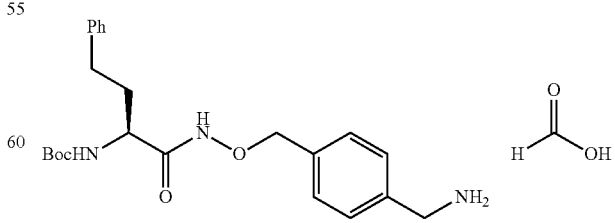

A solution of K$_2$CO$_3$ (0.207 g, 1.50 mmol) in H$_2$O (3.00 mL) was diluted with absolute EtOH (7.00 mL) then treated with the product of Part 3A (0.442 g, 1.50 mmol) in one portion at 22° C. Upon complete dissolution (10-15 min), the product of Part 1C (0.284 g, 1.00 mmol) was added in one portion and the resulting suspension stirred vigorously; a rapid stirring rate is required to ensure complete dissolution of the bromide. Within 25 min the solution turned cloudy and a heavy white precipitate formed; the reaction was complete at 1 h. The resulting suspension was then diluted with $H_2O$ (40 mL) and the solids collected on a scintered glass funnel of medium porosity. The solids were further washed with $H_2O$ and $Et_2O$ (5×20 mL each) then dried in vacuo to a white powder that was used without further purification in the subsequent deprotection step.

The hydroxamate ester (0.337 g, 0.677 mmol) was dissolved in 2:1 MeCN/$H_2O$ (6.77 mL) and successively treated with 15.4 mg TPPTS (27.1 μmol; 4 mol %), $Et_2NH$ (175 μL, 1.69 mmol) and 3.0 mg Pd(OAc)$_2$ (13.5 μmol; 2 mol %) at 22° C. Complete deprotection was observed within 1 h. The amber solution was diluted to 14 mL with $H_2O$ containing 0.1% $HCO_2H$, then filtered through a 0.45 μm Acrodisk and purified by HPLC on a Phenomenex Luna C18 column (21.2× 250 mm) using a 1%/min gradient from 10-50% MeCN containing 0.1% $HCO_2H$ and 10% $H_2O$ at 20 mL/min. The main product peak eluting at 17 min was collected and lyophilized to a white powder (0.229 g, 0.498 mmol; 49.8%). The spectral data obtained for this material are in accord with that described for the product of Part 1B.

part C—Preparation of 2-{[2-({[N-({4-[((2S)-2-amino-4-phenylbutanoylaminooxy)methyl]-phenyl}methyl)carbamoyl]methyl}{2-[bis(carboxymethyl)amino]ethyl}amino)ethyl]-(carboxymethyl)amino}acetic acid, trifluoroacetic acid salt

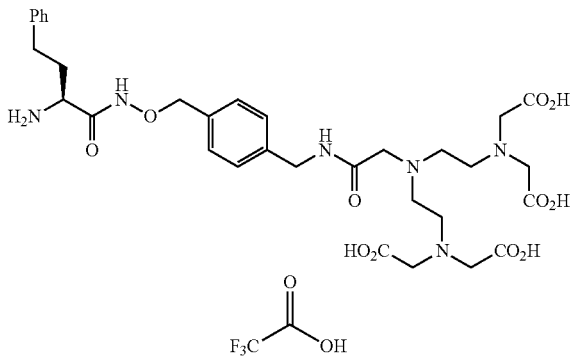

A solution of 2-{bis[2-(bis{[(tert-butyl)oxycarbonyl]methyl}amino)ethyl]amino}acetic acid (0.278 g, 0.450 mmol) in dry DMF (3.00 mL) was successively treated with HOBt (68.9 mg, 0.450 mmol), i-Pr$_2$NEt (131 μL, 0.750 mmol) and HBTU (0.171 g, 0.450 mmol) at 22° C. After 0.25 h, the solution was transferred to the product of Part 3B (0.138 g, 0.300 mmol) using a cannula. The resulting solution was stirred 0.5 h then partitioned between EtOAc and 0.1 M citric acid (50 mL each) with transfer to a separatory funnel. The layers separated and the aqueous layer washed with EtOAc (2×50 mL). The combined EtOAc layers were successively washed with 0.1 M citric acid and saturated aqueous solutions of NaHCO$_3$ and NaCl (3×50 mL each) then dried over MgSO$_4$, filtered and concentrated in vacuo to a colorless oil which was used without further purification in the subsequent deprotection step.

The protected conjugate (0.300 mmol theoretical) was dissolved in dioxane (3.00 mL) then successively treated with $H_2O$ (27 μL) and HCl (12.0 mmol; 3.00 mL of a 4 M solution in dioxane) at 22° C. The resulting pale yellow solution was stirred 15 h, during which time a heavy white precipitate formed. Upon complete deprotection, the volatiles were removed in vacuo and the white solid residue redissolved in $H_2O$ containing 0.1% TFA (8.00 mL) then directly purified by HPLC on a Phenomenex Luna C18 column (21.2×250 mm) using a 1%/min gradient from 0-40% MeCN containing 0.1% TFA and 10% $H_2O$ at 20 mL/min. The main product peak eluting at 25 min was collected and lyophilized to a white powder (0.181 g, 0.176 mmol; 58.5%). $^1$H NMR (DMSO-d$_6$, 600 MHz): δ 11.79 (1H, brs), 8.96 (1H, brt, J=5.9 Hz), 8.37 (3H, brs), 7.39 (2H, AB, J$_{AB}$=8.1 Hz), 7.32-7.29 (4H, m), 7.20 (1H, brdd, J=7.3, 7.3 Hz), 7.13 (2H, AB, J$_{AB}$=7.1 Hz), 4.84 (2H, AB, J$_{AB}$=11.8 Hz), 4.34 (2H, brd, J=5.8 Hz), 4.25 (2H, brs), 3.65 (1H, brs), 3.50 (8H, s), 3.38 (4H, brt, J=5.8 Hz), 3.05 (4H, brt, J=5.9 Hz), 2.54-2.50 (2H, m), 1.96-1.91 (2H, m). $^{13}$C NMR (DMSO-d$_6$, 151 MHz): δ 172.7, 165.3, 164.8, 158.1 (q, J=32.2 Hz), 140.2, 138.7, 134.3, 128.9, 128.5, 128.1, 127.3, 126.2, 116.9 (q, J=299 Hz), 76.9, 54.3, 53.9, 52.2, 50.2, 48.7, 42.1, 32.8, 30.3. HRMS calcd for $C_{32}H_{44}N_6O_{11}$ (M+H): 689.3141. Found: 689.3147. The optical purity of the product was established by chiral GLC analysis (99.0% L-homophenylalanine).

EXAMPLE 4

2-({2-[({N-[6-((2R)-2-amino-4-methylpentanoylaminooxy)hexyl]carbamoyl}methyl){2-[bis(carboxymethyl)amino]ethyl}amino]ethyl}(carboxymethyl)amino)acetic acid, trifluoroacetic acid salt

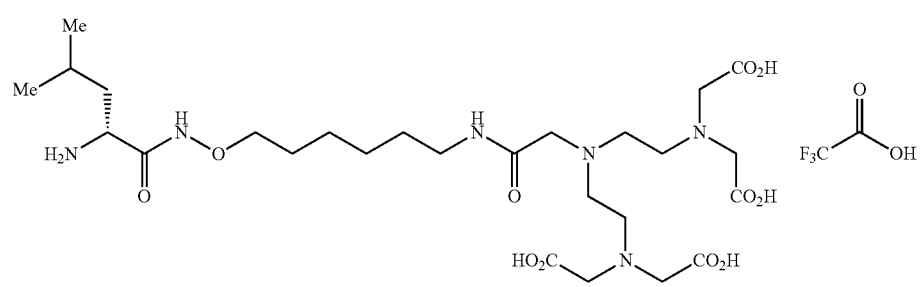 [SMILES: CC(C)C[C@@H](N)C(=O)NOCCCCCCNC(=O)CN(CCN(CC(=O)O)CC(=O)O)CCN(CC(=O)O)CC(=O)O ; O=C(O)C(F)(F)F]

part A—Preparation of 6-(Prop-2-enyloxycarbonylamino)hexyl methylsulfonate

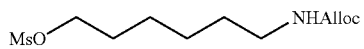

A solution of N-(6-hydroxyhexyl)prop-2-enyloxycarboxamide (2.55 g, 12.7 mmol; Charreyre, M. T.; Boullanger, P.; Pichot, C.; Delair, T.; Mandrand, B.; Llauro, M. F. *Mak. Chem.* 1993, 194(1), 117-35.) in dry $CH_2Cl_2$ (30.0 mL) was treated with $Et_3N$ (4.06 mL, 29.1 mmol) then cooled to 0° C. To this solution was transferred MsCl (15.2 mmol; 20.0 mL of a 0.76 M solution in $CH_2Cl_2$) using a cannula; full conversion coincided with completion of the transfer. The resulting solution was warmed to 22° C., then treated with 2 M $NH_4Cl$ (50 mL) and transferred to a separatory funnel. The layers separated and the aqueous layer washed with $CH_2Cl_2$ (3×50 mL). The combined washes were washed with 20% aqueous NaCl then dried over $MgSO_4$, filtered and concentrated in vacuo to a pale yellow oil (3.2 g) that was used without further purification in the subsequent alkylation step. $^1H$ NMR ($CDCl_3$, 300 MHz): δ 5.90 (1H, ddt, J=17.2, 10.4, 5.6 Hz), 5.29 (1H, dq, J=17.2, 1.6 Hz), 5.19 (1H, dq, J=10.4, 1.3 Hz), 4.71 (1H, brs), 4.54 (2H, brd, J=5.5 Hz), 4.20 (2H, t, J=6.5 Hz), 3.17 (2H, brs), 2.98 (3H, s), 1.79-1.69 (2H, m), 1.55-1.29 (6H, m).

part B—Preparation of N-{6-[(tert-butoxy)carbonylaminooxy]hexyl}prop-2-enyloxycarboxamide

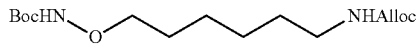

A solution of N-Boc hydroxylamine (2.37 g, 17.8 mmol) in anhydrous $Et_2O$ (5.00 mL) was treated with DBU (2.85 mL, 19.1 mmol) then cooled to 0° C. To this mixture was transferred the product of Part 4A (12.7 mmol; 5.00 mL of a 2.53 M solution in $Et_2O$) by means of a cannula. The resulting solution then warmed slowly to 22° C. overnight as the ice bath melted. After 17 h the $Et_2O$ was removed under a stream of $N_2$, and the resulting thick oil stirred 16 h to ensure complete conversion. After this time, the solution was diluted with $Et_2O$ (20 mL), transferred to a separatory funnel then successively washed with 2 M $NH_4Cl$ (30 mL) and 20% aqueous NaCl (2×30 mL). The resulting $Et_2O$ solution was dried over $MgSO_4$, filtered and concentrated in vacuo to a pale yellow oil that was purified by chromatography on silica (3:1 hexanes/EtOAc; $R_f$=0.5 in 2:1 hexanes/EtOAc) to afford a colorless oil (2.61 g, 8.25 mmol; 65.1%). $^1H$ NMR ($CDCl_3$, 600 MHz): δ 7.14 (1H, brs), 5.91 (1H, ddt, J=17.2, 10.5, 5.7 Hz), 5.29 (1H, dq, J=17.2, 1.6 Hz), 5.19 (1H, dq, J=10.5, 1.4 Hz), 4.77 (1H, brs), 4.55 (2H, brd, J=5.0 Hz), 3.83 (2H, t, J=6.5 Hz), 3.17 (2H, dt, J=6.7, 6.4 Hz), 1.63-1.59 (2H, m), 1.52-1.47 (2H, m), 1.47 (9H, s), 1.42-1.31 (4H, m)

part C—Preparation of N-[6-(aminooxy)hexyl]prop-2-enyloxycarboxamide, hydrochloric acid salt

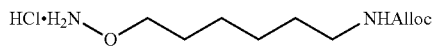

The product of Part 4B (2.61 g, 8.25 mmol) was treated with HCl (16.0 mmol; 8.00 mL of a 2 M solution in $Et_2O$), and the resulting solution stirred 5 h at 22° C. The heavy white precipitate that formed was collected on a scintered glass funnel, then washed with $Et_2O$ (3×8 mL) and dried to constant weight in vacuo (1.02 g, 4.04 mmol; 48.9%). The resulting material required no additional purification. $^1H$ NMR (DMSO-$d_6$, 600 MHz): δ 10.95 (3H, brs), 7.15 (1H, brt, J=5.5 Hz), 5.89 (1H, ddt, J=17.2, 10.5, 5.2 Hz), 5.25 (1H, dq, J=17.2, 1.8 Hz), 5.15 (1H, dq, J=10.5, 1.6 Hz), 4.43 (2H, brd, J=5.5 Hz), 3.98 (2H, t, J=6.5 Hz), 2.97-2.93 (2H, m), 1.57-1.53 (2H, m), 1.38 (2H, tt, J=7.1, 7.1 Hz), 1.31-1.22 (4H, m). $^{13}C$ NMR (DMSO-$d_6$, 151 MHz): δ 155.8, 133.8, 116.7, 73.9, 64.0, 40.0, 29.2, 27.0, 25.7, 24.7. HRMS calcd for $C_{10}H_{20}N_2O_3$ (M+Na): 239.1366. Found: 239.1363.

part D—Preparation of (2R)-N-(6-aminohexyloxy)-2-[(tert-butoxy)carbonylamino]-4-methylpentanamide, trifluoroacetic acid salt

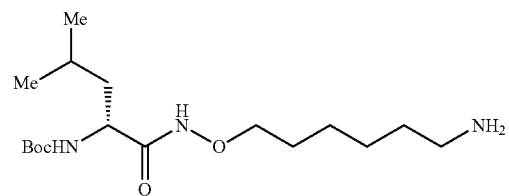

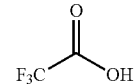

A solution of Boc-DLeu-OH (0.231 g, 1.00 mmol) in MeCN (4.00 mL) was successively treated with HOBt (0.153 g, 1.00 mmol), i-$Pr_2NEt$ (174 μL, 1.00 mmol) and HBTU (0.379 g, 1.00 mmol) at 22° C. After 0.25 h, the solution was treated with the product of Part 4C (0.210 g, 0.831 mmol) in one portion. The resulting solution was stirred 1 h then partitioned between $CH_2Cl_2$ and 0.1 M citric acid (50 mL each) with transfer to a separatory funnel. The layers separated and the $CH_2Cl_2$ solution successively washed with 0.1 M citric acid (2×50 mL) and saturated aqueous solutions of $NaHCO_3$ (3×50 mL) and NaCl (50 mL) then dried over $MgSO_4$, filtered and concentrated in vacuo to a colorless oil which was used without further purification in the subsequent deprotection step.

The crude hydroxamate ester (0.831 mmol theoretical) was dissolved in 2:1 MeCN/$H_2O$ (3.00 mL) and successively treated with 18.9 mg TPPTS (33.2 μmol; 4 μmol %), $Et_2NH$ (216 μL, 2.09 mmol) and 3.7 mg Pd(OAc)$_2$ (16.5 μmol; 2 mol %) at 22° C. Complete deprotection was observed within 0.5 h. The amber solution was filtered through a 0.45 μm Acrodisk then directly purified by HPLC on a Phenomenex Luna C18 column (21.2×250 mm) using a 1%/min gradient from 0-40% MeCN containing 0.1% TFA and 10% $H_2O$ at 20 mL/min. The main product peak eluting at 34 min was collected and lyophilized to a white powder (0.190 g, 0.413 mmol; 49.8%).

part E—Preparation of 2-({2-[({N-[6-((2R)-2-amino-4-methylpentanoylaminooxy)-hexyl]carbamoyl}methyl){2-[bis(carboxymethyl)amino]ethyl}amino]ethyl}(carboxymethyl)-amino)acetic acid, trifluoroacetic acid salt

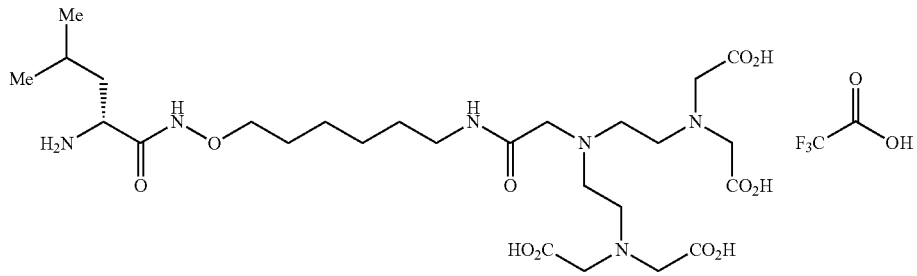 [SMILES: CC(C)C[C@@H](N)C(=O)NOCCCCCCNC(=O)CN(CCN(CC(=O)O)CC(=O)O)CCN(CC(=O)O)CC(=O)O ; O=C(O)C(F)(F)F]

A solution of 2-{bis[2-(bis{[(tert-butyl)oxycarbonyl]methyl}amino)ethyl]amino}acetic acid (74.0 mg, 0.120 mmol) in dry DMF (1.00 mL) was successively treated with HOBt (18.4 mg, 0.120 mmol), i-Pr$_2$NEt (35 μL, 0.20 mmol) and HBTU (45.5 mg, 0.120 mmol) at 22° C. After 0.25 h, the solution was treated with the product of Part 4D (46.0 mg, 0.100 mmol) in one portion.

The resulting solution was stirred 0.5 h then diluted with EtOAc (50 mL), washed with 0.1 M citric acid (3×30 mL), 0.1 M NaOH (3×30 mL) and saturated aqueous and NaCl (30 mL) then dried over MgSO$_4$, filtered and concentrated in vacuo to a colorless oil which was used without further purification in the subsequent deprotection step.

The protected conjugate (0.100 mmol theoretical) was dissolved in dioxane (0.500 mL) then successively treated with H$_2$O (2 μL) and HCl (2.00 mmol; 0.500 mL of a 4 M solution in dioxane) at 22° C. The resulting pale yellow solution was stirred 15 h, during which time a heavy white precipitate formed. Upon complete deprotection, the volatiles were removed under a stream of N$_2$ and the white solid residue directly purified by HPLC on a Phenomenex Luna C18 column (21.2×250 mm) using a 1%/min gradient from 0-40% MeCN containing 0.1% TFA and 10% H$_2$O at 20 mL/min. The main product peak eluting at 20 min was collected and lyophilized to a white powder (52.0 mg, 0.054 mmol; 54.0%). $^1$H NMR (DMSO-d$_6$, 600 MHz): δ 11.68 (1H, brs), 8.43 (1H, brt, J=5.5 Hz), 8.26 (2H, brs), 4.13 (2H, s), 3.79 (2H, t, J=6.6 Hz), 3.53 (1H, brs), 3.49 (8H, s), 3.34 (4H, brt, J=5.5 Hz), 3.11 (2H, td, J=6.9, 5.7 Hz), 3.03 (4H, brt, J=5.9 Hz), 1.60-1.50 (5H, m), 1.43 (2H, tt, J=7.2, 7.2 Hz), 1.36-1.26 (4H, m), 0.89 (3H, d, J=6.3 Hz), 0.87 (3H, d, J=6.0 Hz). $^{13}$C NMR (DMSO-d$_6$, 151 MHz): δ 172.7, 165.4, 164.4, 157.9 (q, J=31.8 Hz), 117.1 (q, J=300 Hz), 75.3, 54.3, 53.9, 52.1, 48.9, 48.6, 40.0, 38.7, 28.7, 27.4, 26.1, 24.9, 23.7, 22.2, 22.0. HRMS calcd for C$_{26}$H$_{48}$N$_6$O$_{11}$ (M+H): 621.3454. Found: 621.3462.

EXAMPLE 5

2-[(2-{[(N-{6-[(2R)-2-amino-3-(4-phenylphenyl)propanoylaminooxy]hexyl}carbamoyl)methyl]{2-[bis(carboxymethyl)amino]ethyl}amino}ethyl)(carboxymethyl)amino]acetic acid, trifluoroacetic acid salt

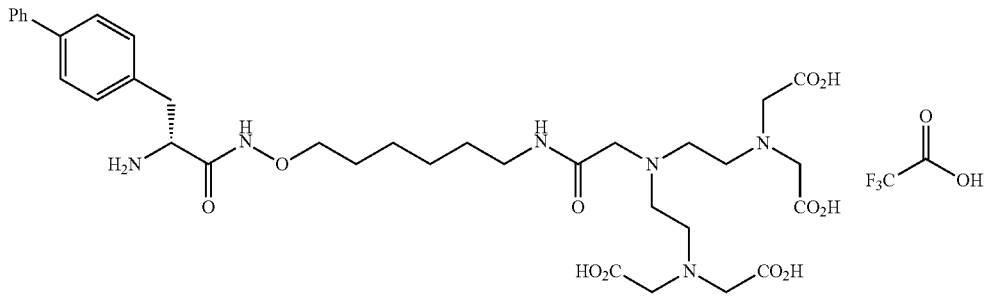 [SMILES: N[C@H](Cc1ccc(-c2ccccc2)cc1)C(=O)NOCCCCCCNC(=O)CN(CCN(CC(=O)O)CC(=O)O)CCN(CC(=O)O)CC(=O)O ; O=C(O)C(F)(F)F]

part A—Preparation of (2R)-N-(6-aminohexyloxy)-2-[(tert-butoxy)carbonylamino]-3-(4-phenylphenyl)propanamide, trifluoroacetic acid salt

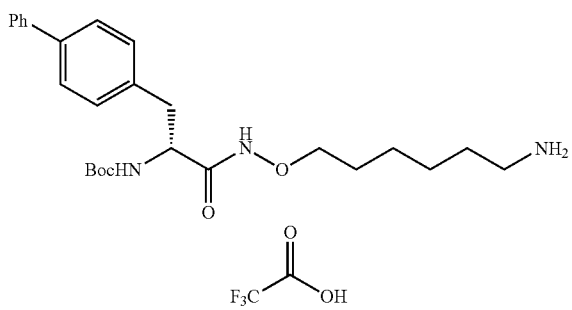

A solution of Boc-DBip-OH (0.231 g, 1.00 mmol) in MeCN (4.00 mL) was successively treated with HOBt (0.153 g, 1.00 mmol), i-Pr$_2$NEt (174 µL, 1.00 mmol) and HBTU (0.379 g, 1.00 mmol) at 22° C. After 0.25 h, the solution was treated with the product of Part 4C (0.210 g, 0.831 mmol) in one portion. The resulting solution was stirred 1 h then partitioned between EtOAc and 0.1 M citric acid (50 mL each) with transfer to a separatory funnel. The layers separated and the EtOAc solution successively washed with 0.1 M citric acid (2×50 mL) and saturated aqueous solutions of NaHCO$_3$ (3×50 mL) and NaCl (50 mL) then dried over MgSO$_4$, filtered and concentrated in vacuo to a white solid which was used without further purification in the subsequent deprotection step.

The crude hydroxamate ester (0.831 mmol theoretical) was dissolved in 2:1 MeCN/H$_2$O (3.00 mL) and successively treated with 18.9 mg TPPTS (33.2 µmol; 4 mol %), Et$_2$NH (216 µL, 2.09 mmol) and 3.7 mg Pd(OAc)$_2$ (16.5 µmol; 2 mol %) at 22° C. Complete deprotection was observed within 0.5 h. The amber solution was filtered through a 0.45 µm Acrodisk then directly purified by HPLC on a Phenomenex Luna C18 column (21.2×250 mm) using a 1%/min gradient from 10-50% MeCN containing 0.1% TFA and 10% H$_2$O at 20 mL/min. The main product peak eluting at 35 min was collected and lyophilized to a white powder (0.140 g, 0.246 mmol; 29.6%). $^1$H NMR (DMSO-d$_6$, 600 MHz): δ 11.06 (1H, brs), 7.70-7.60 (4H, m), 7.56 (2H, AB, J$_{AB}$=8.0 Hz), 7.44 (2H, dd, J=8.0, 7.4 Hz), 7.33 (1H, brt, J=7.4 Hz), 7.31 (2H, AB, J$_{AB}$=8.0 Hz), 7.06 (1H, brd, J=8.2 Hz), 4.02-3.99 (1H, m), 3.68-3.59 (2H, m), 2.88 (2H, ABX, J$_{AB}$=13.5 Hz, J$_{AX}$=6.1 Hz, J$_{BX}$=9.3 Hz), 2.73 (2H, brs), 1.52-1.42 (4H, m), 1.31 (9H, s), 1.30-1.25 (4H, m).

part B—Preparation of 2-[(2-{[(N-{6-[(2R)-2-amino-3-(4-phenylphenyl)propanoylaminooxy]-hexyl}carbamoyl)methyl]{2-[bis(carboxymethyl)amino]ethyl}amino}ethyl)(carboxymethyl)-amino]acetic acid, trifluoroacetic acid salt A solution of 2-{bis[2-(bis{[(tert-butyl)oxycarbonyl]methyl}amino)ethyl]amino}acetic acid (74.0 mg, 0.120 mmol) in dry DMF (1.00 mL) was successively treated with HOBt (18.4 mg, 0.120 mmol), i-Pr$_2$NEt (35 µL, 0.20 mmol) and HBTU (45.5 mg, 0.120 mmol) at 22° C. After 0.25 h, the solution was treated with the product of Part 5A (57.0 mg, 0.100 mmol) in one portion. The resulting solution was stirred 0.5 h then diluted with EtOAc (50 mL), washed with 0.1 M citric acid (3×30 mL), 0.1 M NaOH (3×30 mL) and saturated aqueous and NaCl (30 mL) then dried over MgSO$_4$, filtered and concentrated in vacuo to a colorless oil which was used without further purification in the subsequent deprotection step.

The protected conjugate (0.100 mmol theoretical) was dissolved in dioxane (0.500 mL) then successively treated with H$_2$O (2 µL) and HCl (2.00 mmol; 0.500 mL of a 4 M solution in dioxane) at 22° C. The resulting pale yellow solution was stirred 15 h, during which time a heavy white precipitate formed. Upon complete deprotection, the volatiles were removed under a stream of N$_2$ and the white solid residue directly purified by HPLC on a Phenomenex Luna C18 column (21.2×250 mm) using a 1%/min gradient from 10-40% MeCN containing 0.1% TFA and 10% H$_2$O at 20 mL/min. The main product peak eluting at 10 min was collected and lyophilized to a white powder (35.0 mg, 32.6 mmol; 32.6%). $^1$H NMR (DMSO-d$_6$, 600 MHz): δ 11.47 (1H, brs), 8.43 (2H, brs), 8.40 (1H, brd, J=5.5 Hz), 7.64-7.63 (4H, m), 7.47-7.44 (2H, m), 7.37-7.34 (1H, m), 7.30 (2H, AB, J$_{AB}$=7.8 Hz), 4.13 (2H, s), 3.79 (1H, brs), 3.63 (1H, ABX, J$_{AB}$=9.7 Hz, J$_{AX}$=6.8 Hz), 3.53 (1H, ABX, J$_{AB}$=9.7 Hz, J$_{BX}$=6.6 Hz), 3.49 (8H, s), 3.45 (4H, brt, J=5.8 Hz), 3.09-2.99 (4H, m), 3.03 (4H, brt, J=6.0 Hz), 1.37-1.32 (4H, m), 1.23-1.16 (4H, m). $^{13}$C NMR (DMSO-d$_6$, 151 MHz): δ 172.7, 164.3, 164.2, 157.9 (q, J=31.8 Hz), 139.6, 139.0, 133.9, 130.0, 128.9, 127.4, 126.7, 126.4, 116.9 (q, J=299 Hz), 75.3, 54.3, 53.8, 52.1, 51.5, 48.6, 38.7, 36.5, 28.6, 27.3, 26.0, 24.8. HRMS calcd for C$_{35}$H$_{50}$N$_6$O$_{11}$ (M+H): 731.3610. Found: 731.3612.

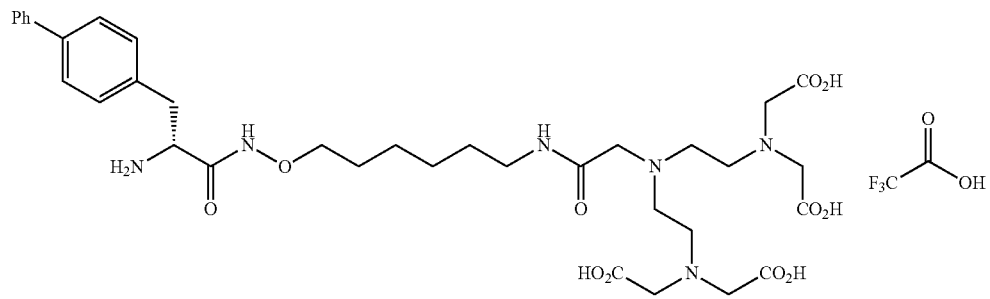 [SMILES: N[C@H](Cc1ccc(-c2ccccc2)cc1)C(=O)NOCCCCCCNC(=O)CN(CCN(CC(=O)O)CC(=O)O)CCN(CC(=O)O)CC(=O)O ; O=C(O)C(F)(F)F]

EXAMPLE 6

2-({2-[({N-[6-((2R)-2-amino-3-cyclohexylpropanoylaminooxy)hexyl]carbamoyl}methyl) {2-[bis(carboxymethyl)amino]ethyl}amino]ethyl}(carboxymethyl)amino)acetic acid, trifluoroacetic acid salt

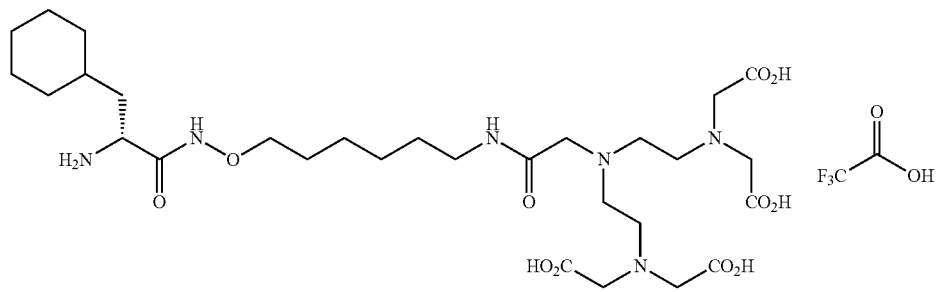 [SMILES: N[C@H](CC1CCCCC1)C(=O)NOCCCCCCNC(=O)CN(CCN(CC(=O)O)CC(=O)O)CCN(CC(=O)O)CC(=O)O ; O=C(O)C(F)(F)F]

part A—Preparation of (2R)-N-(6-aminohexyloxy)-2-[(tert-butoxy)carbonylamino]-3-cyclohexylpropanamide, trifluoroacetic acid salt

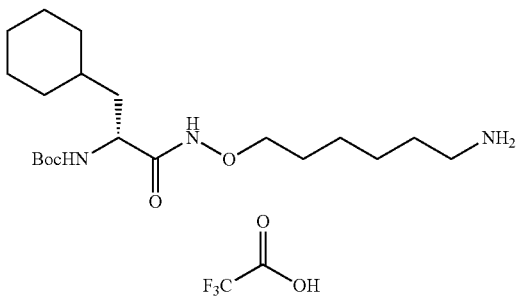

A solution of Boc-DCha-OH (0.163 g, 0.360 mmol) in $CH_2Cl_2$ (3.00 mL) was successively treated with HOBt (55.1 mg, 0.360 mmol), i-$Pr_2$NEt (125 μL, 0.720 mmol) and HBTU (0.137 g, 0.360 mmol) at 22° C. After 0.25 h, the solution was treated with the product of Part 4C (75.8 mg, 0.300 mmol) in one portion. The resulting solution was stirred 1 h then all volatiles removed in vacuo. The crude hydroxamate ester was redissolved in 2:1 MeCN/$H_2O$ (3.00 mL) and successively treated with 17.1 mg TPPTS (30.0 μmol; 10 mol %), $Et_2$NH (78 μL, 0.75 mmol) and 3.4 mg Pd(OAc)$_2$ (15 μmol; 5 mol %) at 22° C. Complete deprotection was observed within 1 h. The resulting yellow solution was diluted with $H_2O$ containing 0.1% TFA (5.00 mL) then filtered through a 0.45 m Acrodisk and directly purified by HPLC on a Phenomenex Luna C18 column (21.2×250 mm) using a 1%/min gradient from 10-50% MeCN containing 0.1% TFA and 10% $H_2O$ at 20 mL/min. The main product peak eluting at 38 min was collected and lyophilized to a white powder (77.7 mg, 0.156 mmol; 51.8%). A small amount of TPPTS can be detected in the $^1H$ NMR spectrum. $^1H$ NMR (DMSO-$d_6$, 600 MHz): δ 11.04 (1H, brs), 7.71 (3H, brs), 6.84 (1H, brd, J=8.1 Hz), 3.83-3.80 (1H, m), 3.73-3.67 (2H, m), 2.79-2.73 (2H, m), 1.87-1.45 (9H, m), 1.42-1.27 (5H, m), 1.36 (9H, s), 1.25-1.07 (4H, m), 0.87-0.78 (2H, m). $^{13}C$ NMR (DMSO-$d_6$, 151 MHz): δ 169.1, 158.0 (q, J=31.8 Hz), 155.1, 117.0 (q, J=300 Hz), 77.9, 74.7, 49.7, 38.7, 33.5, 32.8, 32.0, 28.1, 27.4, 26.8, 26.0, 25.8, 25.6, 25.5, 24.8. HRMS calcd for $C_{20}H_{39}N_3O_4$ (M+H): 386.3013. Found: 386.3016.

part B—Preparation of 2-({2-[({N-[6-((2R)-2-amino-3-cyclohexylpropanoylaminooxy)hexyl]carbamoyl}methyl) {2-[bis(carboxymethyl)amino]ethyl}amino]ethyl}(carboxymethyl)-amino)acetic acid, trifluoroacetic acid salt

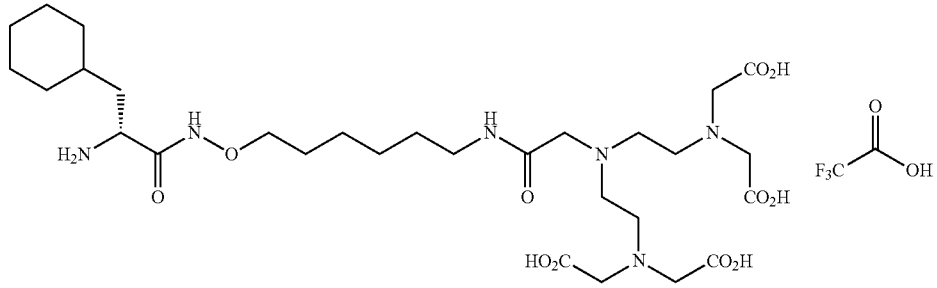 [SMILES: N[C@H](CC1CCCCC1)C(=O)NOCCCCCCNC(=O)CN(CCN(CC(=O)O)CC(=O)O)CCN(CC(=O)O)CC(=O)O ; O=C(O)C(F)(F)F]

A solution of 2-{bis[2-(bis{[(tert-butyl)oxycarbonyl]methyl}amino)ethyl]amino}acetic acid (18.5 mg, 30.0 μmol), HOBt (4.6 mg, 30.0 μmol) and the product of Part 6A (12.5 mg, 25.0 μmol) in dry DMF (1.00 mL) was successively treated with i-$Pr_2$NEt (10 μL, 6 μmol) and HBTU (11.4 mg, 30.0 mol) at 22° C. The resulting solution was stirred 0.25 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (25.0 μmol theoretical) was dissolved in dioxane (0.500 mL) then successively treated with H$_2$O (3 μL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed in vacuo and the white solid residue redissolved in H$_2$O containing 0.1% TFA (8.20 mL) then directly purified by HPLC on a Phenomenex Luna C18 column (21.2×250 mm) using a 1%/min gradient from 0-40% MeCN containing 0.1% TFA and 10% H$_2$O at 20 mL/min. The main product peak eluting at 28 min was collected and lyophilized to a white powder (7.3 mg, 7.3 μmol; 29%). $^1$H NMR (DMSO-d$_6$, 600 MHz): δ 11.60 (1H, brs), 8.40 (1H, brs), 8.19 (3H, brs), 4.11 (2H, brs), 3.81-3.76 (2H, m), 3.55 (1H, brs), 3.49 (8H, s), 3.33 (4H, brs), 3.11 (2H, td, J=7.0, 6.0 Hz), 3.02 (4H, brt, J=5.8 Hz), 1.72 (1H, brd, J=13.1 Hz), 1.67-1.49 (8H, m), 1.43 (2H, tt, J=7.6, 7.1 Hz), 1.37-1.24 (5H, m), 1.19-1.10 (3H, m). $^{13}$C NMR (DMSO-d$_6$, 151 MHz): δ 172.7, 165.4, 157.7 (q, J=30.7 Hz), 117.2 (q, J=300 Hz), 75.3, 54.3, 53.8, 52.1, 48.7, 48.4, 40.0, 38.7, 38.4, 32.8, 32.3, 32.2, 28.7, 27.4, 26.1, 25.7, 25.5, 25.4, 24.9. HRMS calcd for C$_{29}$H$_{52}$N$_6$O$_{11}$ (M+H): 661.3767. Found: 661.3766.

EXAMPLE 7

2-{[2-({[N-({4-[3-((2R)-2-amino-3-indol-3-ylpropanoylaminooxy)propyl]phenyl}methyl)carbamoyl]methyl}{2-[bis(carboxymethyl)amino]ethyl}amino)ethyl](carboxymethyl)amino}acetic acid, trifluoroacetic acid salt mmol) in 2:1 MeOH/28% aqueous NH$_3$ (300 mL) then treated with Raney Ni (5.00 g) in one portion at 22° C. The resulting suspension was sparged with H$_2$ then pressurized to 50 psi and maintained 5 h; ~2 equiv H$_2$ were consumed at this point. The vessel was then purged with N$_2$ and charged with additional Raney Ni (2.5 g). The H$_2$ atmosphere was reestablished, and maintained until gas uptake ceased; ~135 psi total consumption. The vessel was purged with N$_2$ and the catalyst removed by filtration through Celite. The filter cake was exhaustively washed with 1:1 MeOH/H$_2$O (4×50 mL) and the combined filtrates concentrated in vacuo to a white solid.

The crude amino acid (25.0 mmol theoretical) was suspended in anhydrous THF (250 mL) then treated with i-Pr$_2$NEt (5.23 mL, 30.0 mmol). Allyl chloroformate (3.19 mL, 30.0 mmol) was then added over 10 min and the resulting suspension stirred 1.5 h at 22° C. The now homogeneous solution was treated with 0.1 M HCl (250 mL) then diluted with EtOAc (100 mL) with transfer to a separatory funnel. The layers separated and the aqueous layer washed with EtOAc (2×100 mL). The combined EtOAc layers were dried over MgSO$_4$, filtered and concentrated in vacuo to a colorless oil that was purified by chromatography on silica (40×280 mm) using 95:5 CH$_2$Cl$_2$/MeOH (R$_f$=0.4). The main product eluted between 320-420 mL, was collected and concentrated to afford a white powder (2.93 g, 11.1 mmol; 44.5%). Mp 109.5-110.5° C. $^1$H NMR (CDCl$_3$, 600 MHz): δ 7.20 (2H, AB, J$_{AB}$=7.7 Hz), 7.16 (2H, AB, J$_{AB}$=8.0 Hz), 5.91 (1H, ddt, J=17.0, 10.7, 5.5 Hz), 5.29 (1H, brd, J=17.0 Hz), 5.20 (1H, d, J=10.2 Hz), 5.11 (1H, brs), 4.58 (2H, brd, J=4.5 Hz), 4.32 (2H, brd, J=5.7 Hz), 2.93 (2H, t, J=7.7 Hz), 2.64 (2H, t, J=7.7 Hz). $^{13}$C NMR (CDCl$_3$, 151 MHz): δ 178.2, 156.3, 139.5, 136.5, 132.8, 128.5, 127.7, 117.7, 65.7, 44.8, 35.5, 30.2. HRMS calcd for C$_{14}$H$_{17}$NO$_4$ (M+Na): 286.1050. Found: 286.1041.

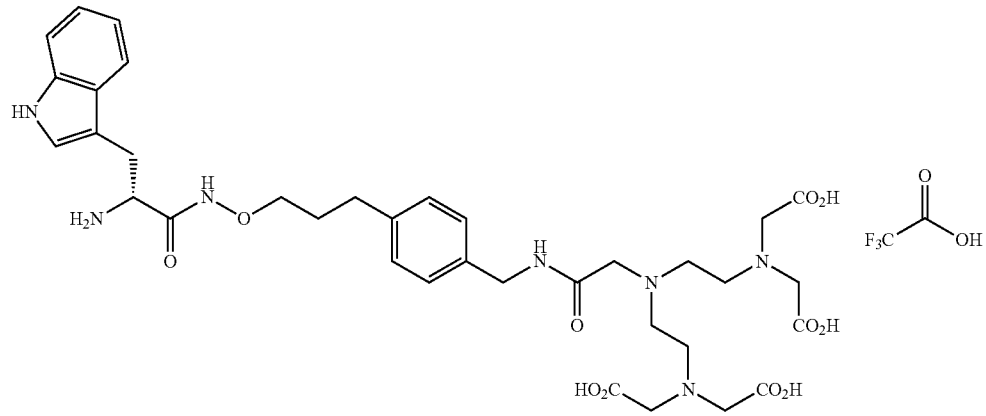 [SMILES: N[C@H](Cc1c[nH]c2ccccc12)C(=O)NOCCCc1ccc(CNC(=O)CN(CCN(CC(=O)O)CC(=O)O)CCN(CC(=O)O)CC(=O)O)cc1 ; O=C(O)C(F)(F)F]

part A—Preparation of 3-{4-[(Prop-2-enyloxycarbonylamino)methyl]phenyl}propanoic acid

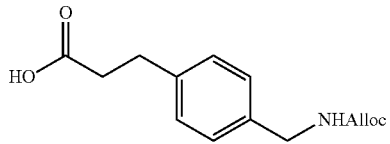

A 500 mL Parr bottle was charged with a solution of (2E)-3-(4-cyanophenyl)prop-2-enoic acid (4.33 g, 25.0 part B—Preparation of N-{[4-(3-hydroxypropyl)phenyl]methyl}prop-2-enyloxycarboxamide

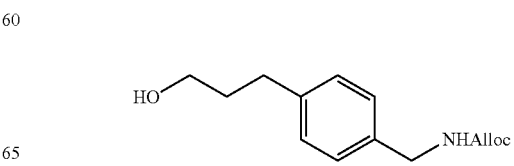

A solution of the product of Part 7A (1.32 g, 5.00 mmol) in dry THF (25.0 mL) was cooled to 0° C. and treated with LiAlH$_4$ (10.0 mmol; 10.0 mL of a 1 M solution in THF) dropwise over 20 min using a syringe pump. The suspension was stirred 0.5 h at 0° C. then warmed to 22° C. and maintained 2.5 h. After cooling to 0° C., excess LiAlH$_4$ was consumed by the careful addition of H$_2$O (400 µL) and the resulting white suspension successively treated with 15% aqueous NaOH (400 µL) and H$_2$O (1.20 mL) then stirred for 0.5 h to a fine white slurry. The solids were removed by filtration through Celite, washed with THF (5×20 mL) and the combined filtrates concentrated in vacuo. The crude oil was purified by chromatography on silica (40×260 mm) using 1:1 pentane/EtOAc (R$_f$=0.2). The main product eluted between 600-800 mL, was collected and concentrated to afford a white crystalline solid (0.795 g, 3.19 mmol; 63.8%). Mp 51.5-53.5° C. $^1$H NMR (CDCl$_3$, 600 MHz): δ 7.18 (2H, AB, J$_{AB}$=7.9 Hz), 7.14 (2H, AB, J$_{AB}$=8.2 Hz), 5.90 (1H, ddt, J=17.2, 10.4, 5.7 Hz), 5.28 (1H, brd, J=17.0 Hz), 5.19 (1H, dq, J=10.5, 1.2 Hz), 4.57 (2H, brd, J=4.9 Hz), 4.31 (2H, brd, J=5.8 Hz), 3.63 (2H, t, J=6.4 Hz), 2.66 (2H, dd, J=7.7, 7.7 Hz), 1.87-1.82 (3H, m). $^{13}$C NMR (CDCl$_3$, 151 MHz): δ 156.3, 141.1, 135.9, 132.8, 128.6, 127.5, 117.6, 65.6, 62.0, 44.7, 34.1, 31.6. HRMS calcd for C$_{14}$H$_{19}$NO$_3$ (M+Na): 272.1257. Found: 272.1263.

part C—Preparation of N-({4-[3-(aminooxy)propyl]phenyl}methyl)prop-2-enyloxycarboxamide, hydrochloric acid salt

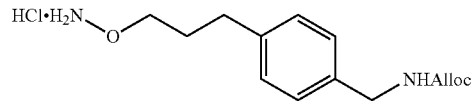

A solution of the product of Part 7B (1.25 g, 5.00 mmol), 2-hydroxyisoindoline-1,3-dione (0.979 g, 6.00 mmol) and PPh$_3$ (1.64 g, 6.25 mmol) in dry THF (50.0 mL) was cooled to 0° C. and treated with DEAD (0.236 mL, 1.50 mmol) dropwise such that the orange color did not persist. The solution was then warmed to 22° C. and treated with the remaining DEAD (0.709 mL, 4.50 mmol) dropwise over 0.75 h. The pale yellow solution thus obtained was concentrated in vacuo and directly purified by chromatography on silica using a gradient elution from 3:2→1:1 pentane/EtOAc (R$_f$=0.5 in 1:1 pentane EtOAc). The product containing fractions were combined and concentrated to a white crystalline solid that was further purified by recrystallization from EtOAc/pentane to afford fine colorless needles (1.37 g). Despite these efforts the material remained contaminated with ethoxy-N-(ethoxycarbonylamino)carboxamide and was therefore used directly in the subsequent deprotection step.

The crude phthalimide (1.18 g) was dissolved in 9:1 CHCl$_3$/MeOH (30.0 mL) then treated with hydrazine (0.530 mL, 9.00 mmol) in one portion at 22° C. Within 5 min a white precipitate formed; after 0.25 h the reaction was complete. The suspension was concentrated in vacuo and the resulting solid material triturated with Et$_2$O (5×20 mL) then removed by filtration through a scintered glass funnel. The filtrate was then treated with HCl (8.00 mmol; 2.00 mL of a 4 M solution in dioxane) and the resulting precipitate collected. The crystalline material was further washed with H$_2$O and Et$_2$O (3×30 mL each) then dried to constant weight in vacuo (0.345 g, 1.15 mmol; 95.3%). Mp 187° C. (dec). $^1$H NMR (DMSO-d$_6$, 600 MHz): δ 11.03 (2H, brs), 7.72 (1H, brt, J=5.8 Hz), 7.16 (4H, s), 5.90 (1H, dddd, J=17.0, 10.6, 5.4, 5.1 Hz), 5.27 (1H, brdd, J=17.2, 1.3 Hz), 5.16 (1H, brd, J=10.2 Hz), 4.47 (2H, dt, J=5.1, 1.5 Hz), 4.14 (2H, d, J=6.1 Hz), 4.00 (2H, t, J=6.5 Hz), 2.61-2.58 (2H, m), 1.89-1.84 (2H, m). $^{13}$C NMR (DMSO-d$_6$, 151 MHz): δ 156.1, 139.4, 137.4, 133.7, 128.2, 127.0, 116.9, 73.4, 64.2, 43.4, 30.6, 28.9. HRMS calcd for C$_{14}$H$_{20}$N$_2$O$_3$ (M+H): 265.1547. Found: 265.1550.

part D—Preparation of (2R)-N-{3-[4-(aminomethyl)phenyl]propoxy}-2-[(tert-butoxy)-carbonylamino]-3-indol-3-ylpropanamide, trifluoroacetic acid salt

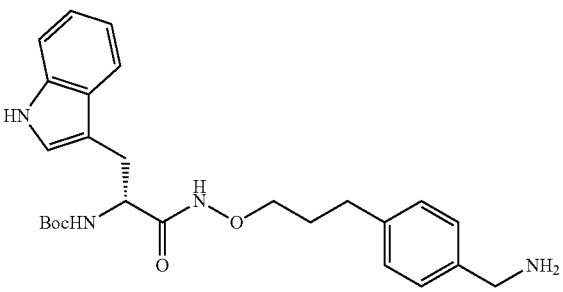

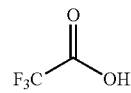

A solution of Boc-DTrp-OH (0.110 g, 0.360 mmol) in CH$_2$Cl$_2$ (3.00 mL) was successively treated with HOBt (55.1 mg, 0.360 mmol), i-Pr$_2$NEt (125 µL, 0.720 mmol) and HBTU (0.137 g, 0.360 mmol) at 22° C. After 0.25 h, the solution was treated with the product of Part 7C (90.2 mg, 0.300 mmol) in one portion. The resulting solution was stirred 1 h then all volatiles removed in vacuo. The crude hydroxamate ester was redissolved in 2:1 MeCN/H$_2$O (3.00 mL) and successively treated with 17.1 mg TPPTS (30.0 µmol; 10 mol %), Et$_2$NH (78 µL, 0.75 mmol) and 3.4 mg Pd(OAc)$_2$ (15 µmol; 5 mol %) at 22° C. Complete deprotection was observed within 1 h. The resulting yellow solution was diluted with H$_2$O containing 0.1% TFA (5.00 mL) then filtered through a 0.45 µm Acrodisk and directly purified by HPLC on a Phenomenex Luna C18 column (21.2×250 mm) using a 1%/min gradient from 20-60% MeCN containing 0.1% TFA and 10% H$_2$O at 20 mL/min. The main product peak eluting at 25 min was collected and lyophilized to a white powder (28.7 mg, 49.4 µmol; 16.5%). $^1$H NMR (DMSO-d$_6$, 600 MHz): δ 11.10 (1H, brs), 10.81 (1H, brs), 8.13 (3H, brs), 7.57 (1H, d, J=7.7 Hz), 7.36 (2H, AB, J$_{AB}$=8.0 Hz), 7.32 (1H, d, J=8.0 Hz), 7.26 (2H, AB, J$_{AB}$=8.0 Hz), 7.13 (1H, brs), 7.06 (1H, ddd, J=7.2, 7.0, 0.8 Hz), 6.98 (1H, dd, J=7.5, 7.2 Hz), 6.93 (1H, brd, J=7.7 Hz), 4.02 (1H, td, J=8.0, 6.5 Hz), 4.01-3.98 (2H, m), 3.70-3.59 (2H, m), 3.00 (1H, ABX, J$_{AB}$=14.1 Hz, J$_{AX}$=6.1 Hz), 2.90 (1H, ABX, J$_{AB}$=14.5 Hz, J$_{BX}$=8.5 Hz), 2.66-2.60 (2H, m), 1.73 (2H, brs), 1.33 (9H, s). $^{13}$C NMR (DMSO-d$_6$, 151 MHz): δ 168.6, 155.0, 142.1, 136.0, 131.3, 128.8, 128.6, 127.2, 123.7, 120.8, 118.4, 118.1, 111.2, 109.8, 78.0, 74.0, 52.9, 42.1, 31.0, 29.3, 28.1, 27.6. HRMS calcd for C$_{26}$H$_{34}$N$_4$O$_4$ (M+H): 467.2653. Found: 467.2649.

part E—Preparation of 2-{[2-({[N-({4-[3-((2R)-2-amino-3-indol-3-ylpropanoylaminooxy)-propyl]phenyl}methyl)carbamoyl]methyl}{2-[bis(carboxymethyl)amino]ethyl}amino)-ethyl](carboxymethyl)amino}acetic acid, trifluoroacetic acid salt

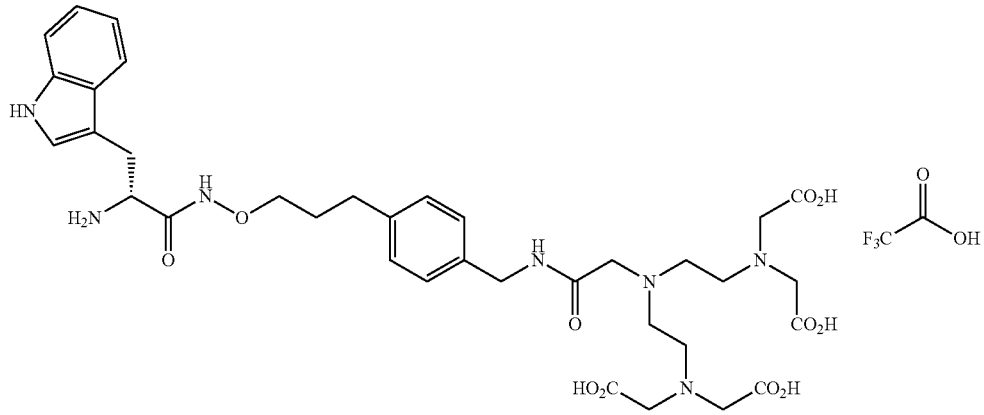 [SMILES: N[C@H](Cc1c[nH]c2ccccc12)C(=O)NOCCCc1ccc(CNC(=O)CN(CCN(CC(=O)O)CC(=O)O)CCN(CC(=O)O)CC(=O)O)cc1 ; O=C(O)C(F)(F)F]

A solution of 2-{bis[2-(bis{[(tert-butyl)oxycarbonyl]methyl}amino)ethyl]amino}acetic acid (18.5 mg, 30.0 μmol), HOBt (4.6 mg, 30.0 μmol) and the product of Part 7D (14.5 mg, 25.0 μmol) in dry DMF (1.00 mL) was successively treated with i-Pr$_2$NEt (10 μL, 6 μmol) and HBTU (11.4 mg, 30.0 mol) at 22° C. The resulting solution was stirred 0.25 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (25.0 μmol theoretical) was dissolved in dioxane (0.500 mL) then successively treated with H$_2$O (3 μL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed in vacuo and the white solid residue redissolved in H$_2$O containing 0.1% TFA (8.00 mL) then directly purified by HPLC on a Phenomenex Luna C18 column (21.2×250 mm) using a 1%/min gradient from 10-50% MeCN containing 0.1% TFA and 10% H$_2$O at 20 mL/min. The main product peak eluting at 19 min was collected and lyophilized to a white powder (3.4 mg, 3.1 μmol; 12.5%). $^1$H NMR (DMSO-d$_6$, 600 MHz): δ 11.50 (1H, brs), 11.01 (1H, brs), 8.87 (1H, brs), 8.26 (3H, brs), 7.59 (1H, d, J=7.8 Hz), 7.36 (1H, d, J=8.1 Hz), 7.19 (2H, AB, J$_{AB}$=8.1 Hz), 7.14 (2H, AB, J$_{AB}$=8.0 Hz), 7.09 (1H, dd, J=7.6, 7.4 Hz), 7.01 (1H, dd, J=7.5, 7.3 Hz), 6.50 (1H, brs), 4.31 (2H, brd, J=5.4 Hz), 4.19 (2H, brs), 3.73 (1H, brs), 3.64 (1H, ABXY, J$_{AB}$=9.6 Hz, J$_{AX}$=6.6 Hz, J$_{AY}$=6.4 Hz), 3.57 (1H, ABXY, J$_{AB}$=9.6 Hz, J$_{BX}$=6.4 Hz, J$_{BY}$=6.3 Hz), 3.49 (8H, s), 3.35 (4H, brs), 3.17 (1H, ABX, J$_{AB}$=14.3 Hz, J$_{AX}$=7.2 Hz), 3.09 (1H, ABX, J$_{AB}$=14.3 Hz, J$_{BX}$=6.8 Hz), 3.03 (4H, brt, J=5.2 Hz), 2.55 (2H, dd, J=7.7, 7.6 Hz), 1.70-1.63 (2H, m). $^{13}$C NMR (DMSO-d$_6$, 151 MHz): δ 172.7, 165.0, 157.7 (q, J=30.7 Hz), 140.2, 136.2, 135.7, 128.3, 127.4, 126.8, 124.6, 121.2, 118.5, 118.2, 117.2 (q, J=301 Hz), 111.5, 106.7, 74.6, 54.3, 53.9, 52.2, 51.0, 48.7, 42.1, 30.8, 29.1, 27.2. HRMS calcd for C$_{35}$H$_{47}$N$_7$O$_{11}$ (M+H): 742.3406. Found: 742.3401.

EXAMPLE 8

2-{[2-({[N-({4-[3-((2R)-2-amino-4-phenylbutanoylaminooxy)propyl]phenyl}methyl)carbamoyl]methyl}{2-[bis(carboxymethyl)amino]ethyl}amino)ethyl](carboxymethyl)amino}acetic acid, trifluoroacetic acid salt

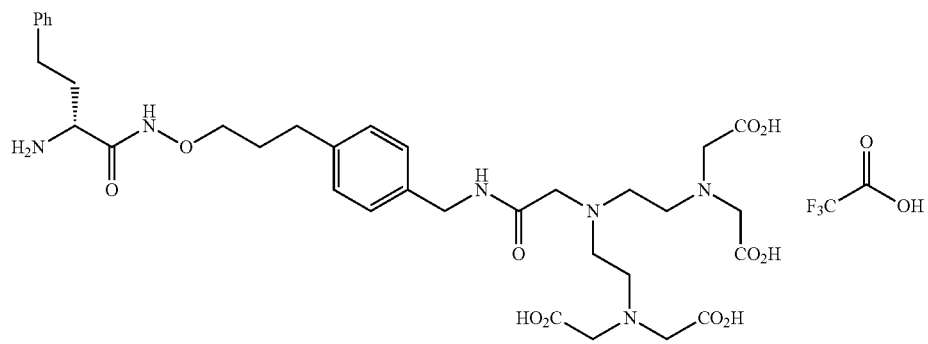 [SMILES: N[C@H](CCc1ccccc1)C(=O)NOCCCc1ccc(CNC(=O)CN(CCN(CC(=O)O)CC(=O)O)CCN(CC(=O)O)CC(=O)O)cc1 ; O=C(O)C(F)(F)F]

part A—Preparation of (2R)-N-{3-[4-(aminomethyl)phenyl]propoxy}-2-[(tert-butoxy)carbonylamino]-4-phenylbutanamide, trifluoroacetic acid salt

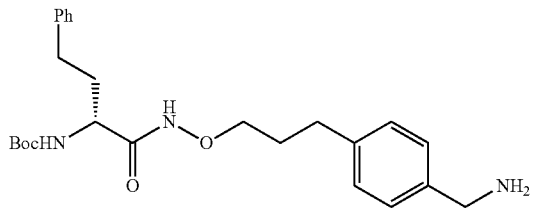

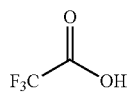

A solution of Boc-DHfe-OH (0.101 g, 0.360 mmol) in CH$_2$Cl$_2$ (3.00 mL) was successively treated with HOBt (55.1 mg, 0.360 mmol), i-Pr$_2$NEt (125 µL, 0.720 mmol) and HBTU (0.137 g, 0.360 mmol) at 22° C. After 0.25 h, the solution was treated with the product of Part 7C (90.2 mg, 0.300 mmol) in one portion. The resulting solution was stirred 1 h then all volatiles removed in vacuo. The crude hydroxamate ester was redissolved in 2:1 MeCN/H$_2$O (3.00 mL) and successively treated with 17.1 mg TPPTS (30.0 µmol; 10 mol %), Et$_2$NH (78 µL, 0.75 mmol) and 3.4 mg Pd(OAc)$_2$ (15 µmol; 5 mol %) at 22° C. Complete deprotection was observed within 1 h. The resulting yellow solution was diluted with H$_2$O containing 0.1% TFA (5.00 mL) then filtered through a 0.45 µm Acrodisk and directly purified by HPLC on a Phenomenex Luna C18 column (21.2×250 mm) using a 1%/min gradient from 30-70% MeCN containing 0.1% TFA and 10% H$_2$O at 20 mL/min. The main product peak eluting at 25 min was collected and lyophilized to a white powder (48.2 mg, 86.8 µmol; 28.9%). $^1$H NMR (DMSO-d$_6$, 600 MHz): δ 11.11 (1H, brs), 8.12 (3H, brs), 7.34 (2H, AB, J$_{AB}$=8.1 Hz), 7.28-7.25 (4H, m), 7.18-7.16 (3H, m), 7.06 (1H, brd, J=7.8 Hz), 4.00-3.96 (2H, m), 3.77-3.70 (3H, m), 2.67 (2H, t, J=7.6 Hz), 2.62-2.57 (1H, m), 2.52-2.47 (1H, m), 1.83-1.78 (4H, m), 1.38 (9H, s). $^{13}$C NMR (DMSO-d$_6$, 75 MHz): δ 168.8, 155.3, 142.1, 141.2, 131.4, 128.8, 128.6, 128.3, 125.8, 76.1, 74.2, 51.9, 42.0, 33.5, 31.5, 31.0, 29.4, 28.1. HRMS calcd for C$_{25}$H$_{35}$N$_3$O$_4$ (M+H): 442.2700. Found: 442.2698.

part B—Preparation of 2-{[2-({[N-({4-[3-((2R)-2-amino-4-phenylbutanoylaminooxy)-propyl]phenyl}methyl)carbamoyl]methyl}{2-[bis(carboxymethyl)amino]ethyl}amino)-ethyl](carboxymethyl)amino}acetic acid, trifluoroacetic acid salt

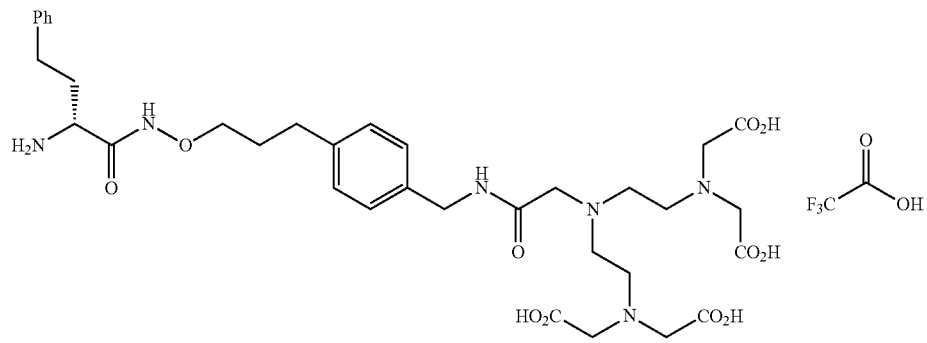 [SMILES: N[C@H](CCc1ccccc1)C(=O)NOCCCc1ccc(CNC(=O)CN(CCN(CC(=O)O)CC(=O)O)CCN(CC(=O)O)CC(=O)O)cc1 ; O=C(O)C(F)(F)F]

A solution of 2-{bis[2-(bis{[(tert-butyl)oxycarbonyl]methyl}amino)ethyl]amino}acetic acid (18.5 mg, 30.0 µmol), HOBt (4.6 mg, 30.0 µmol) and the product of Part 8A (13.9 mg, 25.0 µmol) in dry DMF (1.00 mL) was successively treated with i-Pr$_2$NEt (10 µL, 6 µmol) and HBTU (11.4 mg, 30.0 mol) at 22° C. The resulting solution was stirred 0.25 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (25.0 µmol theoretical) was dissolved in dioxane (0.500 mL) then successively treated with H$_2$O (3 µL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed in vacuo and the white solid residue redissolved in H$_2$O containing 0.1% TFA (8.00 mL) then directly purified by HPLC on a Phenomenex Luna C18 column (21.2×250 mm) using a 1%/min gradient from 10-50% MeCN containing 0.1% TFA and 10% H$_2$O at 20 mL/min. The main product peak eluting at 21 min was collected and lyophilized to a white powder (10.5 mg, 9.92 µmol; 39.7%). $^1$H NMR (DMSO-d$_6$, 600 MHz): δ 11.74 (1H, brs), 8.89 (1H, brt, J=5.8 Hz), 8.35 (3H, brs), 7.30 (2H, dd, J=7.6, 7.3 Hz), 7.22-7.16 (8H, m), 4.30 (2H, brd, J=5.5 Hz), 4.22 (2H, s), 3.83 (2H, dd, J=6.4, 6.1 Hz), 3.67 (1H, brs), 3.49 (8H, s), 3.37 (4H, brt, J=5.5 Hz), 3.04 (4H, brt, J=5.7 Hz), 2.66 (2H, dd, J=7.9, 7.6 Hz), 2.58 (2H, dd, J=8.4, 8.2 Hz), 2.01-1.92 (2H, m), 1.87-1.82 (2H, m). $^{13}$C NMR (DMSO-d$_6$, 151 MHz): δ 172.7, 165.1, 164.6, 157.9 (q, J=31.7 Hz), 140.3, 140.2, 135.8, 128.5, 128.3, 128.0, 127.4, 126.2, 117.0 (q, J=299 Hz), 74.8, 54.3, 53.9, 52.2, 50.3, 48.6, 42.1, 32.8, 30.9, 30.4, 29.4. HRMS calcd for C$_{34}$H$_{48}$N$_6$O$_{11}$ (M+H): 717.3454. Found: 717.3446.

EXAMPLE 9

2-({2-[({N-[6-((2R)-2-amino-4-phenylbutanoylaminooxy)hexyl]carbamoyl}methyl){2-[bis(carboxymethyl)amino]ethyl}amino]ethyl}(carboxymethyl)amino)acetic acid, trifluoroacetic acid salt

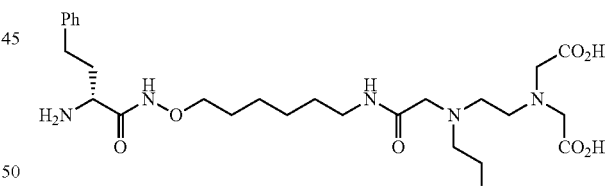

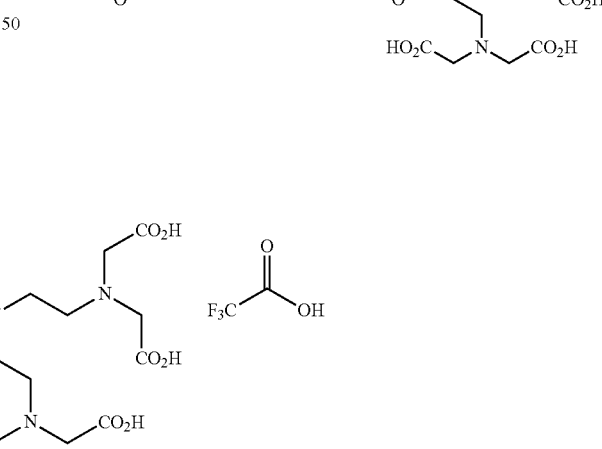

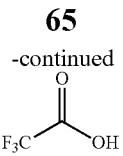

part A—Preparation of (2R)-N-(6-aminohexyloxy)-2-[(tert-butoxy)carbonylamino]-4-phenylbutanamide, trifluoroacetic acid salt

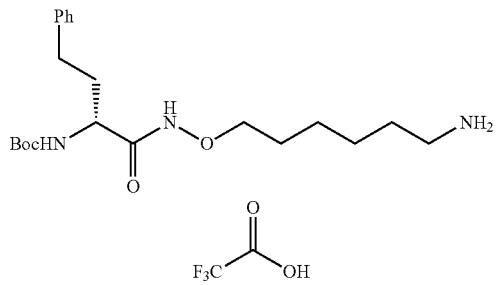

A solution of Boc-DHfe-OH (0.101 g, 0.360 mmol) in CH$_2$Cl$_2$ (3.00 mL) was successively treated with HOBt (55.1 mg, 0.360 mmol), i-Pr$_2$NEt (125 μL, 0.720 mmol) and HBTU (0.137 g, 0.360 mmol) at 22° C. After 0.25 h, the solution was treated with the product of Part 4C (75.8 mg, 0.300 mmol) in one portion. The resulting solution was stirred 1 h then all volatiles removed in vacuo. The crude hydroxamate ester was redissolved in 2:1 MeCN/H$_2$O (3.00 mL) and successively treated with 17.1 mg TPPTS (30.0 mmol; 10 mol %), Et$_2$NH (78 μL, 0.75 mmol) and 3.4 mg Pd(OAc)$_2$ (15 mmol; 5 mol %) at 22° C. Complete deprotection was observed within 1 h. The resulting yellow solution was diluted with H$_2$O containing 0.1% TFA (5.00 mL) then filtered through a 0.45 μm Acrodisk and directly purified by HPLC on a Phenomenex Luna C18 column (21.2×250 mm) using a 1%/min gradient from 10-50% MeCN containing 0.1% TFA and 10% H$_2$O at 20 mL/min. The main product peak eluting at 32 min was collected and lyophilized to a white powder (37.8 mg, 74.5 mmol; 24.8%). A small amount of TPPTS can be detected in the $^1$H NMR spectrum. $^1$H NMR (DMSO-d$_6$, 600 MHz): δ 11.07 (1H, brs), 7.77 (3H, brs), 7.26 (2H, dd, J=7.6, 7.6 Hz), 7.18-7.15 (3H, m), 7.04 (1H, brd, J=7.6 Hz), 3.77-3.70 (3H, m), 2.78-2.73 (2H, m), 2.62-2.57 (1H, m), 2.52-2.47 (1H, m), 1.82-1.75 (2H, m), 1.54-1.49 (4H, m), 1.38 (9H, s), 1.38-1.27 (4H, m). $^{13}$C NMR (DMSO-d$_6$, 151 MHz): δ 168.7, 158.2 (q, J=32.0 Hz), 155.2, 141.23, 128.3, 128.2, 125.8, 116.9 (q, J=293 Hz), 78.0, 74.8, 51.9, 38.7, 33.6, 31.5, 28.1, 27.2, 26.8, 25.5, 24.8. HRMS calcd for C$_{21}$H$_{35}$N$_3$O$_4$ (M+H): 394.2700. Found: 394.2698.

part B—Preparation of 2-({2-[({N-[6-((2R)-2-amino-4-phenylbutanoylaminooxy)hexyl]-carbamoyl}methyl) {2-[bis(carboxymethyl)amino]ethyl}amino]ethyl}(carboxymethyl)-amino)acetic acid, trifluoroacetic acid salt

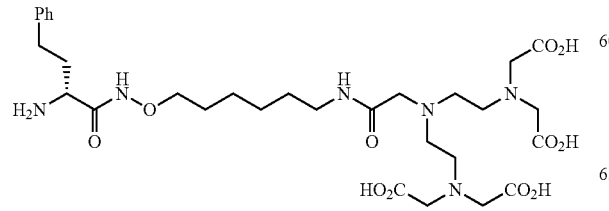

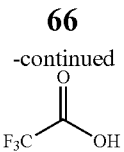

A solution of 2-{bis[2-(bis{[(tert-butyl)oxycarbonyl]methyl}amino)ethyl]amino}acetic acid (18.5 mg, 30.0 μmol), HOBt (4.6 mg, 30.0 μmol) and the product of Part 9A (12.7 mg, 25.0 μmol) in dry DMF (1.00 mL) was successively treated with i-Pr$_2$NEt (10 μL, 6 μmol) and HBTU (11.4 mg, 30.0 mol) at 22° C. The resulting solution was stirred 0.25 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (25.0 μmol theoretical) was dissolved in dioxane (0.500 mL) then successively treated with H$_2$O (3 μL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed in vacuo and the white solid residue redissolved in H$_2$O containing 0.1% TFA (8.00 mL) then directly purified by HPLC on a Phenomenex Luna C18 column (21.2×250 mm) using a 1%/min gradient from 0-40% MeCN containing 0.1% TFA and 10% H$_2$O at 20 mL/min. The main product peak eluting at 27 min was collected and lyophilized to a white powder (10.4 mg, 10.3 μmol; 41.2%). $^1$H NMR (DMSO-d$_6$, 600 MHz): δ 11.64 (1H, brs), 8.41 (1H, brt, J=5.3 Hz), 8.31 (2H, brs), 7.30 (2H, dd, J=7.6, 7.5 Hz), 7.21 (1H, dd, J=7.4, 7.4 Hz), 7.18 (2H, d, J=7.2 Hz), 4.13 (2H, brs), 3.84-3.76 (2H, m), 3.64 (1H, brs), 3.49 (8H, s), 3.34 (4H, brt, J=4.9 Hz), 3.10 (2H, td, J=6.8, 6.0 Hz), 3.03 (4H, brt, J=5.7 Hz), 2.58 (2H, dd, J=8.4, 8.0 Hz), 2.01-1.93 (2H, m), 1.59-1.54 (2H, m), 1.45-1.40 (2H, m), 1.38-1.25 (4H, m). $^{13}$C NMR (DMSO-d$_6$, 151 MHz): δ 172.7, 165.0, 164.3, 157.7 (q, J=31.4 Hz), 140.1, 128.5, 128.0, 126.2, 117.0 (q, J=300 Hz), 75.4, 54.3, 53.9, 52.1, 50.2, 48.6, 38.7, 32.8, 30.3, 28.7, 27.4, 26.1, 24.9. HRMS calcd for C$_{30}$H$_{48}$N$_6$O$_{11}$ (M+H): 669.3454. Found: 669.3446.

EXAMPLE 10

2-[(2-{[(N-{[4-((2R)-2-amino-4-methylpentanoylaminooxy)phenyl]methyl}carbamoyl)methyl]{2-[bis(carboxymethyl)amino]ethyl}amino}ethyl)(carboxymethyl)amino]acetic acid, trifluoroacetic acid salt

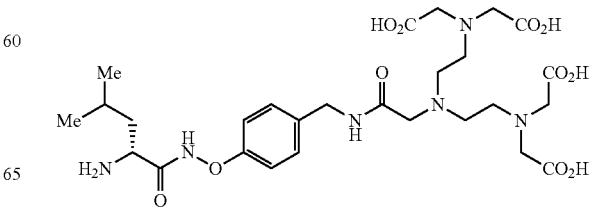

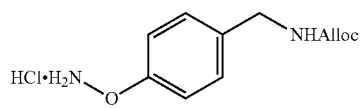

part A—Preparation of N-{[4-(aminooxy)phenyl]methyl}prop-2-enyloxycarboxamide, hydrochloric acid salt

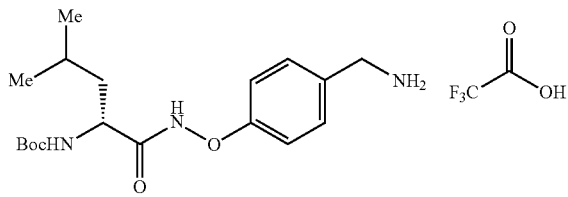 [SMILES: CC(C)C[C@@H](NC(=O)OC(C)(C)C)C(=O)NOc1ccc(CN)cc1 ; O=C(O)C(F)(F)F]

A solution of N-[(4-hydroxyphenyl)methyl]prop-2-enyloxycarboxamide (2.07 g, 10.0 mmol; Imamura, H.; Ohtake, N.; Shimizu, A.; Jona, H.; Sato, H.; Nagano, R.; Ushijima, R.; Yamada, K.; Hashizume, T.; Morishima, H. *Bioorg. Med. Chem. Lett.* 2000, 10(2), 109-113.) in dry MeOH (20.1 mL) was cooled to 0° C. and treated with KOt-Bu (1.12 g, 10.0 mmol) in one portion. The resulting pale pink solution was stirred 0.25 h, then warmed to 22° C., maintained 0.25 h and concentrated in vacuo. The solids were redissolved in DMF (13.0 mL), cooled to 0° C. then treated with freshly prepared amino 2,4,6-trimethylbenzenesulfonate (10.0 mmol; 6.00 mL of a 1.67 M solution in DMF; (a) Carpino, L. A. *J. Am. Chem. Soc.* 1960, 82, 3133. (b) Krause, J. G. *Synthesis* 1972, 3, 140. (c) Suits, J. Z.; Applequist, D. E.; Swart, D. J. *J. Org. Chem.* 1983, 48, 5120.) dropwise over 5 min; additional DMF (2×0.50 mL) was used to quantitate the transfer. After 0.5 h, the resulting solution was diluted with $H_2O$ (100 mL) with transfer to a separatory funnel, then washed with $Et_2O$ (5×50 mL). The combined $Et_2O$ washes were dried over $MgSO_4$, filtered then treated with HCl (4.00 mmol; 1.00 mL of a 4 M solution in dioxane) at 22° C. The resulting plate-like crystals were collected on a scintered glass funnel of fine porosity, washed with $Et_2O$ and pentane (5×20 mL each) then dried to constant weight on the funnel (0.597 g, 2.31 mmol; 23.1%). $^1$H NMR (DMSO-$d_6$, 300 MHz): δ 7.74 (1H, brt, J=6.0 Hz), 7.25 (2H, AA'BB', $J_{AB}$=8.8 Hz, $J_{AA'}$=2.5 Hz), 7.14 (2H, AA'BB', $J_{AB}$=8.8 Hz, $J_{BB'}$=2.5 Hz), 5.90 (1H, ddt, J=17.2, 10.5, 5.4 Hz), 5.26 (1H, dq, J=17.3, 1.5 Hz), 5.16 (1H, dq, J=10.4, 1.4 Hz), 4.47 (2H, dt, J=5.3, 1.5 Hz), 4.13 (2H, brd, J=6.1 Hz). $^{13}$C NMR (DMSO-$d_6$, 151 MHz): δ 156.1, 156.0, 135.3, 133.7, 128.2, 116.9, 114.3, 64.3, 43.1. HRMS calcd for $C_{11}H_{14}N_2O_3$ (M+H): 223.1077. Found: 223.1079.

part B—Preparation of (2R)-N-[4-(aminomethyl)phenoxy]-2-[(tert-butoxy)carbonylamino]-4-methyl-pentanamide, trifluoroacetic acid salt

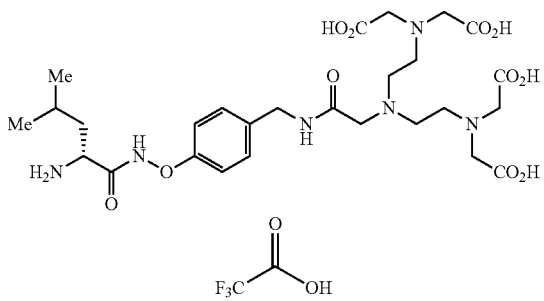

A solution of Boc-DLeu-OH (0.139 g, 0.600 mmol) and HOBt (91.9 mg, 0.600 mmol) in DMF (5.00 mL) was successively treated with i-$Pr_2$NEt (209 μL, 1.20 mmol) and HBTU (0.228 g, 0.600 mmol) at 22° C. After 10 min, the solution was treated with the product of Part 10A (0.129 g, 0.500 mmol) in one portion. The resulting solution was stirred 17 h then treated with additional HBTU (56.9 mg, 0.150 mmol) to complete conversion. After 1 h, the solution was partitioned between EtOAc and 0.1 M citric acid (30 mL each) then transferred to a separatory funnel. The layers separated and the aqueous solution washed with EtOAc (2×30 mL). The combined EtOAc layers were successively washed with 0.1 M citric acid and saturated aqueous solutions of $NaHCO_3$ and NaCl (3×30 mL each) then dried over $MgSO_4$, filtered and concentrated in vacuo to a colorless oil which was used without further purification in the subsequent deprotection step.

The crude hydroxamate ester (0.500 mmol theoretical) was dissolved in 2:1 MeCN/$H_2O$ (5.00 mL) and successively treated with 28.4 mg TPPTS (50.0 mmol; 10 mol %), $Et_2$NH (129 μL, 1.25 mmol) and 5.6 mg Pd(OAc)$_2$ (25.0 mmol; 5 mol %) at 22° C. Complete deprotection was observed within 0.5 h. The resulting amber solution was diluted with $H_2O$ containing 0.1% TFA (3.00 mL) then filtered through a 0.45 μm Acrodisk and directly purified by HPLC on a Phenomenex Luna C18 column (21.2×250 mm) using a 1%/min gradient from 10-40% MeCN containing 0.1% TFA and 10% $H_2O$ at 20 mL/min. The main product peak eluting at 23 min was collected and lyophilized to a white powder (71.3 mg, 0.153 mmol; 30.6%). $^1$H NMR (DMSO-$d_6$, 300 MHz): δ 12.11 (1H, brs), 8.10 (3H, brs), 7.36 (2H, AB, $J_{AB}$=8.5 Hz), 7.17 (1H, brd, J=7.8 Hz), 7.05 (2H, AB, $J_{AB}$=8.6 Hz), 4.00-3.90 (3H, m), 1.66-1.36 (3H, m), 1.41 (9H, s), 0.90 (3H, d, J=6.4 Hz), 0.86 (3H, d, J=6.5 Hz). $^{13}$C NMR (DMSO-$d_6$, 75 MHz): δ 169.8, 159.6, 155.5, 130.2, 127.6, 112.8, 78.2, 50.7, 41.7, 28.1, 24.2, 22.6, 21.7. HRMS calcd for $C_{18}H_{29}N_3O_4$ (M+H—$NH_3$): 335.1965. Found: 335.1969.

part C—Preparation of 2-[(2-{[(N-{[4-((2R)-2-amino-4-methylpentanoylaminooxy)-phenyl]methyl}carbamoyl)methyl]{2-[bis(carboxymethyl)amino]ethyl}amino}-ethyl)(carboxymethyl)amino]acetic acid, trifluoroacetic acid salt A solution of 2-{bis[2-(bis{[(tert-butyl)oxycarbonyl]methyl}amino)ethyl]amino}acetic acid (67.9 mg, 0.110 mmol), HOBt (16.8 mg, 0.110 mmol) and the product of Part 10B (46.5 mg, 0.100 mmol) in dry DMF (2.00 mL) was successively treated with i-$Pr_2$NEt (38 μL, 0.22 mmol) and HBTU (41.7 mg, 0.110 mmol) at 22° C. The resulting solution was stirred 0.5 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (0.110 mmol theoretical) was dissolved in dioxane (1.00 mL) then successively treated with H$_2$O (10 μL) and HCl (4.00 mmol; 1.00 mL of a 4 M solution in dioxane) at 22° C. The resulting pale yellow solution was stirred 15 h, during which time a heavy white precipitate formed. Upon complete deprotection, the volatiles were removed in vacuo and the white solid residue redissolved in H$_2$O containing 0.1% TFA (6.00 mL) then directly purified by HPLC on a Phenomenex Luna C18 column (21.2×250 mm) using a 1%/min gradient from 0-22% MeCN containing 0.1% TFA and 10% H$_2$O at 20 mL/min. The main product peak eluting at 18 min was collected and lyophilized to a white powder (30.8 mg, 31.8 μmol; 31.8%). $^1$H NMR (DMSO-d$_6$, 600 MHz): δ 12.70 (1H, brs), 8.90 (1H, brs), 8.41 (3H, brs), 7.26 (2H, AB, J$_{AB}$=8.4 Hz), 7.03 (2H, AB, J$_{AB}$=8.1 Hz), 4.30 (2H, brd, J=5.2 Hz), 4.20 (2H, s), 3.81 (1H, brs), 3.50 (8H, s), 3.36 (4H, brt, J=5.4 Hz), 3.04 (4H, brt, J=5.8 Hz), 1.64 (3H, brs), 0.95 (3H, brd, J=5.5 Hz), 0.92 (3H, brd, J=5.5 Hz). $^{13}$C NMR (DMSO-d$_6$, 151 MHz): δ 172.7, 166.4, 164.7, 158.2, 158.0 (q, J=30.7 Hz), 132.8, 128.7, 117.1 (q, J=300 Hz), 113.0, 54.3, 53.9, 52.2, 49.0, 48.7, 41.7, 40.0, 23.8, 22.2, 22.0. HRMS calcd for C$_{27}$H$_{42}$N$_6$O$_{11}$ (M+H): 627.2986. Found: 627.2989.

EXAMPLE 11

2-[(2-{[(N-{[4-((2R)-2-amino-4-phenylbutanoylaminooxy)phenyl]methyl}carbamoyl)methyl]{2-[bis(carboxymethyl)amino]ethyl}amino}ethyl)(carboxymethyl)amino]acetic acid, trifluoroacetic acid salt

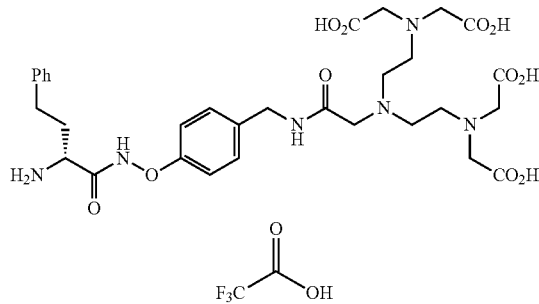

part A—Preparation of (2R)-N-[4-(aminomethyl)phenoxy]-2-[(tert-butoxy)carbonylamino]-4-phenylbutanamide, trifluoroacetic acid salt

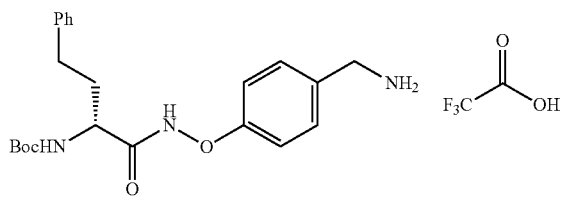 [SMILES: CC(C)(C)OC(=O)N[C@H](CCc1ccccc1)C(=O)NOc1ccc(CN)cc1 ; O=C(O)C(F)(F)F]

A solution of Boc-D-Hfe-OH (0.168 g, 0.600 mmol) and HOBt (91.9 mg, 0.600 mmol) in DMF (5.00 mL) was successively treated with i-Pr$_2$NEt (209 μL, 1.20 mmol) and HBTU (0.228 g, 0.600 mmol) at 22° C. After 10 min, the solution was treated with the product of Part 10A (0.129 g, 0.500 mmol) in one portion. The resulting solution was stirred 17 h then partitioned between EtOAc and 0.1 M citric acid (30 mL each) with transfer to a separatory funnel. The layers separated and the aqueous solution washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step. The crude hydroxamate ester (0.500 mmol theoretical) was dissolved in 2:1 MeCN/H$_2$O (5.00 mL) and successively treated with 28.4 mg TPPTS (50.0 μmol; 10 mol %), Et$_2$NH (129 μL, 1.25 mmol) and 5.6 mg Pd(OAc)$_2$ (25.0 μmol; 5 mol %) at 22° C. Complete deprotection was observed within 0.5 h. The resulting amber solution was diluted with H$_2$O containing 0.1% TFA (3.00 mL) then lyophilized. The solid was redissolved in 10:1 H$_2$O/MeCN (8.00 ml), filtered through a 0.45 μm Acrodisk and directly purified by HPLC on a Phenomenex Luna C18 column (21.2×250 mm) using a 1%/min gradient from 20-50% MeCN containing 0.1% TFA and 10% H$_2$O at 20 mL/min. The main product peak eluting at 17 min was collected and lyophilized to a white powder (0.157 g, 0.305 mmol; 61.0%). $^1$H NMR (DMSO-d$_6$, 600 MHz): δ 12.11 (1H, brs), 8.10 (3H, brs), 7.36 (2H, AB, J$_{AB}$=8.5 Hz), 7.34 (1H, brd, J=7.5 Hz), 7.28 (2H, dd, J=7.7, 7.5 Hz), 7.20 (2H, AB, J$_{AB}$=7.5 Hz), 7.18 (1H, t, J=7.2 Hz), 7.06 (2H, AB, J$_{AB}$=8.5 Hz), 3.96 (2H, brd, J=5.1 Hz), 3.90-3.87 (1H, m), 2.70-2.65 (1H, m), 2.59-2.54 (1H, m), 1.93-1.87 (2H, m), 1.43 (9H, s). $^{13}$C NMR (DMSO-d$_6$, 151 MHz): δ 169.6, 159.6, 155.5, 141.0, 130.2, 128.3, 127.7, 125.9, 112.8, 78.3, 52.2, 41.6, 32.8, 31.5, 28.2. HRMS calcd for C$_{22}$H$_{29}$N$_3$O$_4$(M+H): 400.2231. Found: 400.2241.

part B—Preparation of 2-[(2-{[(N-{[4-((2R)-2-amino-4-phenylbutanoylaminooxy)-phenyl]methyl}carbamoyl)methyl]{2-[bis(carboxymethyl)amino]ethyl}amino}-ethyl)(carboxymethyl)amino]acetic acid, trifluoroacetic acid salt

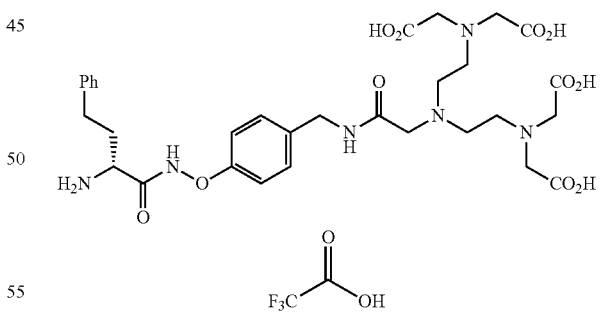

A solution of 2-{bis[2-(bis{[(tert-butyl)oxycarbonyl]methyl}amino)ethyl]amino}acetic acid (47.9 mg, 77.6 μmol), HOBt (10.9 mg, 71.1 μmol) and the product of Part 11A (33.2 mg, 64.7 μmol) in dry DMF (1.29 mL) was successively treated with i-Pr$_2$NEt (25 μL, 0.14 mmol) and EDC (13.6 mg, 71.1 μmol) at 22° C. The resulting solution was stirred 20 h then partitioned between EtOAc and 0.1 M citric acid (30 mL each) with transfer to a separatory funnel. The layers separated and the aqueous layer washed with EtOAc (2×30 mL). The combined EtOAc layers were successively washed with 0.1 M citric acid, 0.1 M NaOH and saturated aqueous NaCl (3×30 mL each) then dried over MgSO$_4$, filtered and concentrated in vacuo to a colorless oil which was used without further purification in the subsequent deprotection step.

The protected conjugate (64.7 µmol theoretical) was dissolved in dioxane (0.650 mL) then successively treated with H$_2$O (6 µL) and HCl (2.60 mmol; 0.650 mL of a 4 M solution in dioxane) at 22° C. The resulting pale yellow solution was stirred 18.5 h, during which time a heavy white precipitate formed. Upon complete deprotection, the volatiles were removed under a stream of N$_2$ and the white solid residue redissolved in H$_2$O containing 0.1% TFA (8.00 mL) then directly purified by HPLC on a Phenomenex Luna C18 column (21.2×250 mm) using a 1%/min gradient from 0-30% MeCN containing 0.1% TFA and 10% H$_2$O at 20 mL/min. The main product peak eluting at 23 min was collected and lyophilized to a white powder (29.4 mg, 28.9 µmol; 44.7%). $^1$H NMR (DMSO-d$_6$, 600 MHz): δ 12.79 (1H, brs), 8.92 (1H, brs), 8.56 (3H, brs), 7.32 (2H, dd, J=7.8, 7.1 Hz), 8.27 (2H, AB, J$_{AB}$=8.4 Hz), 7.23-7.21 (3H, m), 7.06 (2H, d, J=7.6 Hz), 4.31 (2H, brd, J=5.0 Hz), 4.23 (2H, s), 3.50 (8H, s), 3.38 (4H, brs), 3.05 (4H, brt, J=5.4 Hz), 2.67 (2H, brs), 2.09 (2H, brs). $^{13}$C NMR (DMSO-d$_6$, 151 MHz): δ 172.7, 166.1, 164.6, 158.3, 158.2 (q, J=32.9 Hz), 140.2, 132.8, 128.7, 128.6, 128.1, 126.3, 116.9 (q, J=299 Hz), 113.0, 54.3, 53.9, 52.2, 50.4, 48.7, 41.8, 32.9, 30.5. HRMS calcd for C$_{31}$H$_{42}$N$_6$O$_{11}$ (M+H): 675.2984. Found: 675.2997.

EXAMPLE 12

2-[(2-{[(N-{[4-((2R)-2-amino-3-(2-naphthyl)propanoylaminooxy)phenyl]methyl}carbamoyl)methyl]{2-[bis(carboxymethyl)amino]ethyl}amino}ethyl)(carboxymethyl)amino]acetic acid, trifluoroacetic acid salt

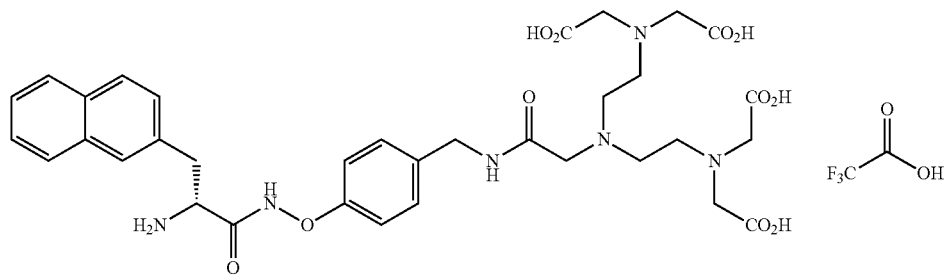 [SMILES: N[C@H](Cc1ccc2ccccc2c1)C(=O)NOc1ccc(CNC(=O)CN(CCN(CC(=O)O)CC(=O)O)CCN(CC(=O)O)CC(=O)O)cc1 ; O=C(O)C(F)(F)F]

part A—Preparation of (2R)-N-[4-(aminomethyl)phenoxy]-2-[(tert-butoxy)carbonylamino]-3-(2-naphthyl)propanamide, trifluoroacetic acid salt

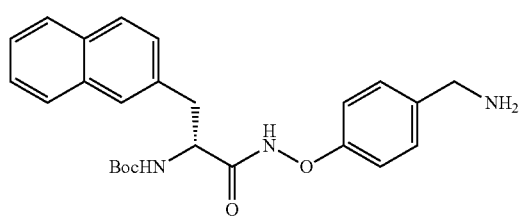

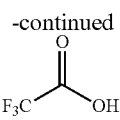

A solution of Boc-DNal-OH (0.189 g, 0.600 mmol) and HOBt (91.9 mg, 0.600 mmol) in DMF (5.00 mL) was successively treated with i-Pr$_2$NEt (209 µL, 1.20 mmol) and HBTU (0.228 g, 0.600 mmol) at 22° C. After 10 min, the solution was treated with the product of Part 10A (0.129 g, 0.500 mmol) in one portion. The resulting solution was stirred 17 h then treated with additional HBTU (56.9 mg, 0.150 mmol) to complete conversion. After 1 h, the solution was partitioned between EtOAc and 0.1 M citric acid (30 mL each) then transferred to a separatory funnel. The layers separated and the aqueous solution washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The crude hydroxamate ester (0.500 mmol theoretical) was dissolved in 2:1 MeCN/H$_2$O (5.00 mL) and successively treated with 28.4 mg TPPTS (50.0 µmol; 10 mol %), Et$_2$NH (129 µL, 1.25 mmol) and 5.6 mg Pd(OAc)$_2$ (25.0 mmol; 5 mol %) at 22° C. Complete deprotection was observed within 0.5 h. The resulting amber solution was diluted with H$_2$O containing 0.1% TFA (3.00 mL) then lyophilized. The solid was redissolved in 1:1 H$_2$O/MeCN (8.00 ml), filtered through a 0.45 µm Acrodisk and directly purified by HPLC on a Phenomenex Luna C18 column (21.2×250 mm) using a 1%/min gradient from 30-60% MeCN containing 0.1% TFA and 10% H$_2$O at 20 mL/min. The main product peak eluting at 12 min was collected and lyophilized to a white powder (0.115 g, 0.209 mmol; 41.9%). $^1$H NMR (DMSO-d$_6$, 600 MHz): δ 12.08 (1H, s), 8.10 (3H, brs), 7.89 (1H, d, J=7.5 Hz), 7.86 (1H, d, J=8.5 Hz), 7.83 (1H, d, J=7.5 Hz), 7.76 (1H, s), 7.51-7.47 (2H, m), 7.45 (1H, d, J=8.0 Hz), 7.40 (1H, brd, J=7.7 Hz), 7.21 (2H, AB, J$_{AB}$=8.3 Hz), 6.86 (2H, AB, J$_{AB}$=8.5 Hz), 4.28-4.24 (1H, m), 3.92 (2H, brs), 3.14 (1H, ABX, J$_{AB}$=13.6 Hz, J$_{AX}$=6.7 Hz), 3.06 (1H, ABX, J$_{AB}$=13.3 Hz, J$_{BX}$=8.8 Hz), 1.35 (9H, s). $^{13}$C NMR (DMSO-d$_6$, 151 MHz): δ 168.8, 159.4, 155.3, 135.1, 132.9, 131.9, 130.1, 127.6, 127.6, 127.6, 127.5, 127.4, 126.0, 125.5, 112.7, 78.3, 53.8, 41.6, 36.9, 28.1. HRMS calcd for C$_{25}$H$_{29}$N$_3$O$_4$ (M+H—NH$_3$): 419.1965. Found: 419.1967.

part B—Preparation of 2-[(2-{[(N-{[4-((2R)-2-amino-3-(2-naphthyl)propanoylaminooxy)-phenyl]methyl}carbamoyl)methyl]{2-[bis(carboxymethyl)amino]ethyl}amino}-ethyl)(carboxymethyl)amino]acetic acid, trifluoroacetic acid salt

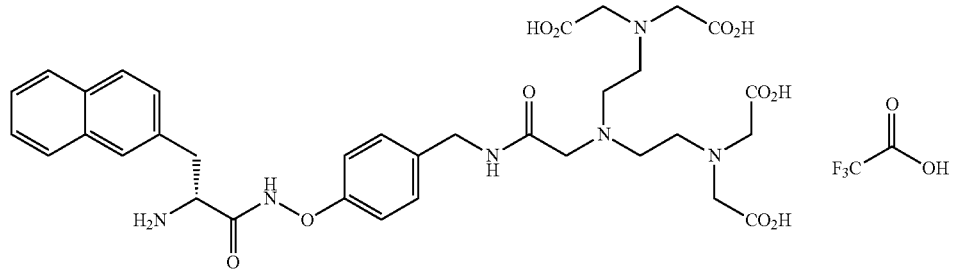 [SMILES: N[C@H](Cc1ccc2ccccc2c1)C(=O)NOc1ccc(CNC(=O)CN(CCN(CC(=O)O)CC(=O)O)CCN(CC(=O)O)CC(=O)O)cc1 ; O=C(O)C(F)(F)F]

A solution of 2-{bis[2-(bis{[(tert-butyl)oxycarbonyl]methyl}amino)ethyl]amino}acetic acid (67.9 mg, 0.110 mmol), HOBt (16.8 mg, 0.110 mmol) and the product of Part 12A (54.9 mg, 0.100 mmol) in dry DMF (2.00 mL) was successively treated with i-Pr$_2$NEt (38 µL, 0.22 mmol) and HBTU (41.7 mg, 0.110 mmol) at 22° C. The resulting solution was stirred 0.5 h then partitioned between EtOAc and 0.1 M citric acid (30 mL each) with transfer to a separatory funnel.

The layers separated and the aqueous layer washed with EtOAc (2×30 mL). The combined EtOAc layers were successively washed with 0.1 M citric acid and saturated aqueous solutions of NaHCO$_3$ and NaCl (3×30 mL each) then dried over MgSO$_4$, filtered and concentrated in vacuo to a colorless oil which was used without further purification in the subsequent deprotection step.

The protected conjugate (0.100 mmol theoretical) was dissolved in dioxane (1.00 mL) then successively treated with H$_2$O (10 µL) and HCl (4.00 mmol; 1.00 mL of a 4 M solution in dioxane) at 22° C. The resulting pale yellow solution was stirred 15 h, during which time a heavy white precipitate formed. Upon complete deprotection, the volatiles were removed under a stream of N$_2$ and the white solid residue redissolved in H$_2$O containing 0.1% TFA (8.00 mL) then directly purified by HPLC on a Phenomenex Luna C18 column (21.2×250 mm) using a 1%/min gradient from 5-30% MeCN containing 0.1% TFA and 10% H$_2$O at 20 mL/min. The main product peak eluting at 20 min was collected and lyophilized to a white powder (40.5 mg, 38.5 µmol; 38.5%). $^1$H NMR (DMSO-d$_6$, 600 MHz): δ 12.49 (1H, brs), 8.84 (1H, brt, J=5.1 Hz), 8.63 (2H, brs), 7.98-7.95 (2H, m), 7.89-7.86 (1H, m), 7.77 (1H, brs), 7.57-7.54 (2H, m), 7.45 (1H, brs), 6.85 (2H, AB, J$_{AB}$=8.2 Hz), 6.50 (2H, AB, J$_{AB}$=7.6 Hz), 4.20 (2H, s), 4.21-4.15 (3H, m), 3.51 (8H, s), 3.38 (4H, brt, J=5.5 Hz), 3.35-3.31 (1H, m), 3.26-3.22 (1H, m), 3.05 (4H, brt, J=5.7 Hz). $^{13}$C NMR (DMSO-d$_6$, 151 MHz): δ 172.7, 156.2, 164.6, 158.1 (q, J=31.8 Hz), 157.8, 133.0, 132.4, 132.3, 132.2, 128.4, 128.3, 128.3, 127.6, 127.6, 127.3, 126.3, 126.0, 117.1 (q, J=299 Hz), 112.6, 54.3, 53.8, 52.2, 51.6, 48.7, 41.7, 37.0. HRMS calcd for C$_{34}$H$_{42}$N$_6$O$_{11}$ (M+H): 711.2986. Found: 711.2985.

EXAMPLE 13

2-{[2-({[N-({4-[2-((2R)-2-amino-4-methylpentanoylaminooxy)ethyl]phenyl}methyl)carbamoyl]methyl}{2-[bis(carboxymethyl)amino]ethyl}amino)ethyl](carboxymethyl)amino}acetic acid, trifluoroacetic acid salt

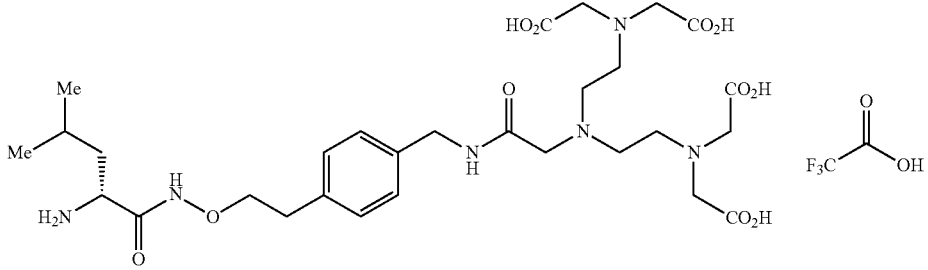 [SMILES: CC(C)C[C@@H](N)C(=O)NOCCc1ccc(CNC(=O)CN(CCN(CC(=O)O)CC(=O)O)CCN(CC(=O)O)CC(=O)O)cc1 ; O=C(O)C(F)(F)F]

part A—Preparation of N-methoxy-N-methyl(4-{[(phenylmethoxy)carbonylamino]-methyl}phenyl)carboxamide

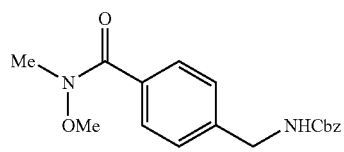 [SMILES: CON(C)C(=O)c1ccc(CNC(=O)OCc2ccccc2)cc1]

A solution of 4-{[(phenylmethoxy)carbonylamino]methyl}benzoic acid (3.99 g, 14.0 mmol; Groves, K.; Wilson, A. J.; Hamilton, A. D. J. Am. Chem. Soc. 2004, 126(40), 12833-12842.) and HOBt (2.57 g, 16.8 mmol) in dry DMF (70.0 mL) was successively treated with i-Pr$_2$NEt (4.87 mL, 28.0 mmol) and EDC (3.22 g, 16.8 mmol) at 22° C. After 0.25 h, the solution was treated with methoxymethylamine hydrochloride (1.64 g, 16.8 mmol) in one portion. The resulting mixture was stirred 1 h then partitioned between EtOAc and 0.1 M citric acid (100 mL each) with transfer to a separatory funnel. The layers separated and the aqueous layer washed with EtOAc (2×50 mL). The combined EtOAc layers were successively washed with 0.1 M citric acid, 0.1 M NaOH and saturated aqueous NaCl (3×50 mL each) then dried over MgSO$_4$, filtered and concentrated in vacuo. Purification by chromatography on silica (40×250 mm) using a gradient elution from 1:1→3:7 pentane/EtOAc (R$_f$=0.3 in 1:1 hexanes/EtOAc) afforded pure material as a colorless oil (3.94 g, 12.0 mmol; 85.9%). $^1$H NMR (CDCl$_3$, 300 MHz): δ 7.63 (2H, AA'BB', J$_{AB}$=8.3 Hz, J$_{AA}$=1.9 Hz), 7.36-7.27 (7H, m), 5.20 (1H, brs), 5.13 (2H, s), 4.40 (2H, brd, J=6.0 Hz), 3.52 (3H, s), 3.33 (3H, s). $^{13}$C NMR (CDCl$_3$, 75 MHz): δ 169.5, 156.4, 141.1, 136.4, 133.2, 128.6, 128.5, 128.1, 128.1, 126.9, 66.9, 61.0, 44.8, 33.7. HRMS calcd for C$_{18}$H$_{20}$N$_2$O$_4$: 329.1496. Found: 329.1497.

part B—Preparation of N-[(4-acetylphenyl)methyl](phenylmethoxy)carboxamide

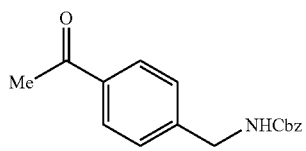 [SMILES: CC(=O)c1ccc(CNC(=O)OCc2ccccc2)cc1]

A solution of the product of Part 13A (3.28 g, 10.0 mmol) in dry THF (100 mL) was cooled to 0° C. and treated with MeLi (30.0 mmol; 10.2 mL of a 2.94 M solution in Et$_2$O) dropwise over 0.25 h; during the addition a heavy white precipitate formed. After 0.5 h, the resulting suspension was treated with a solution of conc. HCl in absolute EtOH (5:95 v/v; 100 mL) then diluted with Et$_2$O and saturated aqueous NaCl (100 mL each) with transfer to a separatory funnel. The layers separated and the aqueous layer washed with Et$_2$O (2×50 mL). The combined Et$_2$O layers were further washed with saturated aqueous NaCl (3×100 mL) then dried over MgSO$_4$, filtered and concentrated in vacuo. The crude material was purified by chromatography on silica (40×300 mm) using 1:1 hexanes/EtOAc. The main product eluted between 300-500 mL, was collected and concentrated to an amorphous white powder that was recrystallized from Et$_2$O/pentane to afford fine colorless needles (1.57 g, 5.54 mmol; 55.6%). Mp 101.0-103.0° C. $^1$H NMR (CDCl$_3$, 300 MHz): δ 7.90 (2H, AB, J$_{AB}$=8.3 Hz), 7.34 (7H, brs), 5.22 (1H, brs), 5.13 (2H, s), 4.40 (2H, brd, J=6.2 Hz), 2.57 (3H, s). $^{13}$C NMR (DMSO-d$_6$, 151 MHz): δ 197.6, 156.4, 143.9, 136.4, 136.3, 128.7, 128.5, 128.2, 128.1, 127.4, 67.0, 44.7, 26.6. HRMS calcd for C$_{17}$H$_{17}$NO$_3$ (M+H): 284.1281. Found: 284.1280.

part C—Preparation of Methyl 2-(4-{[(phenylmethoxy)carbonylamino]methyl}phenyl)acetate

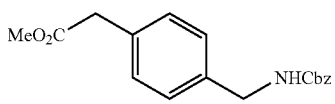 [SMILES: COC(=O)Cc1ccc(CNC(=O)OCc2ccccc2)cc1]

A solution of the product of Part 13B (1.24 g, 4.38 mmol) in 3:1 MeOH/HC(OMe)$_3$ (28.0 mL) was successively treated with AgNO$_3$ (1.56 g, 9.18 mmol) and I$_2$ (1.17 g, 4.61 mmol) at 22° C. The resulting solution was warmed to 68° C. and maintained at reflux for 2 h. After cooling to 22° C., the suspension was filtered through a scintered glass funnel and the filtrate partitioned between Et$_2$O and H$_2$O (50 mL each) with transfer to a separatory funnel. The layers separated and the aqueous layer washed with Et$_2$O (2×50 mL). The combined Et$_2$O layers were dried over MgSO$_4$, filtered and concentrated in vacuo to a white solid that was used without further purification in the subsequent reduction step. $^1$H NMR (CDCl$_3$, 300 MHz): δ 7.87-7.80 (5H, m), 7.23 (4H, s), 5.13 (2H, s), 5.04 (1H, brs), 4.36 (2H, brd, J=5.9 Hz), 3.68 (3H, s), 3.60 (2H, s)

part D—Preparation of N-{[4-(2-hydroxyethyl)phenyl]methyl}(phenylmethoxy)carboxamide

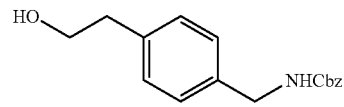 [SMILES: O=C(NCc1ccc(CCO)cc1)OCc1ccccc1]

A solution of the product of Part 13C (1.20 g, 3.83 mmol) in dry THF (38.3 mL) was cooled to 0° C. and treated with LiAlH$_4$ (3.83 mmol; 3.83 mL of a 1 M solution in THF) dropwise over 10 min. The resulting solution was stirred 0.25 h at 0° C. to ensure complete reduction. Excess LiAlH$_4$ was consumed by the careful addition of H$_2$O (145 μL). The resulting white suspension was successively treated with 15% aqueous NaOH (145 μL) and H$_2$O (435 μL) then stirred for 0.25 h to a fine white slurry. The resulting mixture was filtered through a pad of Celite and concentrated in vacuo. The crude oil was purified by chromatography on silica using 1:1 hexanes/EtOAc to afford a white solid (0.670 g, 2.35 mmol; 61.3%). $^1$H NMR (CDCl$_3$, 600 MHz): δ 7.36-7.29 (5H, m), 7.23 (2H, AB, J$_{AB}$=7.3 Hz), 7.19 (2H, AB, J$_{AB}$=7.7 Hz), 5.13 (2H, s), 5.03 (1H, brs), 4.36 (2H, brd, J=5.5 Hz), 3.84 (2H, t, J=6.6 Hz), 2.85 (2H, t, J=6.6 Hz), 1.46 (1H, brs). HRMS calcd for C$_{17}$H$_{19}$NO$_3$ (M+Na): 308.1257. Found: 308.1257.

part E—Preparation of N-({4-[2-(1,3-dioxoisoindolin-2-yloxy)ethyl]phenyl}methyl)-(phenylmethoxy)carboxamide

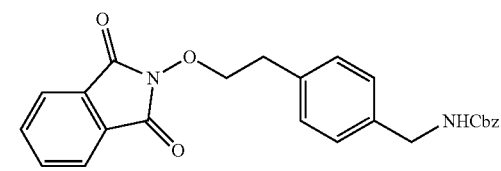 [SMILES: O=C(NCc1ccc(CCON2C(=O)c3ccccc3C2=O)cc1)OCc1ccccc1]

A solution of the product of Part 13D (0.300 g, 1.05 mmol), 2-hydroxyisoindoline-1,3-dione (0.206 g, 1.26 mmol) and PPh$_3$ (0.414 g, 1.58 mmol) in dry THF (10.5 mL) was cooled to 0° C. and treated with DEAD (0.224 mL, 1.42 mmol) dropwise such that the orange color did not persist. The pale yellow solution thus obtained was immediately warmed to 22° C., concentrated in vacuo and directly purified by chromatography on silica using a gradient elution from 2:1→1:1 hexanes/EtOAc (R$_f$=0.5 in 1:1 hexanes/EtOAc). The product containing fractions were combined and concentrated to a white crystalline solid (0.354 g, 0.822 mmol; 78.2%). $^1$H NMR (CDCl$_3$, 600 MHz): δ 7.83-7.80 (2H, m), 7.74-7.72 (2H, m), 7.36-7.29 (5H, m), 7.26 (2H, AB, J$_{AB}$=8.0 Hz), 7.21 (2H, AB, J$_{AB}$=7.5 Hz), 5.13 (2H, s), 4.98 (1H, brs), 4.42 (2H, t, J=7.3 Hz), 4.33 (2H, brd, J=5.5 Hz), 3.12 (2H, t, J=7.3 Hz). HRMS calcd for C$_{25}$H$_{22}$N$_2$O$_5$ (M+Na): 453.1421. Found: 453.1425.

part F—Preparation of N-({4-[2-(aminooxy)ethyl]phenyl}methyl)(phenylmethoxy)carboxamide, hydrochloric acid salt

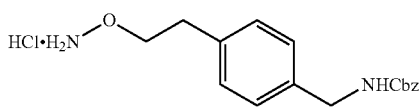

A solution of the product of Part 13E (0.341 g, 0.792 mmol) in 9:1 CHCl$_3$/MeOH (8.00 mL) was treated with hydrazine hydrate (0.190 mL, 3.92 mmol) in one portion at 22° C. Within 5 min a white precipitate formed; after 1 h the reaction was complete. The suspension was filtered through a plug of silica (25 g) then eluted with 9:1 CH$_2$Cl$_2$/MeOH (750 mL) and concentrated in vacuo to a white solid. The solid was triturated with Et$_2$O then removed by filtration through a scintered glass funnel. The filtrate was further treated with HCl (0.8 mmol; 0.2 mL of a 4 M solution in dioxane) and the resulting precipitate collected, washed with Et$_2$O (10×5 mL) and dried to constant weight in vacuo (0.220 g, 0.653; 82.5%). $^1$H NMR (DMSO-d$_6$, 600 MHz): δ 10.94 (2H, brs), 7.78 (1H, brt, J=5.8 Hz), 7.37-7.28 (5H, m), 7.20 (2H, AB, J$_{AB}$=8.4 Hz), 7.18 (2H, AB, J$_{AB}$=8.4 Hz), 5.03 (2H, s), 4.20 (2H, t, J=6.6 Hz), 4.16 (2H, brd, J=6.0 Hz), 2.90 (2H, t, J=6.5 Hz). HRMS calcd for C$_{17}$H$_{20}$N$_2$O$_3$ (M+H): 301.1547. Found: 301.1550.

part G—Preparation of (2R)-N-{2-[4-(aminomethyl)phenyl]ethoxy}-2-[(tert-butoxy)carbonyl-amino]-4-methylpentanamide, trifluoroacetic acid salt

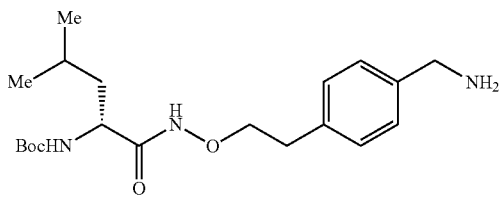

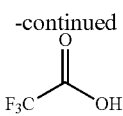

A solution of Boc-DLeu-OH (49.0 mg, 0.197 mmol) in DMF (1.00 mL) was successively treated with HOBt (30.0 mg, 0.196 mmol), i-Pr$_2$NEt (51 μL, 0.293 mmol) and HBTU (75.0 mg, 0.198 mmol) at 22° C. After 0.25 h, the solution was treated with the product of Part 13F (55.0 mg, 0.163 mmol) in one portion. The resulting solution was stirred 0.5 h then diluted with EtOAc (25 mL) and transferred to a separatory funnel. The EtOAc solution was successively washed with 0.1 M citric acid (3×30 mL) and saturated aqueous solutions of NaHCO$_3$ (3×30 mL) and NaCl (30 mL) then dried over MgSO$_4$, filtered and concentrated in vacuo to a colorless oil which was used without further purification in the subsequent deprotection step.

The crude hydroxamate ester (0.163 mmol theoretical) was dissolved in MeOH (1.00 mL) and treated with 10% Pd on carbon (17.4 mg, 16.3 μmol; 10 mol %) in one portion at 22° C. The resulting suspension was sparged with 1 atm H$_2$, and maintained 1 h. After purging the vessel with N$_2$, the suspension was filtered through a 0.45 μm Acrodisk then concentrated in vacuo. The residue was redissolved in 1:1 MeCN/H$_2$O (3.00 mL) then directly purified by HPLC on a Phenomenex Luna C18 column (21.2×250 mm) using a 1%/min gradient from 15-45% MeCN containing 0.1% TFA and 10% H$_2$O at 20 mL/min. The main product peak eluting at 20 min was collected and lyophilized to a white powder (61.2 mg, 0.124 mmol; 75.9%). $^1$H NMR (DMSO-d$_6$, 600 MHz): δ 11.15 (1H, brs), 8.12 (2H, brs), 7.36 (2H, AB, J$_{AB}$=8.1 Hz), 7.33 (2H, AB, J$_{AB}$=8.1 Hz), 6.91 (1H, brd, J=7.6 Hz), 3.99 (2H, brs), 3.98-3.89 (2H, m), 3.82-3.78 (1H, m), 2.87 (2H, brt, J=6.2 Hz), 1.58-1.52 (1H, m), 1.46-1.40 (1H, m), 1.36 (9H, s), 1.36-1.31 (1H, m), 0.87 (3H, d, J=6.5 Hz), 0.84 (3H, d, J=6.5 Hz). HRMS calcd for C$_{20}$H$_{33}$N$_3$O$_4$ (M+H): 380.2544. Found: 380.2548.

part H—Preparation of -{[2-({[N-({4-[2-((2R)-2-amino-4-methylpentanoylaminooxy)ethyl]-phenyl}methyl)carbamoyl]methyl}{2-[bis(carboxymethyl)amino]ethyl}amino)-ethyl](carboxymethyl)amino}acetic acid, trifluoroacetic acid salt

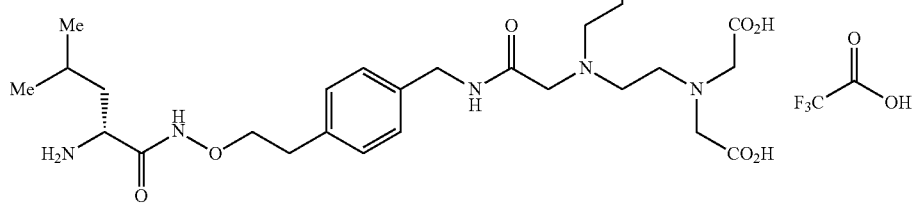

A solution of 2-{bis[2-(bis{[(tert-butyl)oxycarbonyl]methyl}amino)ethyl]amino}acetic acid (51.1 mg, 82.7 µmol), HOBt (12.7 mg, 82.9 µmol) and the product of Part 13G (34.0 mg, 68.9 µmol) in dry DMF (2.00 mL) was successively treated with i-Pr₂NEt (21 µL, 120 µmol) and HBTU (31.4 mg, 82.8 µmol) at 22° C. The resulting solution was stirred 1 h then diluted with EtOAc (15 mL) and successively washed with 0.1 M citric acid (3×10 mL) and saturated aqueous solutions of NaHCO₃ (3×10 mL) and NaCl (10 mL) then dried over MgSO₄, filtered and concentrated in vacuo to a colorless oil which was used without further purification in the subsequent deprotection step.

The protected conjugate (68.9 µmol theoretical) was dissolved in dioxane (0.500 mL) then successively treated with H₂O (2 µL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed under a stream of N₂ and the white solid residue redissolved in H₂O containing 0.1% TFA and 10% MeCN (3.00 mL) then directly purified by HPLC on a Phenomenex Luna C18 column (21.2×250 mm) using a 1%/min gradient from 2-24% MeCN containing 0.1% TFA and 10% H₂O at 20 mL/min. The main product peak eluting at 19 min was collected and lyophilized to a white powder (54.4 mg, 54.5 µmol; 79.2%). $^1$H NMR (DMSO-$d_6$, 600 MHz): δ 11.80 (1H, brs), 8.92 (1H, brt, J=5.7 Hz), 8.28 (2H, brs), 7.24 (2H, AB, $J_{AB}$=8.4 Hz), 7.21 (2H, AB, $J_{AB}$=8.4 Hz), 4.32 (2H, brd, J=5.6 Hz), 4.23 (2H, s), 4.00 (2H, ABXY, $J_{AB}$=9.6 Hz, $J_{AX}$=$J_{AY}$=7.0 Hz, $J_{BX}$=$J_{BY}$=6.7 Hz), 3.66 (1H, brs), 3.50 (8H, s), 3.38 (4H, brt, J=5.7 Hz), 3.05 (4H, brt, J=5.7 Hz), 2.87 (2H, ABXY, $J_{AX}$=$J_{AY}$=7.0 Hz, $J_{BX}$=$J_{BY}$=6.7 Hz), 1.60-1.50 (3H, m), 0.90 (3H, d, J=6.1 Hz), 0.88 (3H, d, J=6.1 Hz). $^{13}$C NMR (DMSO-$d_6$, 151 MHz): δ 172.7, 165.5, 164.6, 158.0 (q, J=31.8 Hz), 136.8, 136.2, 128.8, 127.4, 116.9 (q, J=299 Hz), 75.9, 54.3, 53.8, 52.2, 48.9, 48.6, 42.1, 40.0, 33.4, 23.8, 22.2, 22.0. HRMS calcd for $C_{29}H_{46}N_6O_{11}$ (M+H): 655.3297. Found: 655.3291.

EXAMPLE 14

2-{[2-({[N-({4-[2-((2R)-2-amino-4-phenylbutanoylaminooxy)ethyl]phenyl}methyl)carbamoyl]methyl}{2-[bis(carboxymethyl)amino]ethyl}amino)ethyl](carboxymethyl)amino}acetic acid, trifluoroacetic acid salt

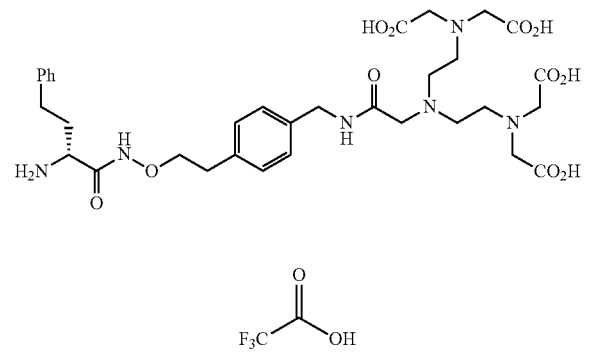 [SMILES: N[C@H](CCc1ccccc1)C(=O)NOCCc1ccc(CNC(=O)CN(CCN(CC(=O)O)CC(=O)O)CCN(CC(=O)O)CC(=O)O)cc1 ; O=C(O)C(F)(F)F]

part A—Preparation of (2R)-N-{2-[4-(aminomethyl)phenyl]ethoxy}-2-[(tert-butoxy)carbonyl-amino]-4-phenylbutanamide, trifluoroacetic acid salt

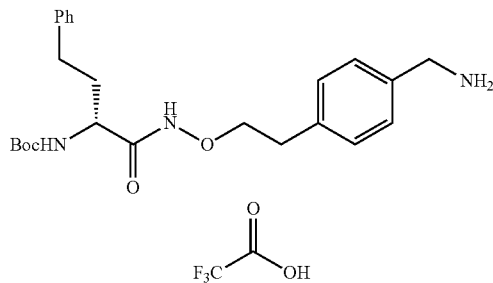

A solution of Boc-DHfe-OH (55.0 mg, 0.197 mmol) in DMF (1.00 mL) was successively treated with HOBt (30.0 mg, 0.196 mmol), i-Pr₂NEt (51 µL, 0.293 mmol) and HBTU (75.0 mg, 0.198 mmol) at 22° C. After 0.25 h, the solution was treated with the product of Part 13F (55.0 mg, 0.163 mmol) in one portion. The resulting solution was stirred 0.5 h then diluted with EtOAc (25 mL) and transferred to a separatory funnel. The EtOAc solution was successively washed with 0.1 M citric acid (3×30 mL) and saturated aqueous solutions of NaHCO₃ (3×30 mL) and NaCl (30 mL) then dried over MgSO₄, filtered and concentrated in vacuo to a colorless oil which was used without further purification in the subsequent deprotection step.

The crude hydroxamate ester (0.163 mmol theoretical) was dissolved in MeOH (1.00 mL) and treated with 10% Pd on carbon (17.4 mg, 16.3 µmol; 10 mol %) in one portion at 22° C. The resulting suspension was sparged with 1 atm H₂, and maintained 1 h. After purging the vessel with N₂, the suspension was filtered through a 0.45 µm Acrodisk then concentrated in vacuo. The residue was redissolved in 1:1 MeCN/H₂O (3.00 mL) then directly purified by HPLC on a Phenomenex Luna C18 column (21.2×250 mm) using a 1%/min gradient from 25-51% MeCN containing 0.1% TFA and 10% H₂O at 20 mL/min. The main product peak eluting at 17 min was collected and lyophilized to a white powder (25.0 mg, 46.2 µmol; 28.3%). $^1$H NMR (DMSO-$d_6$, 600 MHz): δ 11.14 (1H, brs), 8.11 (2H, brs), 7.36 (2H, AB, $J_{AB}$=8.2 Hz), 7.33 (2H, AB, $J_{AB}$=8.2 Hz), 7.26 (2H, dd, J=7.7, 7.4 Hz), 7.18-7.16 (3H, m), 7.08 (1H, brd, J=7.4 Hz), 3.98 (2H, s), 3.97-3.91 (2H, m), 3.75 (1H, brs), 2.88 (2H, brdd, J=6.6, 6.1 Hz), 2.63-2.58 (1H, m), 2.53-2.47 (1H, m), 1.82-1.78 (2H, m), 1.38 (9H, s). HRMS calcd for $C_{24}H_{33}N_3O_4$ (M+H): 428.2544. Found: 428.2542.

part B—Preparation of 2-{[2-({[N-({4-[2-((2R)-2-amino-4-phenylbutanoylaminooxy)ethyl]phenyl}methyl)carbamoyl]methyl}{2-[bis(carboxymethyl)amino]ethyl}amino)-ethyl](carboxymethyl)amino}acetic acid, trifluoroacetic acid salt

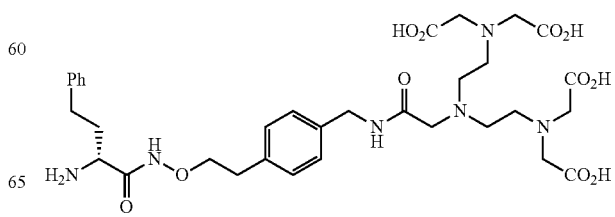

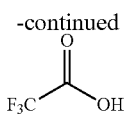

A solution of 2-{bis[2-(bis{[(tert-butyl)oxycarbonyl]methyl}amino)ethyl]amino}acetic acid (31.5 mg, 51.0 µmol), HOBt (7.8 mg, 51 µmol) and the product of Part 14A (23.0 mg, 42.5 µmol) in dry DMF (2.00 mL) was successively treated with i-Pr$_2$NEt (13 µL, 75 µmol) and HBTU (19.3 mg, 50.9 µmol) at 22° C. The resulting solution was stirred 1 h then diluted with EtOAc (15 mL) and successively washed with 0.1 M citric acid (3×10 mL) and saturated aqueous solutions of NaHCO$_3$ (3×10 mL) and NaCl (10 mL) then dried over MgSO$_4$, filtered and concentrated in vacuo to a colorless oil which was used without further purification in the subsequent deprotection step.

The protected conjugate (42.5 µmol theoretical) was dissolved in dioxane (0.500 mL) then successively treated with H$_2$O (2 µL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed under a stream of N$_2$ and the white solid residue redissolved in H$_2$O containing 0.1% TFA and 10% MeCN (3.00 mL) then directly purified by HPLC on a Phenomenex Luna C18 column (21.2×250 mm) using a 1%/min gradient from 7-29% MeCN containing 0.1% TFA and 10% H$_2$O at 20 mL/min. The main product peak eluting at 16 min was collected and lyophilized to a white powder (13.3 mg, 12.7 µmol; 30.0%). $^1$H NMR (DMSO-d$_6$, 600 MHz): δ 11.78 (1H, brs), 8.90 (1H, brt, J=5.6 Hz), 8.35 (2H, brs), 7.30 (2H, dd, J=7.6, 7.6 Hz), 7.25 (2H, AB, J$_{AB}$=7.9 Hz), 7.21 (2H, AB, J$_{AB}$=7.9 Hz), 7.18 (2H, d, J=7.3 Hz), 7.21-7.17 (1H, m), 4.31 (2H, brt, J=5.2 Hz), 4.23 (2H, s), 4.03 (2H, ABXY, J$_{AB}$=9.7 Hz, J$_{AX}$=J$_{AY}$=7.0 Hz, J$_{BX}$=J$_{BY}$=6.7 Hz), 3.68 (1H, brs), 3.49 (8H, s), 3.38 (4H, brt, J=5.5 Hz), 3.04 (4H, brt, J=5.8 Hz), 2.89 (2H, ABXY, J$_{AX}$=J$_{BX}$=J$_{AY}$=J$_{BY}$=6.7 Hz), 2.59 (2H, dd, J=8.5, 8.2 Hz), 2.03-1.93 (2H, m). $^{13}$C NMR (DMSO-d$_6$, 151 MHz): δ 172.7, 165.2, 164.6, 157.9 (q, J=31.8 Hz), 140.2, 136.8, 136.2, 128.8, 128.5, 128.0, 127.4, 126.2, 116.9 (q, J=299 Hz), 76.0, 54.3, 53.8, 52.2, 50.3, 48.6, 42.1, 33.4, 32.7, 30.4. HRMS calcd for C$_{33}$H$_{46}$N$_6$O$_{11}$ (M+H): 703.3297. Found: 703.3289.

EXAMPLE 15

2-{[2-({[N-({4-[2-((2R)-2-amino-3-(2-naphthyl)propanoylaminooxy)ethyl]phenyl}methyl)carbamoyl]methyl}{2-[bis(carboxymethyl)amino]ethyl}amino)ethyl](carboxymethyl)amino}acetic acid, trifluoroacetic acid salt part A—Preparation of (2R)-N-{2-[4-(aminomethyl)phenyl]ethoxy}-2-[(tert-butoxy)carbonyl-amino]-3-(2-naphthyl)propanamide, trifluoroacetic acid salt

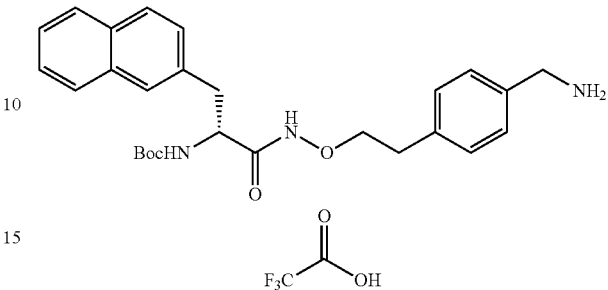

A solution of Boc-DNal-OH (62.0 mg, 0.197 mmol) in DMF (1.00 mL) was successively treated with HOBt (30.0 mg, 0.196 mmol), i-Pr$_2$NEt (51 µL, 0.293 mmol) and HBTU (75.0 mg, 0.198 mmol) at 22° C. After 0.25 h, the solution was treated with the product of Part 13F (55.0 mg, 0.163 mmol) in one portion. The resulting solution was stirred 0.5 h then diluted with EtOAc (25 mL) and transferred to a separatory funnel. The EtOAc solution was successively washed with 0.1 M citric acid (3×30 mL) and saturated aqueous solutions of NaHCO$_3$ (3×30 mL) and NaCl (30 mL) then dried over MgSO$_4$, filtered and concentrated in vacuo to a colorless oil which was used without further purification in the subsequent deprotection step.

The crude hydroxamate ester (0.163 mmol theoretical) was dissolved in MeOH (1.00 mL) and treated with 10% Pd on carbon (17.4 mg, 16.3 µmol; 10 mol %) in one portion at 22° C. The resulting suspension was sparged with 1 atm H$_2$, and maintained 2 h; an additional 0.2 equiv Pd was added after 1 h to ensure complete conversion. After purging the vessel with N$_2$, the suspension was filtered through a 0.45 µm Acrodisk then concentrated in vacuo. The residue was redissolved in 1:1 MeCN/H$_2$O (3.00 mL) then directly purified by HPLC on a Phenomenex Luna C18 column (21.2×250 mm) using a 1%/min gradient from 25-51% MeCN containing 0.1% TFA and 10% H$_2$O at 20 mL/min. The main product peak eluting at 18 min was collected and lyophilized to a white powder (60.8 mg, 0.105 mmol; 64.5%). $^1$H NMR (DMSO-d$_6$, 600 MHz): δ 11.14 (1H, brs), 8.11 (2H, brs), 7.85 (1H, d, J=7.3 Hz), 7.82 (1H, d, J=8.4 Hz), 7.80 (1H, d, J=7.6 Hz), 7.71 (1H, s), 7.48-7.44 (2H, m), 7.41 (1H, d, J=8.1 Hz), 7.33 (2H, AB, J$_{AB}$=7.8 Hz), 7.21 (2H, AB, J$_{AB}$=7.3 Hz), 7.14 (1H, brd, J=7.8 Hz), 4.13-4.09 (1H, m), 3.98 (2H, s), 3.86-3.82 (1H, m), 3.76-3.72 (1H, m), 3.40 (1H, ABXY, J$_{AB}$=13.3 Hz, J$_{AX}$=J$_{AY}$=6.5 Hz), 2.97 (1H, ABXY, J$_{AB}$=13.5 Hz, J$_{BX}$=J$_{BY}$=8.7 Hz), 2.71 (2H, brs), 1.29 (9H, s). HRMS calcd for C$_{27}$H$_{33}$N$_3$O$_4$ (M+H): 464.2544. Found: 464.2538.

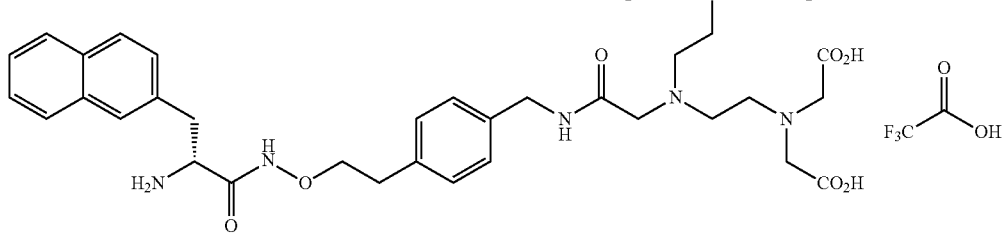

part B—Preparation of 2-{[2-({[N-({4-[2-((2R)-2-amino-3-(2-naphthyl)propanoylaminooxy)-ethyl]phenyl}methyl)carbamoyl]methyl}{2-[bis(carboxymethyl)amino]ethyl}amino)-ethyl](carboxymethyl)amino}acetic acid, trifluoroacetic acid salt

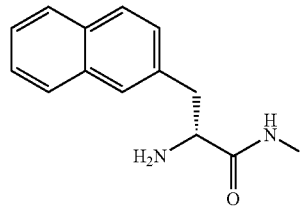
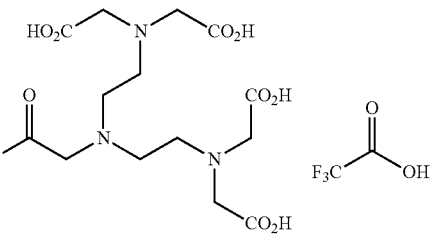

A solution of 2-{bis[2-(bis{[(tert-butyl)oxycarbonyl]methyl}amino)ethyl]amino}acetic acid (46.2 mg, 74.8 μmol), HOBt (11.5 mg, 75.1 μmol) and the product of Part 15A (36.0 mg, 62.3 μmol) in dry DMF (2.00 mL) was successively treated with i-Pr$_2$NEt (19 μL, 110 μmol) and HBTU (28.4 mg, 74.9 μmol) at 22° C. The resulting solution was stirred 1 h then diluted with EtOAc (15 mL) and successively washed with 0.1 M citric acid (3×10 mL) and saturated aqueous solutions of NaHCO$_3$ (3×10 mL) and NaCl (10 mL) then dried over MgSO$_4$, filtered and concentrated in vacuo to a colorless oil which was used without further purification in the subsequent deprotection step.

The protected conjugate (62.3 μmol theoretical) was dissolved in dioxane (0.500 mL) then successively treated with H$_2$O (2 μL) and HCl (2.00 mmol; 0.500 mL of a 4 M solution in dioxane) at 22° C. The resulting pale yellow solution was stirred 18 h, during which time a heavy white precipitate formed. Upon complete deprotection, the volatiles were removed under a stream of N$_2$ and the white solid residue redissolved in H$_2$O containing 0.1% TFA and 10% MeCN (3.00 mL) then directly purified by HPLC on a Phenomenex Luna C18 column (21.2×250 mm) using a 1%/min gradient from 12-32% MeCN containing 0.1% TFA and 10% H$_2$O at 20 mL/min. The main product peak eluting at 20 min was collected and lyophilized to a white powder (36.5 mg, 33.8 μmol; 54.2%). $^1$H NMR (DMSO-d$_6$, 600 MHz): δ 11.55 (1H, brs), 8.90 (1H, brt, J=5.7 Hz), 8.47 (2H, brs), 7.90-7.87 (2H, m), 7.84-7.81 (1H, m), 7.72 (1H, s), 7.50-7.46 (2H, m), 7.38 (1H, brd, J=8.3 Hz), 7.14 (2H, AB, J$_{AB}$=8.0 Hz), 7.00 (2H, AB, J$_{AB}$=8.0 Hz), 4.29 (2H, brd, J=5.5 Hz), 4.23 (2H, s), 3.90 (1H, brs), 3.79 (1H, ABXY, J$_{AB}$=10.0 Hz, J$_{AX}$=J$_{AY}$=7.0 Hz), 3.64 (1H, ABXY, J$_{AB}$=10.0 Hz, J$_{BX}$=J$_{BY}$=6.8 Hz), 3.50 (8H, s), 3.38 (4H, brt, J=5.6 Hz), 3.22 (1H, ABX, J$_{AB}$=13.2 Hz, J$_{AX}$=5.6 Hz), 3.16 (1H, ABX, J$_{AB}$=13.2 Hz, J$_{BX}$=8.6 Hz), 3.05 (4H, brt, J=5.7 Hz), 2.56 (2H, ABXY, J$_{AX}$=J$_{BX}$=J$_{AY}$=J$_{BY}$=6.9 Hz). $^{13}$C NMR (DMSO-d$_6$, 151 MHz): δ 172.7, 164.6, 164.4, 158.0 (q, J=32.9 Hz), 136.6, 136.1, 132.9, 132.3, 132.2, 128.7, 128.1, 127.5, 127.4, 127.4, 127.3, 126.2, 125.9, 116.7 (q, J=297 Hz), 75.7, 54.3, 53.8, 52.2, 51.5, 48.6, 42.1, 37.0, 33.1. HRMS calcd for C$_{36}$H$_{46}$N$_6$O$_{11}$ (M+H): 739.3297. Found: 739.32.

EXAMPLE 16

2-{7-[(N-{[4-({[(1R)-1-(N-methoxycarbamoyl)-3-phenylpropyl]amino}methyl)phenyl]methyl}carbamoyl)methyl]-1,4,7,10-tetraaza-4,10-bis(carboxymethyl)cyclododecyl}acetic acid, trifluoroacetic acid salt

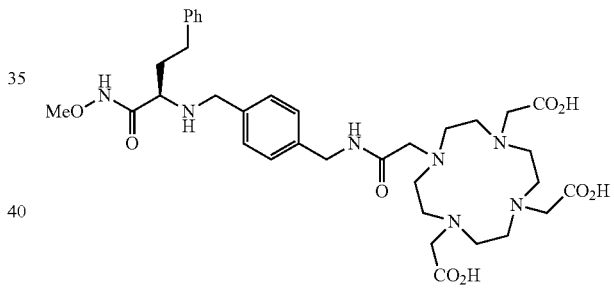

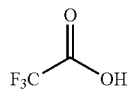

part A—Preparation of (2R)-2-Amino-N-methoxy-4-phenylbutanamide

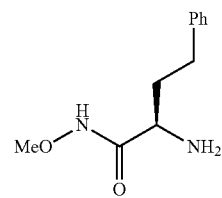

A solution of Boc-DHfe-OH (1.40 g, 5.00 mmol) and HOBt (0.919 g, 6.00 mmol) in dry DMF (25.0 mL) was successively treated with i-Pr₂NEt (2.09 mL, 12.0 mmol) and HBTU (2.28 g, 6.00 mmol) then stirred 0.25 h at 22° C. The resulting solution was treated with MeONH₂·HCl (0.501 g, 6.00 mmol) in one portion, maintained 0.5 h then partitioned between EtOAc and 0.1 M HCl (50 ml each) with transfer to a separatory funnel. The layers separated and the aqueous layer washed with EtOAc (2×50 mL).

The combined EtOAc washes were successively washed with 0.1 M HCl, 0.1 M NaOH and saturated aqueous NaCl (3×50 mL each) then dried over MgSO₄, filtered and concentrated in vacuo to a white solid ($R_f$=0.2 in 1:1 hexanes/EtOAc).

The crude methyl hydroxamate was redissolved in dioxane (75.0 mL) then successively treated with Et₃SiH (799 µL, 5.00 mmol) and HCl (0.100 µmol; 25.0 mL of a 4.0 M solution in dioxane) at 22° C. The resulting solution was stirred 12.5 h then neutralized with 1.0 M NaOH (100 mL), diluted with EtOAc (100 mL) and transferred to a separatory funnel. The layers separated and the aqueous layer exhaustively washed with EtOAc (6×50 mL). The combined EtOAc layers were dried over MgSO₄, filtered and concentrated in vacuo to a colorless oil that was purified by chromatography on silica (40×210 mm) using 9:1 CH₂Cl₂/MeOH containing 1.0% Et₃N ($R_f$=0.1 in 9:1 CH₂Cl₂/MeOH). The main product eluted between 300-420 mL, was collected and concentrated to afford an amorphous white powder (0.659 g, 3.16 mmol; 63.3%). ¹H NMR (DMSO-d₆, 300 MHz): δ 7.30-7.14 (5H, m), 3.58 (3H, s), 3.02 (1H, dd, J=7.5, 6.0 Hz), 2.69-2.50 (2H, m), 1.80 (1H, dddd, J=13.2, 10.1, 6.2, 6.2 Hz), 1.64 (1H, dddd, J=13.4, 10.0, 7.8, 5.8 Hz). ¹³C NMR (DMSO-d₆, 75 MHz): δ 171.6, 141.8, 128.2, 128.2, 125.7, 63.0, 52.4, 36.8, 31.4. HRMS calcd for C₁₁H₁₆N₂O₂ (M+H): 209.1285. Found: 209.1288.

part B—Preparation of N-[(4-formylphenyl)methyl]prop-2-enyloxycarboxamide

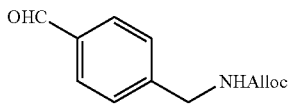

A solution of the product of Part 1B (2.21 g, 10.0 mmol) in dry CH₂Cl₂ (50.0 mL) was treated with Dess-Martin periodinane (5.09 g, 12.0 mmol) in one portion at 22° C. Within one min, rapid dissolution of the oxidant was observed; leading to gentle reflux of the reaction mixture. After 5 min, complete oxidation was observed and the resulting suspension diluted with Et₂O (50 mL). The solids were removed by filtration through a pad of Celite and the filter cake exhaustively washed with Et₂O; final filtrate volume of 500 mL. The combined filtrates were concentrated in vacuo to a pale yellow oil then purified by chromatography on silica (40×265 mm) using a step gradient from 3:2→2:3 hexanes/EtOAc ($R_f$=0.5 in 1:1 hexanes/EtOAc) to afford the pure product as a colorless oil (2.15 g, 9.81 mmol; 98.1%) ¹H NMR (CDCl₃, 600 MHz): δ 10.01 (1H, s), 7.86 (2H, AB, $J_{AB}$=8.1 Hz), 7.47 (2H, AB, $J_{AB}$=7.9 Hz), 5.59 (1H, ddt, J=16.9, 10.7, 5.6 Hz) 5.33 (1H, d, J=17.0 Hz), 5.24 (1H, d, J=10.4 Hz), 5.22 (1H, brs), 4.62 (2H, dt, J=5.7, 1.5 Hz), 4.47 (2H, d, J=6.1 Hz). ¹³C NMR (CDCl₃, 151 MHz): δ 191.8, 156.3, 145.5, 135.7, 132.6, 130.1, 127.8, 117.9, 65.9, 44.7. HRMS calcd for C₁₂H₁₃NO₃ (M+H): 220.0968. Found: 220.0967.

part C—Preparation of (2R)-N-methoxy-4-phenyl-2-[({4-[(prop-2-enyloxycarbonylamino)methyl]phenyl}methyl)amino]butanamide, hydrochloric acid salt

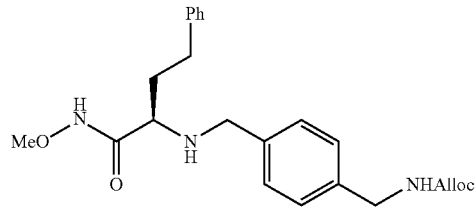

A solution of the product of Parts 16A (0.177 g, 0.850 mmol) and 16B (0.186 g, 0.850 mmol) in dry MeOH (8.50 mL) was cooled to 0° C. then treated with NaCNBH₃ (0.160 g, 2.55 mmol) in one portion. After 1 h, glacial AcOH (0.048 mL, 0.850 mmol) was added to the reaction mixture; a dramatic increase in conversion was observed. The AcOH treatment process was then repeated two additional times during the next 2 h, maintaining a 1 h interval between each equivalent. After 4 h total reaction time, the resulting solution was partitioned between EtOAc and saturated aqueous NaHCO₃ (50 mL each) with transfer to a separatory funnel. The layers separated and the aqueous layer washed with EtOAc (2×50 mL). The combined EtOAc layers were then dried over MgSO₄, filtered and concentrated in vacuo to a pale yellow oil. Purification by chromatography on silica (40×260 mm) using 98:2 EtOAc/MeOH afforded the pure product as a colorless oil. The oil was then redissolved in dry Et₂O (100 mL) and treated with HCl (4.00 mmol; 1.00 mL of a 4.0 M solution in dioxane) at 22° C. The resulting suspension was filtered through a scintered glass funnel of medium porosity and the collected solids exhaustively washed with Et₂O then dried in vacuo to an amorphous white powder (0.253 g, 0.564 mmol; 66.3%). ¹H NMR (DMSO-d₆, 600 MHz): δ 12.20 (1H, s), 10.16 (1H, brs), 9.53 (1H, brs), 7.83 (1H, brt, J=6.1 Hz), 7.51 (2H, AB, $J_{AB}$=8.1 Hz), 7.31-7.27 (4H, m), 7.22-7.18 (3H, m), 5.91 (1H, ddt, J=17.1, 10.6, 5.4 Hz), 5.28 (1H, dq, J=17.2, 1.7 Hz), 5.18 (1H, dq, J=10.5, 1.5 Hz), 4.49 (2H, dt, J=5.4, 1.5 Hz), 4.20 (2H, d, J=6.2 Hz), 4.13-3.99 (2H, m), 3.68 (3H, s), 3.47 (1H, brs), 2.63 (2H, ABXY, $J_{AB}$=13.6 Hz, $J_{AX}$=$J_{BX}$=10.9 Hz, $J_{AY}$=$J_{BY}$=5.9 Hz) 2.24-2.16 (1H, m), 2.10 (1H, dddd, J=13.5, 10.8, 8.6, 6.3 Hz). ¹³C NMR (DMSO-d₆, 151 MHz): δ 163.5, 156.2, 140.8, 140.2, 133.7, 130.3, 129.7, 128.4, 128.1, 127.0, 126.2, 116.9, 64.4, 63.6, 56.7, 48.6, 43.4, 31.3, 30.4.

part D—Preparation of 2-{7-[(N-{[4-({[(1R)-1-(N-methoxycarbamoyl)-3-phenylpropyl]amino}methyl)phenyl]methyl}carbamoyl)methyl]-1,4,7,10-tetraaza-4,10-bis(carboxymethyl)cyclododecyl}acetic acid, trifluoroacetic acid salt

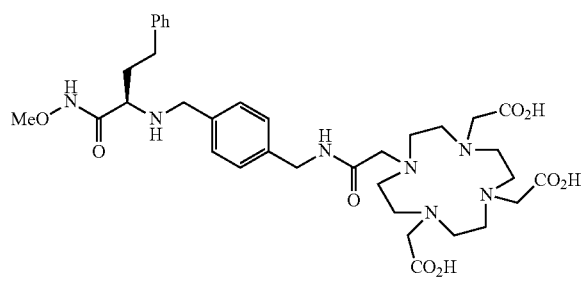

-continued

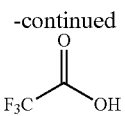

The product of Part 16C (112 mg, 0.250 mmol) was dissolved in 2:1 MeCN/H$_2$O (5.00 mL) and successively treated with 14.2 mg TPPTS (25.0 μmol; 10 mol %), Et$_2$NH (129 μL, 1.25 mmol) and 2.8 mg Pd(OAc)$_2$ (12.5 μmol; 5 mol %) at 22° C. Complete deprotection was observed within 0.25 h. The resulting amber solution was then lyophilized to remove all volatile components.

The solids thus obtained were redissolved in DMF and successively treated with HOBt (45.9 mg, 0.300 mmol), 2-(1,4,7,10-tetraaza-4,7,10-tris {[(tert-butyl)oxycarbonyl]methyl}-cyclododecyl)acetic acid (172 mg, 0.300 mmol), i-Pr$_2$NEt (105 μL, 0.600 mmol) and HBTU (114 mg, 0.300 mmol) at 22° C. After 0.25 h, complete acylation was observed; only trace amounts of regioisomeric and dimeric products formed. The resulting solution was partitioned between EtOAc and H$_2$O (50 mL each) with transfer to a separatory funnel. The layers separated and the aqueous layer washed with EtOAc (2×50 mL). The EtOAc solution was further washed with 0.1 M NaOH (3×50 mL) and saturated aqueous NaCl (3×50 mL each), then dried over MgSO$_4$, filtered and concentrated in vacuo to a pale yellow oil that was used without further purification in the subsequent deprotection step.

The protected conjugate (0.250 mmol theoretical) was dissolved in dioxane (2.50 mL) then successively treated with H$_2$O (23 μL) and HCl (10.0 mmol; 2.50 mL of a 4 M solution in dioxane) at 22° C. The resulting pale yellow solution was stirred 17 h, during which time a heavy white precipitate formed. Upon complete deprotection, the volatiles were removed under a stream of N$_2$ and the white solid residue redissolved in H$_2$O containing 0.1% TFA (8.00 mL) then partially purified by HPLC on a Phenomenex Luna C18 column (21.2×250 mm) using a 2%/min gradient from 0-60% MeCN containing 0.1% TFA and 10% H$_2$O at 20 mL/min. The main product peak eluting at 22 min was collected and lyophilized to a white powder. Final purification was performed using the identical column and method. The main product peak was collected and lyophilized to a white powder (99.0 mg, 93.8 μmol; 37.5%). $^1$H NMR (methanol-d$_4$, 600 MHz): δ 7.44 (2H, AB, J$_{AB}$=8.3 Hz), 7.41 (2H, AB, J$_{AB}$=8.3 Hz), 7.31-7.27 (2H, m), 7.20 (3H, m), 4.40 (2H, s), 4.16 (2H, ABq, J$_{AB}$=13.0 Hz), 3.84-3.74 (9H, brm), 3.78 (3H, s), 3.35 (8H, brs), 3.25 (8H, brs), 2.72-2.62 (2H, m), 2.24-2.13 (2H, m). $^{13}$C NMR (methanol-d$_4$, 151 MHz): δ 165.7, 163.0 (q, J$_{CF}$=34.6 Hz), 142.0, 141.1, 131.7, 130.8, 129.9, 129.8, 129.4, 127.8, 118.3 (q, J$_{CF}$=293 Hz), 65.0, 59.1, 56.2, 55.6 (br), 55.1 (br), 51.5 (br), 51.1, 51.0(br) 44.0, 33.5, 32.2. HRMS calcd for C$_{35}$H$_{51}$N$_7$O$_9$ (M+H): 714.3821. Found: 714.3819.

EXAMPLE 17

2-(7-{[N-({4-[({(1R)-3-phenyl-1-[N-(phenylmethoxy)carbamoyl]propyl}amino)methyl]phenyl}methyl)carbamoyl]methyl}-1,4,7,10-tetraaza-4,10-bis(carboxymethyl)cyclododecyl)acetic acid, trifluoroacetic acid salt

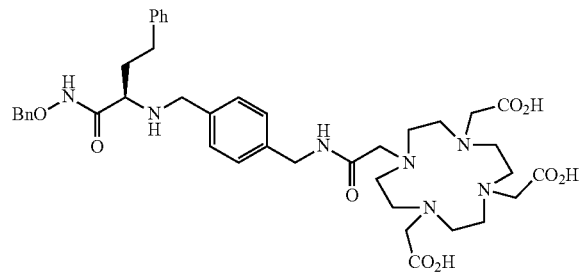

-continued

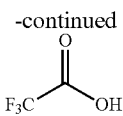

part A—Preparation of (2R)-2-Amino-4-phenyl-N-(phenylmethoxy)butanamide

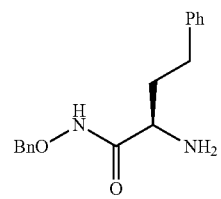 [SMILES: N[C@H](CCc1ccccc1)C(=O)NOCc1ccccc1]

A solution of Boc-DHfe-OH (1.40 g, 5.00 mmol) and HOBt (0.919 g, 6.00 mmol) in dry DMF (25.0 mL) was successively treated with i-Pr$_2$NEt (2.09 mL, 12.0 mmol) and HBTU (2.28 g, 6.00 mmol) then stirred 0.25 h at 22° C. The resulting solution was treated with BnONH$_2$.HCl (0.958 g, 6.00 mmol) in one portion, maintained 0.5 h then partitioned between EtOAc and 0.1 M HCl (50 ml each) with transfer to a separatory funnel. The layers separated and the aqueous layer washed with EtOAc (2×50 mL). The combined EtOAc washes were successively washed with 0.1 M HCl, 0.1 M NaOH and saturated aqueous NaCl (3×50 mL each) then dried over MgSO$_4$, filtered and concentrated in vacuo to a white solid (R$_f$=0.5 in 1:1 hexanes/EtOAc).

The crude benzyl hydroxamate was redissolved in dioxane (75.0 mL) then successively treated with Et$_3$SiH (799 μL, 5.00 mmol) and HCl (0.100 mol; 25.0 mL of a 4.0 M solution in dioxane) at 22° C. The resulting solution was stirred 12.5 h then neutralized with 1.0 M NaOH (100 mL), diluted with EtOAc (100 mL) and transferred to a separatory funnel. The layers separated and the aqueous layer exhaustively washed with EtOAc (3×50 mL). The combined EtOAc layers were dried over MgSO$_4$, filtered and concentrated in vacuo to a colorless oil that was purified by chromatography on silica (50×170 mm) using 9:1 CH$_2$Cl$_2$/MeOH containing 1.0% Et$_3$N(R$_f$=0.3 in 9:1 CH$_2$Cl$_2$/MeOH). The main product eluted between 320-480 mL, was collected and concentrated to afford an amorphous white powder (1.19 g, 4.18 mmol; 83.7%). $^1$H NMR (DMSO-d$_6$, 600 MHz): δ 7.41-7.32 (5H, m), 7.28-7.25 (2H, m), 7.17-7.15 (3H, m), 4.81 (2H, s), 3.02 (1H, dd, J=7.3, 6.1 Hz), 2.55 (2H, ABXY, J$_{AB}$=13.7 Hz, J$_{AX}$=J$_{BX}$=10.3 Hz, J$_{AY}$=5.6 Hz, J$_{BY}$=6.2 Hz), 1.78 (1H, ddt, J=13.2, 10.2, 6.1 Hz), 1.63 (1H, dddd, J=13.1, 10.2, 7.5, 5.6 Hz). $^{13}$C NMR (DMSO-d$_6$, 151 MHz): δ 171.9, 141.8, 136.1, 128.7, 128.2, 128.1, 125.6, 76.6, 52.4, 36.9, 31.4. HRMS calcd for C$_{17}$H$_{20}$N$_2$O$_2$ (M+H): 285.1598. Found: 285.1596.

part B—Preparation of (2R)-4-Phenyl-N-(phenylmethoxy)-2-[({4-[(prop-2-enyloxycarbonylamino)methyl]phenyl}methyl)amino]butanamide, hydrochloric acid salt

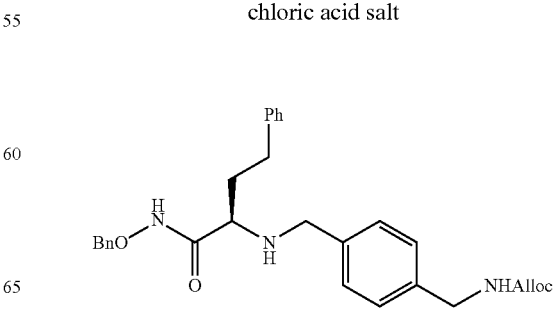

A solution of the product of Parts 17A (0.270 g, 0.950 mmol) and 16B (0.208 g, 0.950 mmol) in dry MeOH (8.50 mL) was cooled to 0° C. then treated with NaCNBH$_3$ (0.179 g, 2.85 mmol) in one portion. After 1 h, glacial AcOH (0.054 mL, 0.950 mmol) was added to the reaction mixture; a dramatic increase in conversion was observed. The AcOH treatment process was then repeated two additional times during the next 2 h, maintaining a 1 h interval between each equivalent. After 4 h total reaction time, the resulting solution was partitioned between EtOAc and saturated aqueous NaHCO$_3$ (50 mL each) with transfer to a separatory funnel. The layers separated and the aqueous layer washed with EtOAc (2×50 mL). The combined EtOAc layers were then dried over MgSO$_4$, filtered and concentrated in vacuo to a pale yellow oil. Purification by chromatography on silica (40×250 mm) using 98:2 EtOAc/MeOH afforded the pure product as a colorless oil. The oil was then redissolved in dry Et$_2$O (100 mL) and treated with HCl (4.00 mmol; 1.00 mL of a 4.0 M solution in dioxane) at 22° C. The resulting suspension was filtered through a scintered glass funnel of medium porosity and the collected solids exhaustively washed with Et$_2$O then dried in vacuo to an amorphous white powder (0.330 g, 0.629 mmol; 66.2%). $^1$H NMR (DMSO-d$_6$, 600 MHz): δ 12.11 (1H, s), 10.14 (1H, brs), 9.52 (1H, brs), 7.83 (1H, brt, J=6.1 Hz), 7.49-7.44 (4H, m), 7.40-7.37 (2H, m), 7.36-7.33 (1H, m), 7.30-7.27 (4H, m), 7.21-7.18 (1H, m), 7.14-7.12 (2H, m), 5.92 (1H, ddt, J=17.2, 10.6, 5.4 Hz), 5.29 (1H, dq, J=17.2, 1.7 Hz), 5.18 (1H, dq, J=10.5, 1.5 Hz), 4.94 (2H, s), 4.49 (2H, dt, J=5.4, 1.5 Hz), 4.20 (2H, d, J=6.2 Hz), 4.02-3.90 (2H, m), 3.42 (1H, brs), 2.50 (2H, ABXY, J$_{AB}$=13.8 Hz, J$_{AX}$=J$_{BX}$=10.9 Hz, J$_{AY}$=J$_{BY}$=5.8 Hz), 2.17-2.11 (1H, m), 2.05 (1H, dddd, J=13.4, 11.1, 8.7, 6.0 Hz). $^{13}$C NMR (DMSO-d$_6$, 151 MHz): δ 163.7, 156.2, 140.8, 140.2, 135.6, 133.7, 130.3, 129.6, 128.8, 128.4(2), 128.3, 128.1, 127.0, 126.1, 116.9, 77.1, 64.4, 56.7, 48.5, 43.4, 31.3, 30.3.

part C—Preparation of 2-(7-{[N-({4-[({(1R)-3-phenyl-1-[N-(phenylmethoxy)carbamoyl]propyl}amino)methyl]phenyl}methyl)carbamoyl]methyl}-1,4,7,10-tetraaza-4,10-bis(carboxymethyl)cyclododecyl)acetic acid, trifluoroacetic acid salt

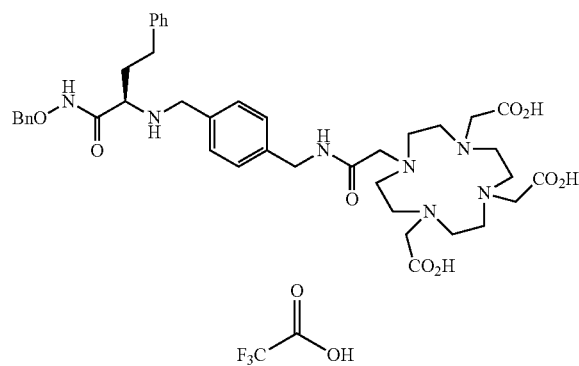

The product of Part 17B (131 mg, 0.250 mmol) was dissolved in 2:1 MeCN/H$_2$O (5.00 mL) and successively treated with 14.2 mg TPPTS (25.0 μmol; 10 mol %), Et$_2$NH (129 μL, 1.25 mmol) and 2.8 mg Pd(OAc)$_2$ (12.5 μmol; 5 mol %) at 22° C. Complete deprotection was observed within 0.25 h. The resulting amber solution was then lyophilized to remove all volatile components.

The solids thus obtained were redissolved in DMF and successively treated with HOBt (45.9 mg, 0.300 mmol), 2-(1,4,7,10-tetraaza-4,7,10-tris {[(tert-butyl)oxycarbonyl]methyl}-cyclododecyl)acetic acid (172 mg, 0.300 mmol), i-Pr$_2$NEt (105 μL, 0.600 mmol) and HBTU (114 mg, 0.300 mmol) at 22° C. After 0.25 h, complete acylation was observed; only trace amounts of regioisomeric and dimeric products formed. The resulting solution was partitioned between EtOAc and H$_2$O (50 mL each) with transfer to a separatory funnel. The layers separated and the aqueous layer washed with EtOAc (2×50 mL). The EtOAc solution was further washed with 0.1 M NaOH (3×50 mL) and saturated aqueous NaCl (3×50 mL each), then dried over MgSO$_4$, filtered and concentrated in vacuo to a pale yellow oil that was used without further purification in the subsequent deprotection step.

The protected conjugate (0.250 mmol theoretical) was dissolved in dioxane (2.50 mL) then successively treated with H$_2$O (23 μL) and HCl (10.0 mmol; 2.50 mL of a 4 M solution in dioxane) at 22° C. The resulting pale yellow solution was stirred 17 h, during which time a heavy white precipitate formed. Upon complete deprotection, the volatiles were removed under a stream of N$_2$ and the white solid residue redissolved in H$_2$O containing 0.1% TFA (8.00 mL) then partially purified by HPLC on a Phenomenex Luna C18 column (21.2×250 mm) using a 2%/min gradient from 0-60% MeCN containing 0.1% TFA and 10% H$_2$O at 20 mL/min. The main product peak eluting at 21 min was collected and lyophilized to a white powder. Final purification was performed using the identical column and method. The main product peak was collected and lyophilized to a white powder (0.110 g, 97.3 μmol; 38.9%). $^1$H NMR (methanol-d$_4$, 600 MHz): δ 7.50-7.48 (2H, m), 7.42-7.35 (6H, m), 7.34-7.30 (1H, m), 7.28-7.24 (2H, m), 7.21-7.17 (1H, m), 7.12-7.09 (2H, m), 4.98 (2H, ABq, J$_{AB}$=11.6 Hz), 4.20 (2H, ABq, J$_{AB}$=15.4 Hz), 3.99 (2H, ABq, J$_{AB}$=12.9 Hz), 3.84 (7H, brs), 3.68 (1H, dd, J=8.5, 5.1 Hz), 3.33 (8H, brs), 3.28 (8H, brs), 2.63 (2H, ABXY, J$_{AB}$=13.8 Hz, J$_{AX}$=J$_{BX}$=10.0 Hz, J$_{AY}$=J$_{BY}$=7.1 Hz) 2.17-2.03 (2H, m). $^{13}$C NMR (methanol-d$_4$, 151 MHz): δ 165.6, 162.93 (q, J$_{CF}$=34.7 Hz), 141.9, 141.1, 136.9, 131.7, 130.8, 130.5, 130.1, 129.8, 129.7, 129.4, 127.7, 118.3 (q, J$_{CF}$=293 Hz), 79.3, 59.3, 56.1, 55.3(br), 55.0 (br), 51.4 (br), 51.1, 44.0, 33.5, 32.1. HRMS calcd for C$_{41}$H$_{55}$N$_7$O$_9$ (M+H): 790.4134. Found: 790.4129.

EXAMPLE 18

2-(4-{[N-({4-[(2R)-2-amino-2-(N-methoxycarbamoyl)ethyl]phenyl}methyl)carbamoyl]methyl}-1,4,7,10-tetraaza-7,10-bis(carboxymethyl)cyclododecyl)acetic acid, trifluoroacetic acid salt

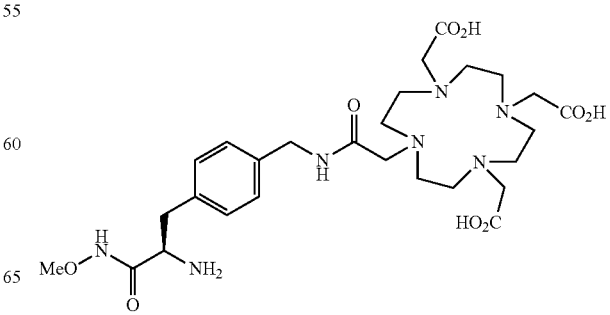

-continued

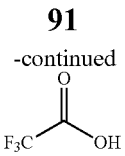

part A—Preparation of (2R)-3-[4-(Aminomethyl) phenyl]-2-[(tert-butoxy)carbonyl-amino]propanoic acid, trifluoroacetic acid salt

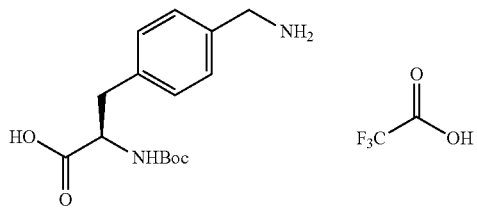 [SMILES: CC(C)(C)OC(=O)N[C@H](Cc1ccc(CN)cc1)C(=O)O ; O=C(O)C(F)(F)F]

(2R)-2-[(tert-Butoxy)carbonylamino]-3-(4-cyanophenyl) propanoic acid (0.581 g, 2.00 mmol) was dissolved in a solution of 28% aqueous. $NH_3$ in MeOH (1:2 v/v; 24 mL), then carefully treated with 0.6 g Raney Ni 2800 under a $N_2$ atmosphere. Using a Parr apparatus, the headspace of the 250 mL reaction vessel was repeatedly sparged with $H_2$, then pressurized to 50 psi and shaken 4 h at 22° C. Upon complete conversion, the headspace was evacuated then repeatedly sparged with $N_2$. The resulting suspension was filtered through a pad of Celite and the filter cake (plus reaction vessel) exhaustively washed with small portions of 1:1 MeCN/$H_2O$; 100 mL final wash volume. The filtrate was neutralized with glacial AcOH, then diluted with $H_2O$ (100 mL) and partially concentrated in vacuo; 175 mL final volume. Lyophilzation of this solution provided the crude product as a white solid suitable for use in the subsequent coupling step. If desired, the crude material may be purified by HPLC on a Phenomenex Luna C18 column (21.2×250 mm) using a 1%/min gradient from 0-40% MeCN containing 0.1% TFA and 10% $H_2O$ at 20 mL/min. The main product peak eluting at 24 min was collected and lyophilized to a white microcrystalline solid. All spectroscopic data of this material was consistent with published reports.

part B—Preparation of 2-(4-{[N-({4-[(2R)-2-amino-2-(N-methoxycarbamoyl)ethyl]phenyl}methyl)carbamoyl]methyl}-1,4,7,10-tetraaza-7,10-bis(carboxymethyl)cyclododecyl)acetic acid, trifluoroacetic acid salt

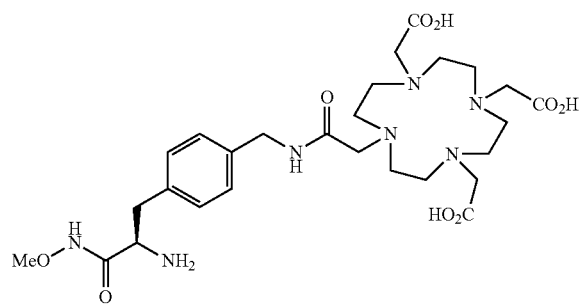

-continued

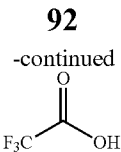

A solution of 2-(1,4,7,10-tetraaza-4,7,10-tris{[(tert-butyl) oxycarbonyl]methyl}-cyclododecyl)acetic acid (68.7 mg, 0.120 mmol) in dry DMF (1.00 mL) was successively treated with HOBt (18.4 mg, 0.120 mmol) and EDC (22.9 mg, 0.120 mmol) at 22° C. After 0.5 h, the solution was treated with the product of Part 18A (40.8 mg, 0.100 mmol) and the resulting mixture stirred 0.5 h. The intermediate conjugate thus obtained was once again activated with EDC (22.9 mg, 0.120 mmol), then stirred 0.5 h before final treatment with MeONH$_2$.HCl (10.0 mg, 0.120 mmol). After 1 h, the resulting mixture was diluted with EtOAc (100 mL) then transferred to a separatory funnel and successively washed with 0.1 M NaOH and saturated aqueous NaCl (3×25 mL each). The EtOAc solution was dried over MgSO$_4$, filtered and concentrated in vacuo to a colorless oil, which was used without further purification in the subsequent deprotection step.

The protected conjugate (0.120 mmol theoretical) was dissolved in dioxane (1.00 mL) then successively treated with $H_2O$ (9 μL) and HCl (4.00 mmol; 1.00 mL of a 4 M solution in dioxane) at 22° C. The resulting pale yellow solution was stirred 14 h, during which time a heavy white precipitate formed. Upon complete deprotection, the volatiles were removed under a stream of $N_2$ and the white solid residue redissolved in $H_2O$ containing 0.1% TFA (8.00 mL) then directly purified by HPLC on a Phenomenex Luna C18 column (21.2×250 mm) using a 1%/min gradient from 0-30% MeCN containing 0.1% TFA and 10% $H_2O$ at 20 mL/min. The main product peak eluting at 11.5 min was collected and lyophilized to a white powder (12.8 mg, 13.4 μmol; 13.4%). $^1$H NMR (methanol-d$_4$, 600 MHz): δ 7.33 (2H, AB, J$_{AB}$=8.0 Hz), 7.22 (2H, AB, J$_{AB}$=8.1 Hz), 4.36 (2H, brs), 3.84 (5H, brs), 3.75-3.66 (4H, brm), 3.57 (3H, s), 3.37 (8H, brs), 3.31 (8H, brs), 3.14-3.06 (2H, m). HRMS calcd for $C_{27}H_{43}N_7O_9$ (M+H): 610.3195. Found: 610.3199.

EXAMPLE 19

2-[7-({N-[(4-{(2R)-2-amino-2-[N-(phenylmethoxy) carbamoyl]ethyl}phenyl)methyl]carbamoyl}methyl)-1,4,7,10-tetraaza-4,10-bis(carboxymethyl)cyclododecyl]acetic acid, trifluoroacetic acid salt

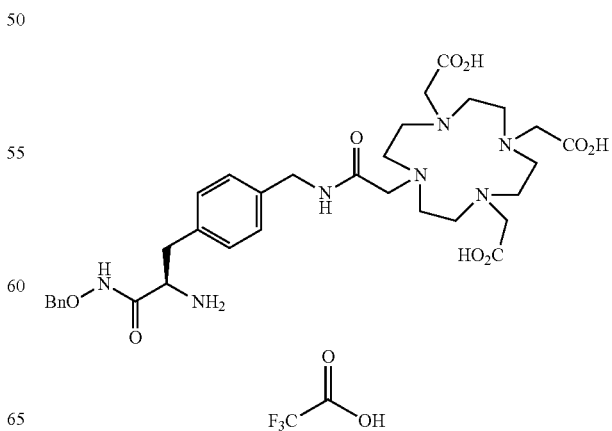

A solution of 2-(1,4,7,10-tetraaza-4,7,10-tris{[(tert-butyl)oxycarbonyl]methyl}-cyclododecyl)acetic acid (68.7 mg, 0.120 mmol) in dry DMF (1.00 mL) was successively treated with HOBt (18.4 mg, 0.120 mmol) and EDC (22.9 mg, 0.120 mmol) at 22° C. After 0.5 h, the solution was treated with the product of Part 18A (40.8 mg, 0.100 mmol) and the resulting mixture stirred 0.5 h. The intermediate conjugate thus obtained was once again activated with EDC (22.9 mg, 0.120 mmol), then stirred 0.5 h before final treatment with BnONH$_2$.HCl (19.2 mg, 0.120 mmol). After 1 h, the resulting mixture was diluted with EtOAc (100 mL) then transferred to a separatory funnel and successively washed with 0.1 M NaOH and saturated aqueous NaCl (3×25 mL each). The EtOAc solution was dried over MgSO$_4$, filtered and concentrated in vacuo to a colorless oil, which was used without further purification in the subsequent deprotection step.

The protected conjugate (0.120 mmol theoretical) was dissolved in dioxane (1.00 mL) then successively treated with H$_2$O (9 μL) and HCl (4.00 mmol; 1.00 mL of a 4 M solution in dioxane) at 22° C. The resulting pale yellow solution was stirred 14 h, during which time a heavy white precipitate formed. Upon complete deprotection, the volatiles were removed under a stream of N$_2$ and the white solid residue redissolved in H$_2$O containing 0.1% TFA (8.00 mL) then partially purified by HPLC on a Phenomenex Luna C18 column (21.2×250 mm) using a 1%/min gradient from 0-40% MeCN containing 0.1% TFA and 10% H$_2$O at 20 mL/min. The main product peak eluting at 21 min was collected and lyophilized to a white powder. Final purification was performed using an identical column combined with a 1%/min gradient from 0-50% MeCN containing 0.1% HCO$_2$H and 10% H$_2$O at 20 mL/min. The main product peak eluting at 14 min was collected and lyophilized to a white powder (8.2 mg, 10.0 μmol; 10.0%). $^1$H NMR (methanol-d$_4$, 600 MHz): δ 7.39 (2H, AB, J$_{AB}$=7.7 Hz), 7.37-7.28 (5H, m), 7.19 (2H, AB, J$_{AB}$=8.0 Hz), 4.70 (2H, ABq, J$_{AB}$=11.0 Hz), 4.41 (2H, ABq, J$_{AB}$=14.8 Hz), 3.84 (1H, brt, J=6.8 Hz), 3.66-3.36 (16H, m), 3.11-2.91 (11H, m). HRMS calcd for C$_{33}$H$_{47}$N$_7$O$_9$ (M+H): 686.3508. Found: 686.3518.

EXAMPLE 20

2-{[2-({[N-({4-[((2R)-2-amino-4-methylpentanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

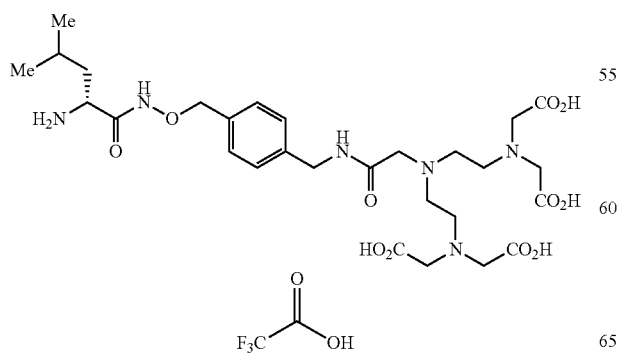

part A—Preparation of N-({4-[(1,3-dioxoisoindolin-2-yloxy)methyl]phenyl}methyl)prop-2-enyloxycarboxamide

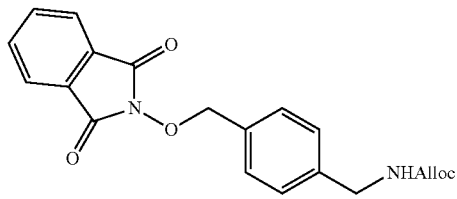

A solution of N-hydroxyphthalimide (3.32 g, 20.3 mmol), the product of Part 1B (3.00 g, 13.6 mmol), and PPh$_3$ (5.33 g, 20.3 mmol) in dry THF (100 mL) was cooled to 0° C. while stirring under N$_2$. ADDP (5.13 g, 20.3 mmol) was added in one portion and the resulting yellow solution warmed to ambient temperature. The solution was stirred for 23 h then heated to 50° C. and maintained 5 h. After cooling to 22° C., the THF removed in vacuo and the residue partitioned between Et$_2$O and saturated aqueous NaHCO$_3$ (500 mL each). The Et$_2$O layer was washed with additional NaHCO$_3$ solution (2×500 mL) then dried over Na$_2$SO$_4$, filtered and concentrated in vacuo to afford the crude product as a yellow solid (7.3 g) that was used without further purification in the subsequent deprotection step. LRMS: 389.2 (100, M+Na), 367.2 (100), 323.2 (25).

part B—Preparation of N-({4-[(aminooxy)methyl]phenyl}methyl)prop-2-enyloxycarboxamide

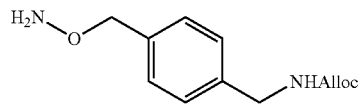

The product of Part 20A (1 g) was dissolved in MeOH (40.0 mL) and hydrazine hydrate (105 mg, 3.3 mmol) added in one portion at 22° C. The mixture was heated to reflux, maintained 0.5 h then cooled to 0° C. using an ice-water bath and maintained 2 h. The white solid precipitate was removed by filtration through a scintered glass funnel and the filtrate concentrated to afford the crude product as a pale yellow solid (794 mg) of suitable purity for use in the subsequent coupling reaction. $^1$H NMR (DMSO-d$_6$, 600 MHz): δ 8.1 (1H, brs), 7.24 (4H, ABq, J$_{AB}$=8.0 Hz), 6.00 (2H, brs), 5.91 (1H, ddt, J=17.4, 10.2, 5.4 Hz), 5.28 (1H, d, J=17.4 Hz), 5.17 (1H, d, J=10.2 Hz), 4.53 (2H, s), 4.49 (2H, dt, J=5.3, 1.5 Hz), 4.18 (2H, d, 6.2 Hz). HRMS calcd for C$_{12}$H$_{16}$N$_2$O$_3$ (M+H): 237.1234. Found: 237.1238.

part C—Preparation of (2R)-2-[(tert-Butoxy)carbonylamino]-4-methyl-N-({4-[(prop-2-enyloxycarbonylamino)methyl]phenyl}methoxy)pentanamide

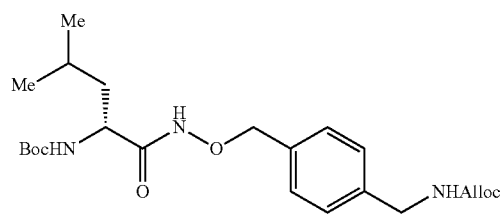

The product of Part 20B (0.200 g, 0.846 mmol) was added to a stirring mixture of Boc-DLeu-OH (254 mg, 1.10 mmol), HOBt (168 mg, 1.10 mmol), HBTU (417 mg, 1.10 mmol), and i-Pr$_2$NEt (678 µL, 3.89 mmol) in DMF at 22° C. The resulting mixture was stirred overnight then concentrated in vacuo and the residue dissolved in EtOAc. The EtOAc solution was successively washed with 0.1 N HCl, 5% aqueous NaHCO$_3$, and saturated aqueous NaCl then dried over Na$_2$SO$_4$, filtered and concentrated in vacuo. The crude material was purified by HPLC on a Phenomenex Luna C18 column (21.2×250 mm) using a 2%/min gradient from 40-80% MeCN containing 0.1% HCO$_2$H and 10% H$_2$O at 20 mL/min. Product containing fractions were pooled and lyophilized to a white microcrystalline powder (224 mg, 0.498 mmol; 58.9%). $^1$H NMR (DMSO-d$_6$, 300 MHz): δ 11.15 (1H, s), 8.04 (1H, t, J=6.9), 7.29 (4H, ABq, J$_{AB}$=8.0 Hz), 6.86 (1H, d, J=7.8 Hz), 5.91 (1H, ddt, J=17.4, 10.6, 5.4 Hz), 5.28 (1H, d, J=16.3 Hz), 5.17 (1H, d, J=10.7 Hz), 4.73 (2H, s), 4.49 (2H, dt, J=5.4, 1.4 Hz), 4.19 (2H, d, J=6.2), 3.81 (1H, AB, J$_{AB}$=7.9 Hz), 1.60-1.25 (3H, m), 1.37 (9H, s), 0.84 (3H, d, J=6.9 Hz), 0.81 (3H, d, J=6.9 Hz). HRMS calcd for C$_{23}$H$_{35}$N$_3$O$_6$ (M+Na): 472.2418. Found: 472.2415.

part D—Preparation of (2R)-N-{[4-(aminomethyl)phenyl]methoxy}-2-[(tert-butoxy)carbonylamino]-4-methylpentanamide, formic acid salt

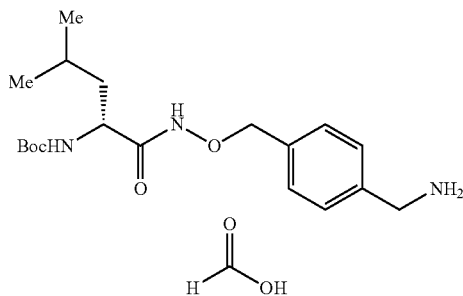

The product of Part 20C (0.200 g, 0.445 mmol) was dissolved in 2:1 MeCN/H$_2$O (8.00 mL) and successively treated with 25.3 mg TPPTS (44.5 µmol; 10 mol %), Et$_2$NH (116 µL, 1.11 mmol), and 5.00 mg Pd(OAc)$_2$ (22.3 µmol; 5 mol %) at 22° C. The resulting yellow solution was stirred 0.5 h, then filtered through a 0.45 µm Acrodisk and directly purified by HPLC on a Phenomenex Luna C18 column (21.2×250 mm) using a 1%/min gradient from 12-37% MeCN containing 0.1% HCO$_2$H and 10% H$_2$O at 20 mL/min. Product-containing fractions were pooled and lyophilized to afford a white microcrystalline powder (113 mg, 0.275 mmol; 61.7%). $^1$H NMR (DMSO-d$_6$, 600 MHz): δ 8.32 (1H, s), 7.37 (4H, ABq, J$_{AB}$=8.4 Hz), 6.90 (1H, d, J=7.9 Hz), 4.75 (2H, s), 3.85 (2H, s), 3.82 (1H, AB, J$_{AB}$=8.4 Hz), 1.46-1.56 (1H, m), 1.38 (9H, s), 1.46-1.36 (1H, m), 1.36-1.26 (1H, m), 0.85 (3H, d, J=6.5 Hz), 0.82 (3H, d, J=6.2 Hz). LRMS: 366.2 (100, M+H), 731.5 (25).

part E—Preparation of (tert-Butyl 2-[(2-{[(N-{[4-({(2R)-2-[(tert-butoxy)carbonylamino]-4-methylpentanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

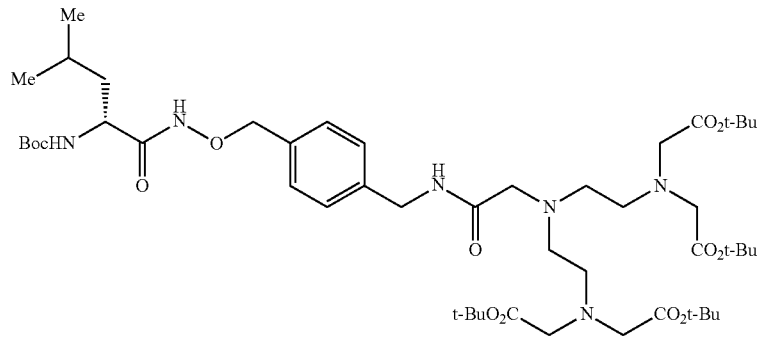

A solution of 2-{bis[2-(bis{[(tert-butyl)oxycarbonyl]methyl}amino)ethyl]amino}acetic acid (102 mg, 0.166 mmol), HOBt (22.4 mg, 0.166 mmol) and the product of Part 20D (55.0 mg, 0.150 mmol) in dry DMF (2.00 mL) was successively treated with i-Pr$_2$NEt (115 µL, 0.662 mmol) and HBTU (63.0 mg, 0.166 mmol) at 22° C. The resulting solution was stirred 18 h then heated to 50° C. and maintained 0.5 h. After cooling to 22° C., all volatiles were removed in vacuo and the residue redissolved in EtOAc. The EtOAc solution was successively washed with 0.1 N HCl, saturated aqueous solutions of NaHCO$_3$, and NaCl then dried over Na$_2$SO$_4$, filtered and concentrated in vacuo to a pale yellow oil, which was used without further purification in the subsequent deprotection step. LRMS: 966.0 (100, M+H), 433.6 (60).

part F—Preparation of 2-{[2-({[N-({4-[((2R)-2-amino-4-methylpentanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

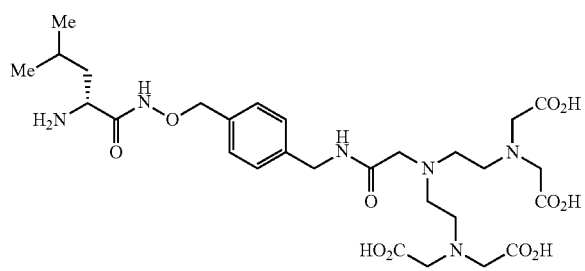

-continued

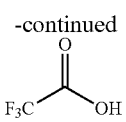

The product of Part 20E (0.150 mmol theoretical) was dissolved in 3:2 TFA/CH$_2$Cl$_2$ (3.00 mL) at 22° C. then stirred overnight. Upon complete deptrotection, all volatiles were removed in vacuo and the residue purified by HPLC on a Phenomenex Luna C18 column (21.2×250 mm) using a 2%/min gradient from 0-30% MeCN containing 0.1% TFA and 10% H$_2$O at 20 mL/min. Product-containing fractions were pooled and lyophilized to afford a white microcrystalline powder (85.0 mg, 86.5 μmol; 57.7%). $^1$H NMR (DMSO-d$_6$, 600 MHz) δ 11.76 (1H, s), 8.97 (1H, t, J=5.7 Hz), 8.25 (3H, brs), 7.35 (4H, ABq, J$_{AB}$=8.1 Hz), 4.82 (2H, s), 4.37 (2H, d, J=5.7 Hz), 4.27 (2H, s), 3.50 (9H, brs), 3.38 (4H, t, J=5.6 Hz), 3.06 (4H, t, J=5.8 Hz), 1.54-1.47 (3H, m), 0.85 (6H, d, J=5.5 Hz). $^{13}$C NMR (DMSO-d$_6$, 151 MHz): δ 172.5, 165.4, 164.6, 138.5, 134.0, 128.8, 127.0, 76.7, 54.1, 53.6, 52.0, 48.7, 48.4, 41.8, 23.4, 22.0, 21.8. HRMS calcd for C$_{28}$H$_{44}$N$_6$O$_{11}$ (M+H): 641.3141. Found: 641.3450.

EXAMPLE 21

2-{[2-({[N-({4-[((2R)-2-amino-3-(2-naphthyl)pro-panoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

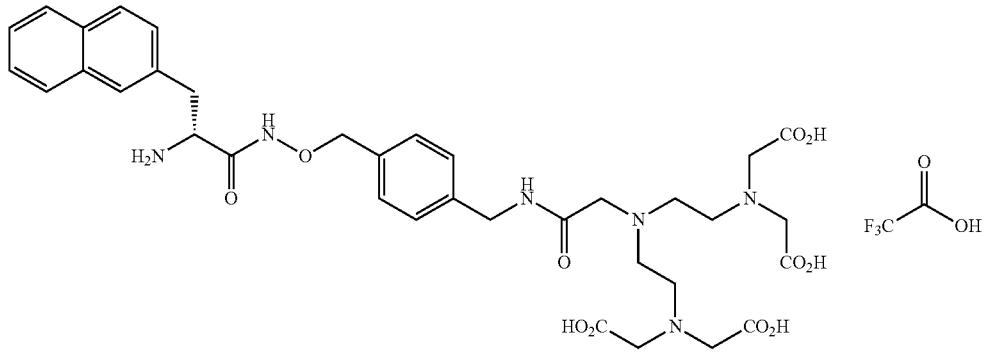 [SMILES: N[C@H](Cc1ccc2ccccc2c1)C(=O)NOCc1ccc(CNC(=O)CN(CCN(CC(=O)O)CC(=O)O)CCN(CC(=O)O)CC(=O)O)cc1 ; O=C(O)C(F)(F)F]

part A—Preparation of (R)-Allyl 4-(9,9-dimethyl-5-(naphthalen-2-ylmethyl)-4,7-dioxo-2,8-dioxa-3,6-diazadecyl)benzylcarbamate

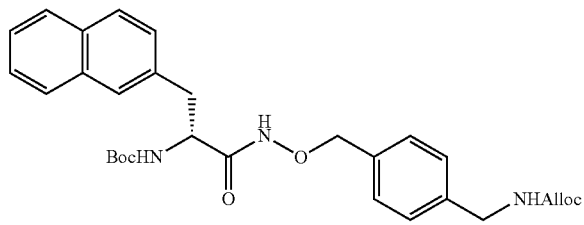

Prepared as described in Part 20C, using Boc-DNal-OH (126 mg, 0.235 mmol; 27.8%). $^1$H NMR (DMSO-d$_6$, 600 MHz): δ 11.20 (1H, s), 7.86 (1H, d, J=8.3 Hz), 7.81 (2H, t, J=7.2 Hz), 7.75 (1H, t, J=5.7 Hz), 7.71 (1H, s), 7.44-7.50 (2H, m), 7.41 (1H, d, J=8.6 Hz), 7.22 (4H, ABq, J$_{AB}$=8.1 Hz), 7.10 (1H, d, J=8.2 Hz), 5.91 (1H, ddd, J=17.4, 10.7, 5.5 Hz), 5.28 (1H, d, J=17.3 Hz), 5.17 (1H, d, J=10.3 Hz), 4.62 (2H, ABq, J$_{AB}$=11.1 Hz), 4.49 (2H, d, J=5.3 Hz), 4.18 (2H, d, J=6.2 Hz), 4.11 (1H, ABq, J$_{AB}$=8.4 Hz), 2.99 (2H, AB, J$_{AB}$=7.8 Hz), 1.29 (9H, s). $^{13}$C NMR (DMSO-d$_6$, 151 MHz): δ 168.3, 156.1, 155.1, 139.9, 135.4, 133.7, 132.9, 131.8, 128.8, 127.7, 127.5, 127.4, 127.3, 126.8, 125.9, 125.4, 116.9, 78.0, 76.5, 64.3, 53.5, 43.5, 37.7, 28.1. HRMS calcd for C$_{30}$H$_{35}$N$_3$O$_6$ (M+H): 556.2418. Found: 556.2410.

part B—Preparation of (2R)-N-{[4-(aminomethyl)phenyl]methoxy}-2-[(tert-butoxy)carbonylamino]-3-(2-naphthyl)propanamide, formic acid salt

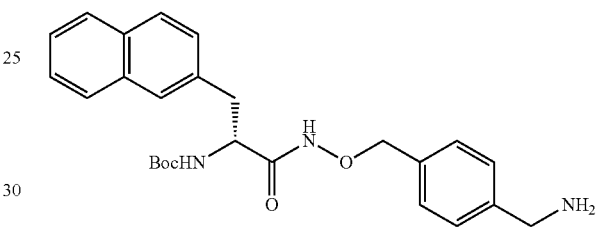

-continued

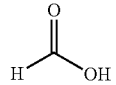

Prepared as described in Part 20D (69.0 mg, 0.139 mmol; 60.3%). $^1$H NMR (DMSO-d$_6$, 600 MHz): δ 8.33 (1H, s), 7.86 (1H, d, J=7.8 Hz), 7.82 (1H, t, J=8.3 Hz), 7.72 (1H, s), 7.44-7.50 (2H, m), 7.42 (1H, d, J=8.2 Hz), 7.31 (4H, ABq, J$_{AB}$=7.9 Hz), 7.12 (1H, d, J=7.1 Hz), 4.62 (2H, ABq, J$_{AB}$=10.8 Hz), 4.12 (1H, m), 3.82 (2H, s), 2.91-3.06 (2H, m), 1.29 (9H, s). LRMS: 450.6 (100, M+H).

part C—Preparation of tert-Butyl 2-[(2-{[(N-{[4-({(2R)-2-[(tert-butoxy)carbonylamino]-3-(2-naphthyl)propanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

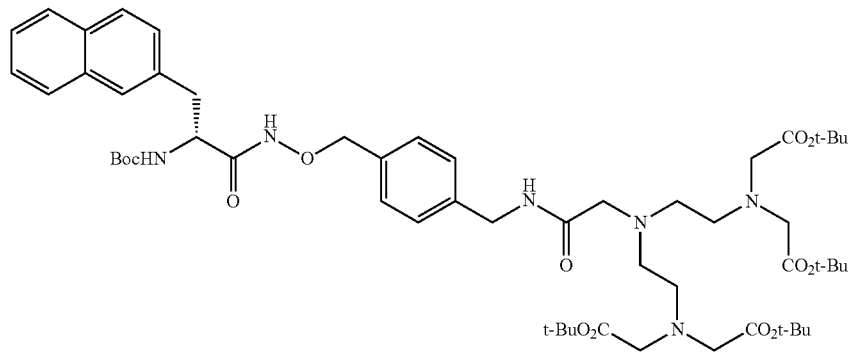

Prepared as described in Part 20E. LRMS: 1050.0 (100, M+H), 618.8 (80), 475.6 (45).

part D—Preparation of 2-{[2-({[N-({4-[((2R)-2-amino-3-(2-naphthyl)propanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

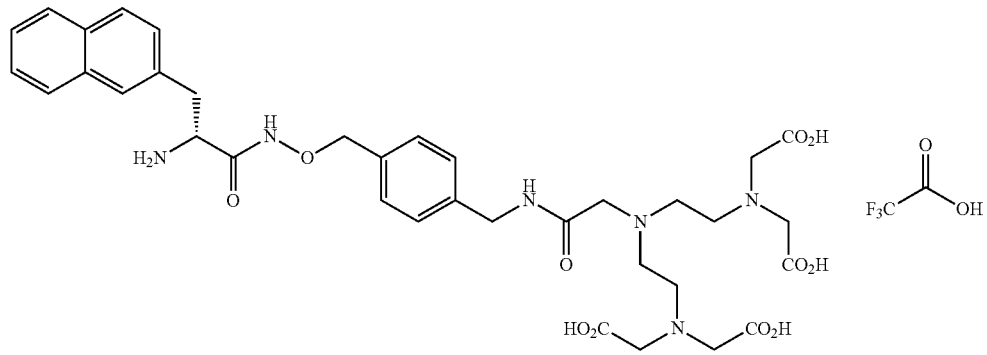 [SMILES: N[C@H](Cc1ccc2ccccc2c1)C(=O)NOCc1ccc(CNC(=O)CN(CCN(CC(=O)O)CC(=O)O)CCN(CC(=O)O)CC(=O)O)cc1 ; O=C(O)C(F)(F)F]

Prepared as described in Part 20F (35.0 mg, 32.8 μmol; 43.2%). $^1$H NMR (DMSO-$d_6$, 300 MHz): δ 11.62 (1H, s), 8.95 (1H, t, J=5.6 Hz), 8.44 (3H, brs), 7.82-7.95 (3H, m), 7.74 (1H, s), 7.56-7.47 (2H, m), 7.37 (1H, d, J=8.8 Hz), 7.17 (4H, ABq $J_{AB}$=8.1 Hz), 4.55 (2H, AB, $J_{AB}$=11.0 Hz), 4.33 (2H, d, J=5.7 Hz), 4.26 (2H, s), 3.83-3.94 (1H, m), 3.51 (8H, s), 3.39 (4H, t, J=5.1 Hz), 3.18 (2H, d, J=7.2 Hz), 3.06 (4H, t, J=4.9 Hz). $^{13}$C NMR (DMSO-$d_6$, 151 MHz): δ 172.7, 164.8, 164.7, 138.7, 134.1, 132.9, 132.3, 132.2, 128.9, 128.2, 128.1, 127.6, 127.5, 127.4, 127.2, 126.3, 125.9, 113.8, 77.0, 54.3, 53.9, 52.2, 51.6, 48.6. HRMS calcd for $C_{35}H_{44}N_6O_{11}$ (M+H): 725.3141. Found: 725.3141.

EXAMPLE 22

2-{[2-({[N-({4-[((2R)-2-amino-3-phenylpropanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

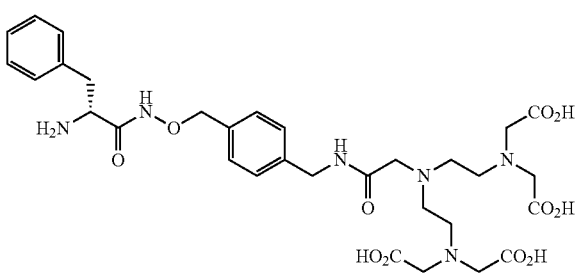

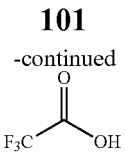

part A—Preparation of (2R)-2-[(tert-Butoxy)carbonylamino]-3-phenyl-N-({4-[(prop-2-enyloxycarbonylamino)methyl]phenyl}methoxy)propanamide

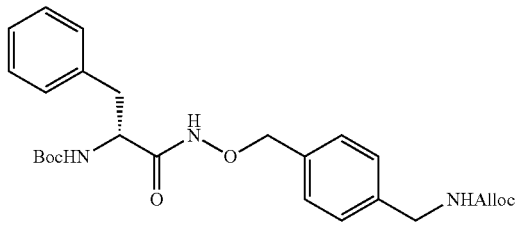

Prepared as described in Part 20C, using Boc-DPhe-OH (88.0 mg, 0.182 mmol; 21.5%). $^1$H NMR (DMSO-$d_6$, 600 MHz): δ 11.19 (1H, s), 7.76 (1H, t, J=4.2 Hz), 7.32-7.16 (9H, m), 7.02 (1H, d, J=8.3 Hz), 5.91 (1H, ddd, J=17.5, 10.5, 5.4 Hz), 5.28 (1H, d, J=17.1 Hz), 5.17 (2H, d, J=11.5 Hz), 4.65 (2H, ABq, $J_{AB}$=10.7 Hz), 4.49 (2H, d, J=5.3 Hz), 4.19 (2H, d, J=6.2 Hz), 4.00 (1H, ABq, $J_{AB}$=8.7 Hz), 2.74-2.87 (2H, m), 1.32 (9H, s). HRMS calcd for $C_{26}H_{33}N_3O_6$ (M+H): 506.2262. Found 506.2254.

part B—Preparation of (2R)-N-{[4-(aminomethyl)phenyl]methoxy}-2-[(tert-butoxy)carbonylamino]-3-phenylpropanamide, formic acid salt

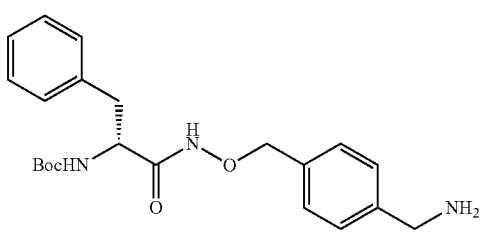

Prepared as described in Part 20D (45.0 mg, 0.101 mmol; 57.3%). $^1$H NMR (DMSO-$d_6$, 600 MHz): δ 8.33 (1H, s), 7.35 (4H, ABq, $J_{AB}$=8.3 Hz), 7.30-7.17 (5H, m), 7.03 (1H, d, J=8.4 Hz), 4.66 (2H, ABq, $J_{AB}$=10.6 Hz), 3.98-4.04 (1H, m), 3.83 (2H, s), 2.85 (1H, dd, J=13.7, 5.8 Hz), 2.78 (1H, dd, J=13.4, 9.5 Hz), 1.32 (9H, s). LCMS: 400.5 (100, M+H).

part C—Preparation of tert-Butyl 2-[(2-{[(N-{[4-({(2R)-2-[(tert-butoxy)carbonylamino]-3-phenylpropanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

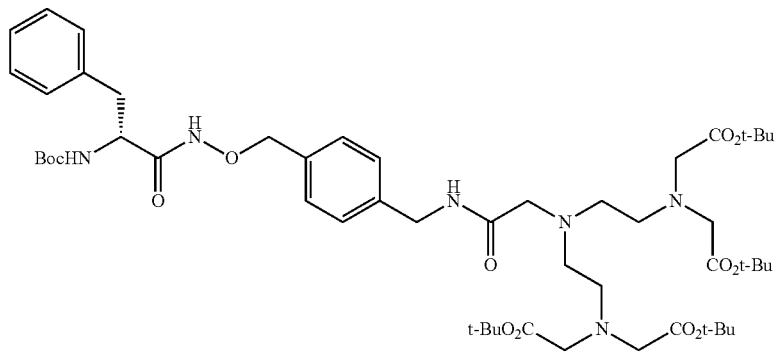

Prepared as described in Part 20E. LRMS: 1000.0 (100, M+H).

part D—Preparation of 2-{[2-({[N-({4-[((2R)-2-amino-3-phenylpropanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

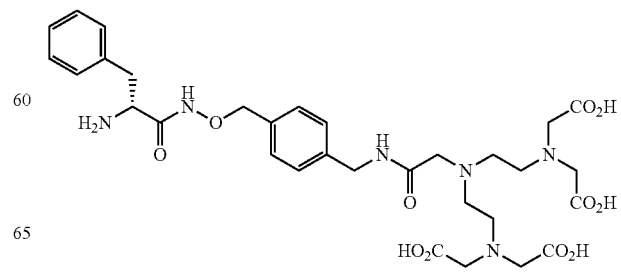

Prepared as described in Part 20F (60.0 mg, 59.0 µmol; 59.7%). $^1$H NMR (DMSO-$d_6$, 300 MHz): δ 11.62 (1H, s), 8.98 (1H, t, J=5.8 Hz), 8.43 (3H, brs), 7.38-7.19 (9H, m), 4.60 (2H, ABq, $J_{AB}$=10.9 Hz), 4.36 (2H, d, J=5.6 Hz), 4.27 (2H, s), 3.84 (1H, m), 3.51 (8H, s), 3.39 (4H, t, J=5.1 Hz), 3.06 (4H, t, J=6.0 Hz), 3.01 (2H, d, J=6.7 Hz). $^{13}$C NMR (DMSO-$d_6$, 151 MHz): δ 172.7, 164.8, 164.6, 138.7, 134.7, 134.1, 129.4, 129.0, 128.6, 127.3, 77.0, 54.3, 53.9, 52.2, 51.5, 48.7, 42.0, 38.6. HRMS calcd for $C_{31}H_{42}N_6O_{11}$ (M+Na): 697.2804. Found: 697.2824.

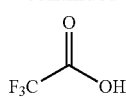

EXAMPLE 23

2-(7-{[N-({4-[((2R)-2-amino-4-methylpentanoylaminooxy)methyl]phenyl}methyl)carbamoyl]methyl}-1,4,7,10-tetraaza-4,10-bis(carboxymethyl)cyclododecyl)acetic acid, trifluoracetic acid salt

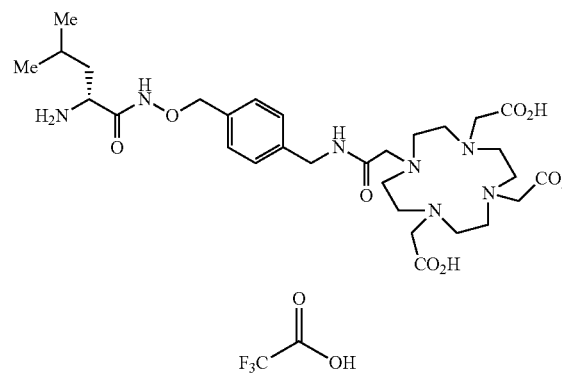

part A—Preparation of tert-Butyl 2-{7-[(N-{[4-({(2R)-2-[(tert-butoxy)carbonylamino]-4-methylpentanoylaminooxy}methyl)phenyl]methyl}carbamoyl)methyl]-1,4,7,10-tetraaza-4,10-bis{[(tert-butyl)oxycarbonyl]methyl}cyclododecyl}acetate

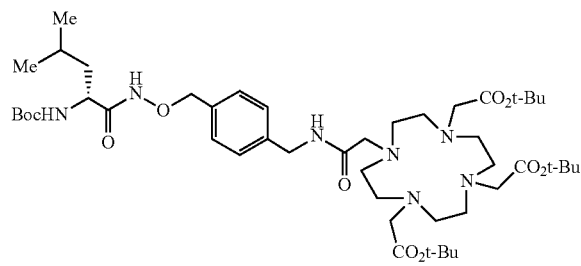 [SMILES: CC(C)C[C@@H](NC(=O)OC(C)(C)C)C(=O)NOCc1ccc(CNC(=O)CN2CCN(CC(=O)OC(C)(C)C)CCN(CC(=O)OC(C)(C)C)CCN(CC(=O)OC(C)(C)C)CC2)cc1]

A solution of 2-(1,4,7,10-tetraaza-4,7,10-tris{[(tert-butyl)oxycarbonyl]methyl}-cyclododecyl)acetic acid (128 mg, 0.224 mmol) in dry DMF (5.00 mL) was successively treated with HOBt (30.3 mg, 0.224 mmol), HBTU (84.9 mg, 0.224 mmol) and i-Pr$_2$NEt (146 µL, 0.840 mmol) at 22° C. After 0.25 h, the solution was treated with the product of Part 20D (55.0 mg, 0.134 mmol) and i-Pr$_2$NEt (146 µL, 0.840 mmol) then stirred overnight. After 24 h, the reaction was heated to 50° C., maintained 5 h then concentrated in vacuo and the residue dissolved in EtOAc. The EtOAc solution was successively washed with 0.1 N HCl, saturated aqueous solutions of NaHCO$_3$, and NaCl then dried over Na$_2$SO$_4$, filtered and concentrated in vacuo to a pale yellow oil, which was used without further purification in the subsequent deprotection step. LRMS: 921.0 (100, M+H), 411.2 (65).

part B—Preparation of 2-(7-{[N-({4-[((2R)-2-amino-4-methylpentanoylaminooxy)methyl]phenyl}methyl)carbamoyl]methyl}-1,4,7,10-tetraaza-4,10-bis(carboxymethyl)cyclododecyl)acetic acid, trifluoracetic acid salt

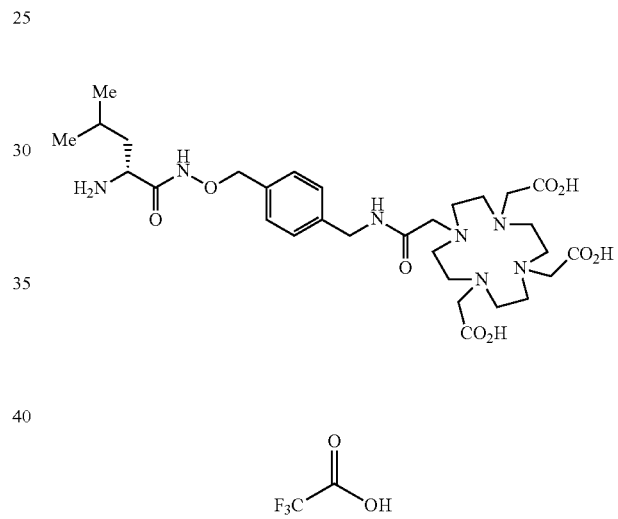

The product of Part 23A (0.134 mmol theoretical) was dissolved in dioxane (3.00 mL) then successively treated with H$_2$O (14 µL) and HCl (12.0 mmol; 3.00 mL of a 4 M solution in dioxane) at 22° C. The resulting pale yellow solution was stirred overnight then all volatiles removed under reduced pressure and the residue directly purified by HPLC on a Phenomenex Luna C18 column (21.2×250 mm) using a 0.875%/min gradient from 0-35% MeCN containing 0.1% TFA and 10% H$_2$O at 20 mL/min. Product-containing fractions were pooled and lyophilized to a white microcrystalline powder (63.0 mg, 63.4 µmol; 47.3%). $^1$H NMR (DMSO-$d_6$, 600 MHz): 9.01 (1H, t, J=5.4 Hz), 7.42 (4H, ABq, $J_{AB}$=8.0 Hz), 4.98 (2H, s), 4.49 (2H, d, J=5.1 Hz), 3.95 (1H, t, J=6.7 Hz), 3.81 (4H, s), 3.80 (2H, s), 3.63 (2H, s), 3.15 (12H, s), 2.99 (4H, s), 1.80-1.66 (3H, m), 0.87 (3H, d, J=6.1 Hz), 0.85 (3H, d, J=6.1 Hz). HRMS calcd for $C_{30}H_{49}N_7O_9$ (M+H): 652.3665. Found: 652.3669.

EXAMPLE 24

2-(7-{[N-({4-[((2R)-2-amino-3-(2-naphthyl)propanoylaminooxy)methyl]phenyl}methyl)carbamoyl]methyl}-1,4,7,10-tetraaza-4,10-bis(carboxymethyl)cyclododecyl)acetic acid, trifluoroacetic acid salt

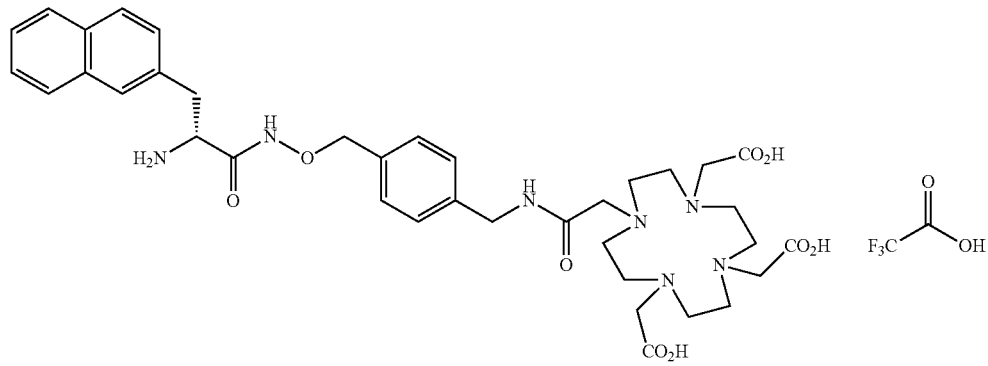 [SMILES: N[C@H](Cc1ccc2ccccc2c1)C(=O)NOCc1ccc(CNC(=O)CN2CCN(CC(=O)O)CCN(CC(=O)O)CCN(CC(=O)O)CC2)cc1 ; O=C(O)C(F)(F)F]

part A—Preparation of tert-Butyl 2-{7-[(N-{[4-({(2R)-2-[(tert-butoxy)carbonylamino]-3-(2-naphthyl)propanoylaminooxy}methyl)phenyl]methyl}carbamoyl)methyl]-1,4,7,10-tetraaza-4,10-bis{[(tert-butyl)oxycarbonyl]methyl}cyclododecyl}acetate

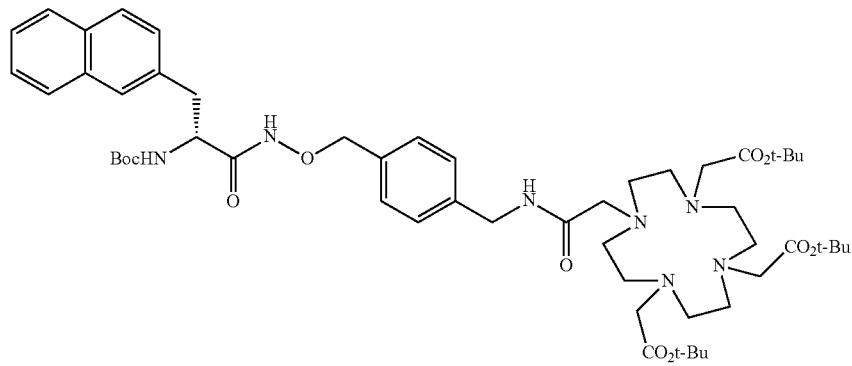 [SMILES: CC(C)(C)OC(=O)CN1CCN(CC(=O)NCc2ccc(CONC(=O)[C@@H](Cc3ccc4ccccc4c3)NC(=O)OC(C)(C)C)cc2)CCN(CC(=O)OC(C)(C)C)CCN(CC(=O)OC(C)(C)C)CC1]

Prepared as described in Part 23A. LRMS: 1005.0 (60, M+H), 453.2 (100).

part B—Preparation of 2-(7-{[N-({4-[((2R)-2-amino-3-(2-naphthyl)propanoylaminooxy)methyl]phenyl}methyl)carbamoyl]methyl}-1,4,7,10-tetraaza-4,10-bis(carboxymethyl)cyclododecyl)acetic acid, trifluoroacetic acid salt

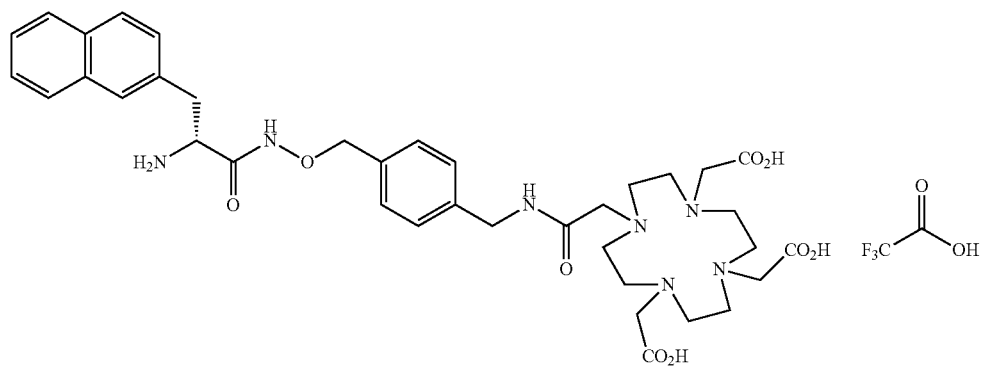 [SMILES: N[C@H](Cc1ccc2ccccc2c1)C(=O)NOCc1ccc(CNC(=O)CN2CCN(CC(=O)O)CCN(CC(=O)O)CCN(CC(=O)O)CC2)cc1 ; O=C(O)C(F)(F)F]

Prepared as described in Part 23B (28.6 mg, 26.5 μmol; 39.9%). $^1$H NMR (DMSO-$d_6$, 600 MHz): δ 8.98 (1H, t, J=5.8 Hz), 7.89-7.79 (5H, m), 7.52 (2H, d, J=8.6 Hz), 7.53-7.49 (2H, m), 7.33-7.20 (4H, m), 4.79 (2H, ABq, $J_{AB}$=11.6 Hz), 4.45 (2H, s), 4.38 (2H, s), 3.80-3.78 (4H, m), 3.59 (1H, s), 3.44 (2H, d, J=7.1 Hz), 3.20-3.09 (12H, m), 2.96 (4H, s). HRMS calcd for $C_{37}H_{49}N_7O_9$ (M+H): 736.3665. Found: 736.3663.

Example 25

2-{[2-({[N-({4-[((2R)-2-amino-3-indol-2-ylpropanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

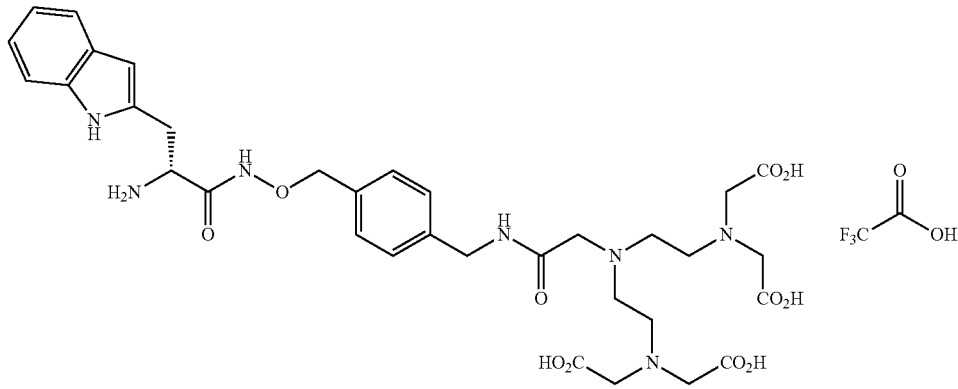 [SMILES: N[C@H](Cc1cc2ccccc2[nH]1)C(=O)NOCc1ccc(CNC(=O)CN(CCN(CC(=O)O)CC(=O)O)CCN(CC(=O)O)CC(=O)O)cc1 ; O=C(O)C(F)(F)F]

part A—Preparation of (2R)-2-[(tert-Butoxy)carbonylamino]-3-indol-2-yl-N-({4-[(prop-2-enyloxycarbonylamino)methyl]phenyl}methoxy)propanamide

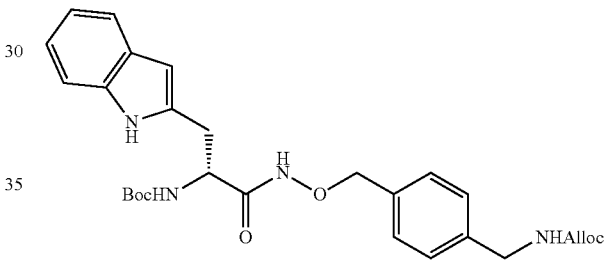

Prepared as described in Part 20C, using Boc-DTrp-OH. LRMS: 423.5 (100, M+H-Boc), 545.5 (15, M+Na).

part B—Preparation of (2R)-N-{[4-(aminomethyl)phenyl]methoxy}-2-[(tert-butoxy)carbonylamino]-3-indol-2-ylpropanamide, formic acid salt

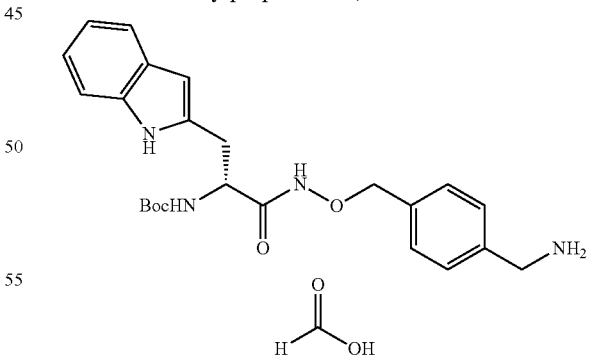

Prepared as described in Part 20D (154 mg, 0.318 mmol; 43.4%). $^1$H NMR (DMSO-$d_6$, 600 MHz): δ 11.22 (1H, brs), 10.80 (1H, s), 8.26 (1H, s), 7.58 (1H, d, J=7.7 Hz), 7.36 (1H, d, J=8.0 Hz), 7.31 (4H, ABq, $J_{AB}$=8.3 Hz), 7.12 (1H, s), 7.05 (1H, t, J=7.5 Hz), 6.97 (1H, t, J=7.5 Hz), 6.91 (1H, d, J=8.1 Hz), 4.64 (2H, ABq, $J_{AB}$=11.0 Hz), 4.04 (1H, AB, $J_{AB}$=7.9 Hz), 3.84 (2H, s), 2.99 (1H, dd, J=14.3, 5.9 Hz), 2.90 (1H, dd, J=14.4, 8.8 Hz), 1.33 (9H, s). HRMS calcd for $C_{24}H_{30}N_4O_4$ (M+Na): 461.259. Found: 461.259.

part C—Preparation of tert-Butyl 2-[(2-{[(N-{[4-({(2R)-2-[(tert-butoxy)carbonylamino]-3-indol-2-ylpropanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

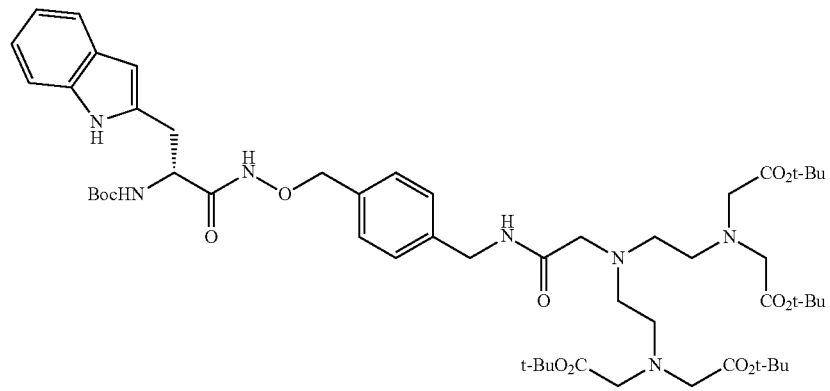

Prepared as described in Part 20E to afford the crude product which was used without purification in the next step. LRMS (m/z): 1039.0 (100%, [M+H]$^+$)

part D—Preparation of 2-{[2-({[N-({4-[((2R)-2-amino-3-indol-2-ylpropanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

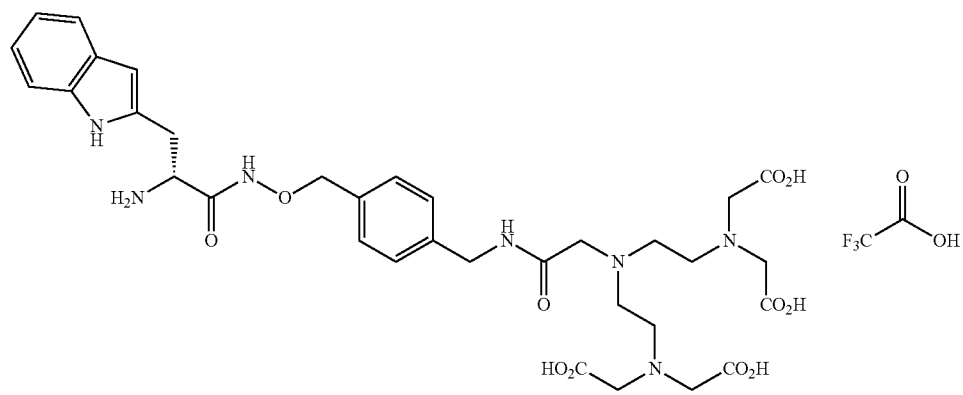 [SMILES: N[C@H](Cc1cc2ccccc2[nH]1)C(=O)NOCc1ccc(CNC(=O)CN(CCN(CC(=O)O)CC(=O)O)CCN(CC(=O)O)CC(=O)O)cc1 ; O=C(O)C(F)(F)F]

Prepared as described in Part 20F (47.7 mg, 45.2 μmol; 26.1%). $^1$H NMR (DMSO-$d_6$, 600 MHz): δ 11.63 (1H, s), 11.02 (1H, s), 8.95 (1H, t, J=5.6 Hz), 8.28 (2H, brs), 7.60 (1H, d, J=7.9 Hz), 7.38 (1H, d, J=8.1 Hz), 7.25 (4H, ABq, $J_{AB}$=8.1 Hz), 7.12 (1H, s), 7.10 (1H, t, J=7.4 Hz), 6.91 (1H, t, J=7.5 Hz), 4.60 (2H, ABq, $J_{AB}$=10.9 Hz), 4.36 (2H, d, J=4.7 Hz), 4.26 (2H, s), 3.78-3.72 (1H, m), 3.51 (8H, s), 3.38 (4H, t, J=5.3 Hz), 3.18 (1H, dd, J=14.4, 7.2 Hz), 3.10 (1H, dd, J=14.4, 7.4 Hz), 3.01 (4H, t, J=5.4 Hz). HRMS calcd for $C_{33}H_{43}N_7O_{11}$ (M+H): 714.3093. Found: 714.3089.

EXAMPLE 26

2-(4-{[N-({4-[((2R)-2-amino-3-indol-2-ylpropanoy-laminooxy)methyl]phenyl}methyl)carbamoyl]methyl}-1,4,7,10-tetraaza-7,10-bis(carboxymethyl)cyclododecyl)acetic acid, trifluoroacetic acid salt

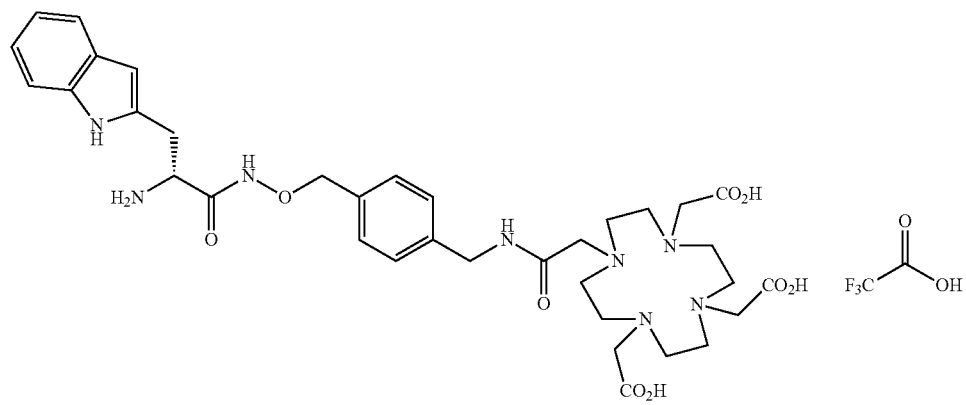 [SMILES: N[C@H](Cc1cc2ccccc2[nH]1)C(=O)NOCc1ccc(CNC(=O)CN2CCN(CC(=O)O)CCN(CC(=O)O)CCN(CC(=O)O)CC2)cc1 ; O=C(O)C(F)(F)F]

part A—Preparation of tert-Butyl 2-{10-[(N-{[4-({(2R)-2-[(tert-butoxy)carbonylamino]-3-indol-2-ylpropanoylaminooxy}methyl)phenyl]methyl}carbamoyl)methyl]-1,4,7,10-tetraaza-4,7-bis{[(tert-butyl)oxycarbonyl]methyl}cyclododecyl}acetate

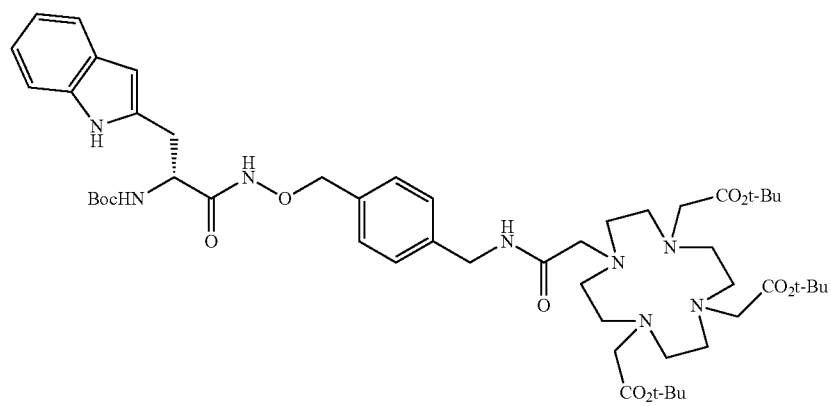 [SMILES: CC(C)(C)OC(=O)CN1CCN(CC(=O)NCc2ccc(CONC(=O)[C@@H](Cc3cc4ccccc4[nH]3)NC(=O)OC(C)(C)C)cc2)CCN(CC(=O)OC(C)(C)C)CCN(CC(=O)OC(C)(C)C)CC1]

Prepared as described in Part 23A. LRMS: 994.0 (100, M+H), 589.7 (50), 447.6 (100).

part B—Preparation of (2-(4-{[N-({4-[((2R)-2-amino-3-indol-2-ylpropanoylaminooxy)methyl]phenyl}methyl)carbamoyl]methyl}-1,4,7,10-tetraaza-7,10-bis(carboxymethyl)cyclododecyl)acetic acid, trifluoroacetic acid salt

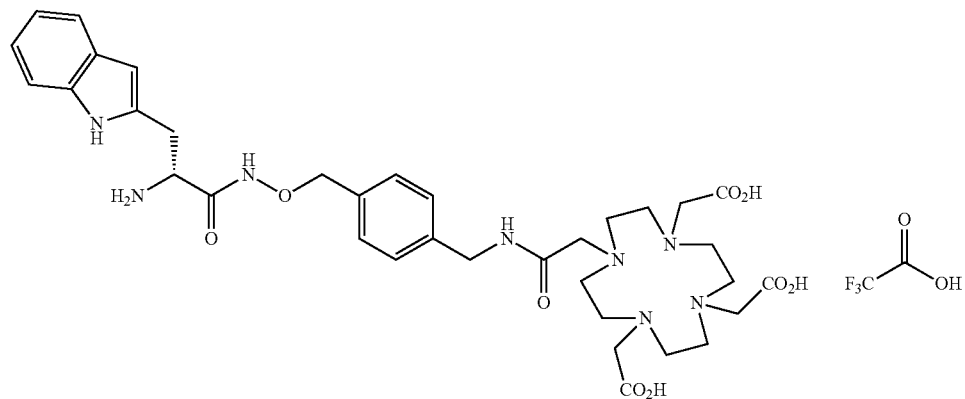 [SMILES: N[C@H](Cc1cc2ccccc2[nH]1)C(=O)NOCc1ccc(CNC(=O)CN2CCN(CC(=O)O)CCN(CC(=O)O)CCN(CC(=O)O)CC2)cc1 ; O=C(O)C(F)(F)F]

Prepared as described in Part 23B (13 mg, 11 μmol; 8.4%). $^1$H NMR (DMSO-$d_6$, 600 MHz): δ 11.63 (1H, s), 11.03 (1H, s), 8.95 (1H, brs), 8.31 (2H, brs), 7.60 (1H, d, J=7.9 Hz), 7.38 (1H, d, J=8.1 Hz), 7.25 (4H, ABq, $J_{AB}$=7.9 Hz), 7.20 (1H, s), 7.10 (1H, t, J=7.5 Hz), 7.02 (1H, t, J=7.5 Hz), 4.60 (2H, ABq, $J_{AB}$=10.9 Hz), 4.36 (2H, d, J=4.5 Hz), 3.75 (1H, t, J=6.4 Hz), 3.63 (4H, s), 3.35 (12H, brs), 3.17 (1H, dd, J=14.4, 7.2 Hz), 3.10 (1H, dd, J=14.5, 7.5 Hz), 3.04 (8H, brs). HRMS calcd for $C_{35}H_{48}N_8O_9$ (M+H): 725.3617. Found: 725.3627.

Example 27

2-({2-[({N-[(4-{[((2R)-2-amino-3-(4-hydroxyphenyl)propanoylaminooxy]methyl}phenyl)methyl]carbamoyl}methyl) {2-[bis(carboxymethyl)amino]ethyl}amino]ethyl}(carboxymethyl)amino)acetic acid, trifluoroacetic acid salt part A—Preparation of (2R)-2-[(tert-Butoxy)carbonylamino]-3-(4-hydroxyphenyl)-N-({4-[(prop-2-enyloxycarbonylamino)methyl]phenyl}methoxy)propanamide

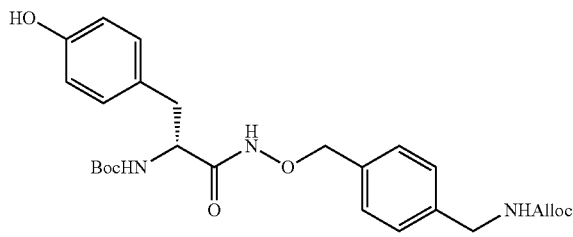

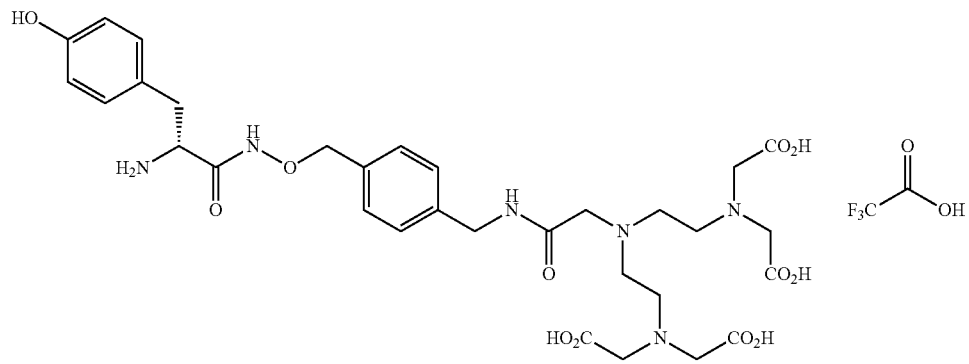 [SMILES: N[C@H](Cc1ccc(O)cc1)C(=O)NOCc1ccc(CNC(=O)CN(CCN(CC(=O)O)CC(=O)O)CCN(CC(=O)O)CC(=O)O)cc1 ; O=C(O)C(F)(F)F]

Prepared as described in Part 20C, using Boc-DTyr-OH (33 mg, 66 μmol; 7.8%). $^1$H NMR (DMSO-$d_6$, 600 MHz): δ 11.14 (1H, s), 9.14 (1H, s), 7.76 (1H, t, J=6.0 Hz), 7.27 (4H, ABq, $J_{AB}$=7.9 Hz), 7.00 (2H, d, J=8.2 Hz), 6.93 (1H, d, J=8.5 Hz), 6.64 (2H, d, J=8.3 Hz), 5.91 (1H, ddt, J=17.5, 10.4, 5.1 Hz), 5.28 (1H, dd, J=17.2, 1.3 Hz), 5.17 (1H, dd, J=10.7, 1.0 Hz), 4.64 (2H, ABq, $J_{AB}$=10.9 Hz), 4.49 (2H, dt, J=5.5, 1.3 Hz), 4.19 (2H, d, J=6.2), 3.91 (1H, AB, $J_{AB}$=8.4 Hz), 2.62-2.76 (2H, m), 1.33 (9H, s). HRMS calcd for $C_{26}H_{33}N_3O_7$ (M+H): 522.2211. Found: 522.2203.

part B—Preparation of (2R)-N-{[4-(aminomethyl) phenyl]methoxy}-2-[(tert-butoxy)carbonylamino]-3-(4-hydroxyphenyl)propanamide, formic acid salt

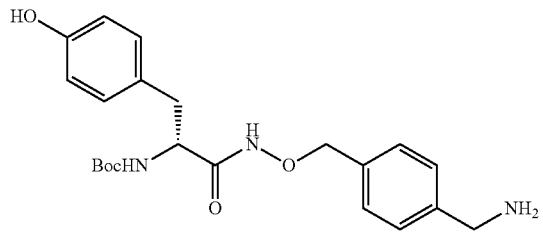

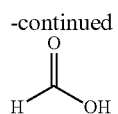

Prepared as described in Part 20D (16.9 mg, 36.6 μmol; 59.0%). $^1$H NMR (DMSO-$d_6$, 600 MHz): δ 8.36 (1H, brs), 7.52 (1H, dt, J=7.6, 2.8 Hz), 7.40 (4H, ABq, $J_{AB}$=7.7 Hz), 7.00 (2H, d, J=8.1 Hz), 6.93 (1H, d, J=8.3 Hz), 6.64 (2H, d, J=7.9 Hz), 4.68 (2H, ABq, $J_{AB}$=10.9 Hz), 3.97 (2H, s), 3.91 (1H, AB, $J_{AB}$=8.0 Hz), 2.73 (1H, dd, J=13.7, 5.9 Hz), 2.66 (1H, dd, J=13.3, 9.2 Hz), 1.33 (9H, s). HRMS calcd for $C_{22}H_{29}N_3O_5$ (M+H): 416.2180. Found: 416.2183.

part C—Preparation of tert-Butyl 2-[(2-{[(N-{[4-({(2R)-2-[(tert-butoxy)carbonylamino]-3-(4-hydroxyphenyl)propanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

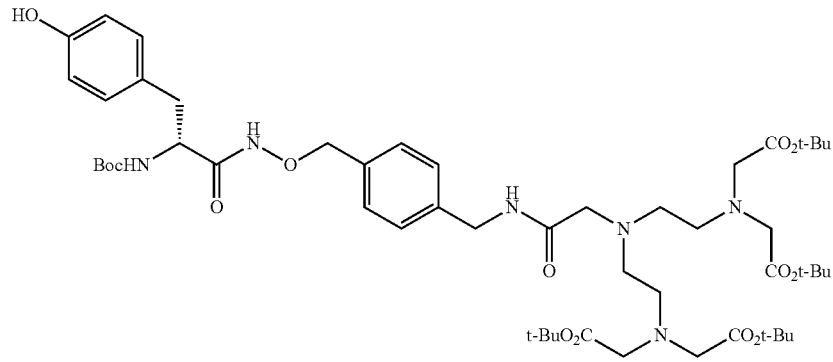

Prepared as described in Part 20E. LRMS: 1016.0 (45, M+H), 458.6 (30, (M-Boc)+2H).

part D—Preparation of 2-({2-[({N-[(4-{[(2R)-2-amino-3-(4-hydroxyphenyl)propanoylaminooxy] methyl}phenyl)methyl]carbamoyl}methyl) {2-[bis (carboxymethyl)amino]ethyl}amino]ethyl} (carboxymethyl)amino)acetic acid, trifluoroacetic acid salt

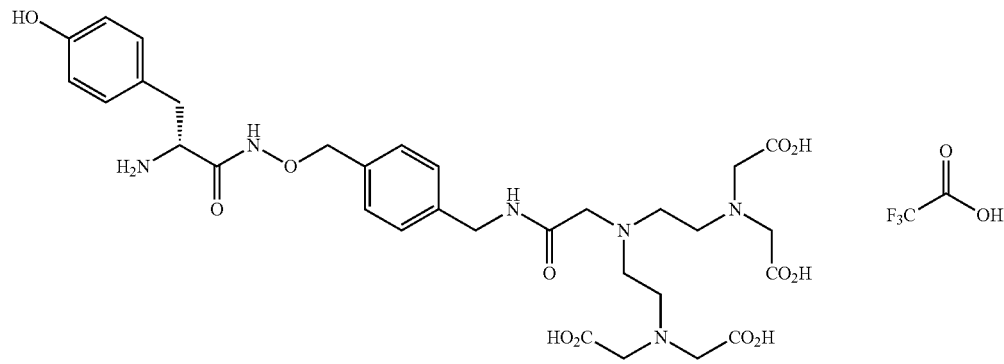 [SMILES: N[C@H](Cc1ccc(O)cc1)C(=O)NOCc1ccc(CNC(=O)CN(CCN(CC(=O)O)CC(=O)O)CCN(CC(=O)O)CC(=O)O)cc1 ; O=C(O)C(F)(F)F]

Prepared as described in Part 20F. $^1$H NMR (DMSO-$d_6$, 600 MHz): δ 11.54 (1H, s), 9.37 (1H, brs), 8.95 (1H, t, J=5.3 Hz), 8.32, (1H, brs), 8.28 (1H, brs), 7.30 (4H, ABq, $J_{AB}$=8.2 Hz), 7.00 (2H, d, J=8.2 Hz), 6.72 (2H, d, J=8.6 Hz), 4.64 (2H, ABq, $J_{AB}$=10.9 Hz), 4.36 (2H, d, J=5.9 Hz), 4.26 (2H, s), 3.66 (2H, brs), 3.66-3.39 (9H, m), 3.41-3.36 (4H, m), 3.06 (4H, t, J=5.6 Hz), 2.88 (2H, d, J=7.6 Hz). HRMS calcd for $C_{31}H_{42}N_6O_{12}$ (M+H): 691.2936. Found: 691.2944.

EXAMPLE 28

2-{[2-({[N-({4-[((2R)-2-amino-3-(3-pyridyl)propanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt part A—Preparation of (2R)-2-[(tert-butoxy)carbonylamino]-N-({4-[(prop-2-enyloxycarbonylamino)methyl]phenyl}methoxy)-3-(3-pyridyl)propanamide

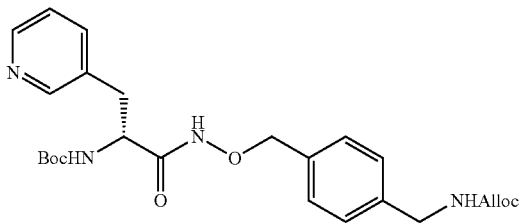

Prepared as described in Part 20C, using Boc-DPya-OH. LRMS: 485.6 (100, M+H).

part B—Preparation of (2R)-N-{[4-(aminomethyl)phenyl]methoxy}-2-[(tert-butoxy)carbonylamino]-3-(3-pyridyl)propanamide, formic acid salt

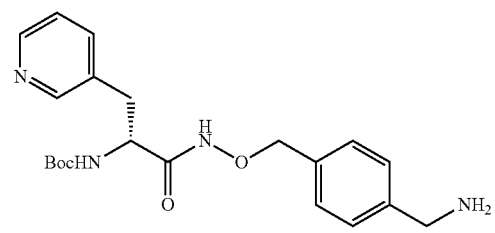

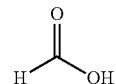

Prepared as described in Part 20D (151 mg, 0.338 mmol; 79.9%). LRMS: 401.6 (100, M+H).

part C—Preparation of tert-Butyl 2-[(2-{[(N-{[4-({(2R)-2-[(tert-butoxy)carbonylamino]-3-(3-pyridyl)propanoylaminooxy}methyl)phenyl]methyl}carbamoyl)methyl][2-(bis{[(tert-butyl)oxycarbonyl]methyl}amino)ethyl]amino}ethyl){[(tert-butyl)oxycarbonyl]methyl}amino]acetate

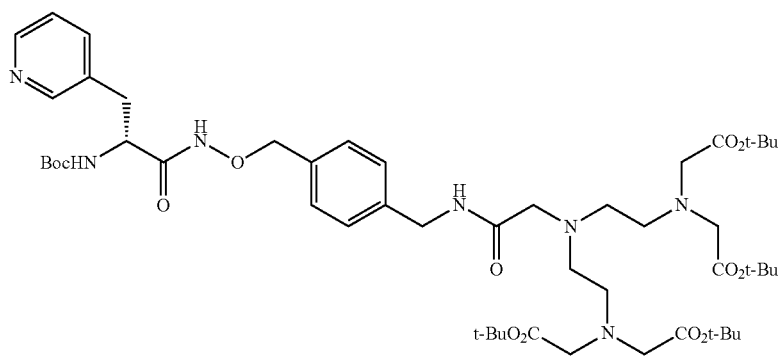

Prepared as described in Part 20E. LRMS: 1001.0 (75, M+H), 501.2 (100, M+2H).

part D—Preparation of 2-{[2-({[N-({4-[((2R)-2-amino-3-(3-pyridyl)propanoylaminooxy)methyl]phenyl}methyl)carbamoyl]methyl}{2-[bis(carboxymethyl)amino]ethyl}amino)ethyl](carboxymethyl)amino}acetic acid, trifluoroacetic acid salt

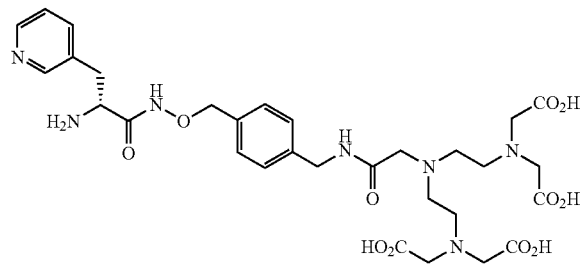

-continued

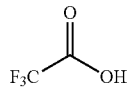

Prepared as described in Part 20F (3.3 mg, 3.2 μmol; 1.8%). $^1$H NMR (DMSO-$d_6$, 600 MHz): δ 11.64 (1H, s), 8.95 (1H, t, J=5.8 Hz), 8.52 (1H, d, J=5.0 Hz), 8.38 (2H, brs), 7.81-7.76 (1H, m), 7.38-7.26 (6H, m), 4.69 (2H, ABq, $J_{AB}$=11.6 Hz), 4.37 (2H, d, J=4.7 Hz), 4.27 (2H, s), 4.07 (1H, t, J=5.9 Hz), 3.64 (8H, brs), 3.39 (4H, t, J=5.7 Hz), 3.19 (2H, d, J=7.1 Hz), 3.06 (4H, t, J=5.9 Hz). HRMS calcd for $C_{30}H_{41}N_7O_{11}$ (M+H): 676.2937. Found: 676.2940.

EXAMPLES 29-36

Synthesis of Gadolinium Complexes

The following procedure is representative of the fashion in which gadolinium complexes of the aforementioned examples are prepared. Yield and characterization data are provided in Table 1.

A solution of the product of Example 2 (24.3 mg, 23.3 μmol) in Milli-Q $H_2O$ (466 μL) was treated with $GdCl_3$ (7.4 mg, 28 μmol) in one portion at 22° C. The pH of the solution was adjusted to 5-6 with aqueous NaOH (933 μL of a 0.1 M solution); direct HPLC analysis of the reaction mixture using a pH 7 mobile phase indicated complexation was complete. The solution was diluted with 15 mM $NH_4OAc$ (5 mL) and directly purified by HPLC on a Phenomenex Luna C18 column (21.2×250 mm) using a 1.0%/min gradient of 0-30% MeCN at a flow rate of 20 mL/min; 5 mM $NH_4OAc$ was employed as the aqueous component. The main product peak eluting at 19 min was collected and lyophilized to give the title compound as a microcrystalline solid (15.5 mg, 18.2 μmol; 77.8%).

TABLE 1

Characterization data for Examples 29-36

| example | precursor (as shown in Example #) | yield (%) | LRMS (ESI) | HRMS (calcd. for; found) |
| --- | --- | --- | --- | --- |
| 29 | 1 | 51 | 1687.1 (21, 2M + H), 1265.3 (20, 3M + 2H), 843.8 (100, M + H) | $C_{32}H_{41}GdN_6O_{11}$ (M + H) 844.2147; 844.2140 |
| 30 | 2 | 78 | 855.6 (100, M + H), 428.5 (24, M + 2H) | $C_{34}H_{46}GdN_7O_9$ (M + H) 855.2671; 855.2681 |
| 31 | 23 | 64 | 1614.1 (12, 2M + H), 807.6 (100, M + H), 403.5 (45, M + 2H) | $C_{30}H_{46}GdN_7O_9$ (M + H) 807.2671; 807.2678 |
| 32 | 21 | 43 | 1320 (27, 3M + 2H), 880.3 (100, M + H), 441.7 (72, M + 2H) | $C_{35}H_{41}GdN_6O_{11}$ (M + H) 880.2147; 880.2155 |
| 33 | 24 | 16 | 891.6 (79, M + H), 736.8 (100), 369.0 (54) | $C_{37}H_{46}GdN_7O_9$ (M + H) 891.2671; 891.2677 |
| 34 | 20 | 69 | 1591.9 (15, 2M + H), 796.5 (100, M + H), 398.9 (55, M + 2H) | $C_{28}H_{41}GdN_6O_{11}$ (M + H) 796.2147; 796.2148 |
| 35 | 25 | 55 | 880.7 (21, M + Na), 869.1 (100, M + H), 435.8 (25, M + 2H) | $C_{33}H_{40}GdN_7O_{11}$ (M + H) 869.2100; 869.2099 |
| 36 | 26 | 15 | 1759.2 (10, 2M + H), 880.7 (100, M + H), 440.0 (35, M + 2H) | $C_{35}H_{45}GdN_8O_9$ (M + H) 880.2623; 880.2625 |

EXAMPLES 37-64

Synthesis of [$^{153}$Gd]Gadolinium Complexes

The following procedure is representative of the fashion in which gadolinium complexes of the aforementioned examples are prepared. Radiochemical purity values for each complex are provided in Table 2.

Using a lead-shielded vial, a solution of the product of Example 2 (0.350 mg, 0.336 μmol) in 0.5 M $NH_4OAc$ (0.850 mL) was treated with [$^{153}$Gd]$GdCl_3$ (75 μL of a 12.5 mCi/μL solution in 0.5 N HCl) in one portion at 22° C. The vial was capped using a rubber stopper, secured with an aluminum crimp ring, then heated to 95° C. ($H_2O$ bath) and maintained 20 min. After cooling to 22° C., a 25 μL aliquot was removed and analyzed by HPLC to confirm complete conversion. The crude reaction mixture was then purified by HPLC on a Phenomenex Cosmosil C18 column (4.6×250 mm) using a 6.7%/min gradient from 0-100% MeCN at 1 mL/min with detection using inline INUS β-Ram and PDA (220 nm) modules; 25 mM NH$_4$OAc was employed as the aqueous component. Product-containing fractions were collected, concentrated under reduced pressure and analyzed using the aforementioned method to determine radiochemical purity.

TABLE 2

Characterization data for Examples 37-64

| precursor (as shown in Example #) | Example # | % RCP |
|---|---|---|
| 1 | 37 | 100 |
| 2 | 38 | 100 |
| 3 | 39 | 100 |
| 4 | 40 | 100 |
| 5 | 41 | 95.0 |
| 6 | 42 | 98.7 |
| 7 | 43 | 99.1 |
| 8 | 44 | 96.6 |
| 9 | 45 | 99.3 |
| 10 | 46 | 74.5 |
| 11 | 47 | 96.3 |
| 12 | 48 | 68.2 |
| 13 | 49 | 100 |
| 14 | 50 | 100 |
| 15 | 51 | 100 |
| 16 | 52 | 95.4 |
| 17 | 53 | 80.0 |
| 18 | 54 | 100 |
| 19 | 55 | 100 |
| 20 | 56 | 100 |
| 21 | 57 | 96.9 |
| 22 | 58 | 98.8 |
| 23 | 59 | 94.5 |
| 24 | 60 | 100 |
| 25 | 61 | 100 |
| 26 | 62 | 100 |
| 27 | 63 | 100 |
| 28 | 64 | 100 |

EXAMPLE 65

Ex-Vivo Blood Vessel Binding Assay

Aorta bearing atherosclerotic plaque was obtained from New Zealand white rabbits that were balloon stripped along the abdominal aorta and placed on a high fat diet (0.5% cholesterol) for 16-22 weeks. Vascular injury was produced with a 4-F Fogarty catheter along the abdominal aorta and right iliofemoral artery. This procedure generates an accelerated complex lesion development with a lipid rich core covered by a fibrous cap in rabbits. Harvested aorta sections (0.5 cm) were incubated with 0.135 µCi of $^{153}$Gd-labeled compound diluted in phosphate buffered saline (450 µL) for 2 h at 37° C. The supernatant was removed and analyzed by HPLC to assay compound stability. The tissue section was then washed with phosphate buffered saline (3×10 mL), then resuspended (10 mL) and incubated at 37° C. an additional 1 h. The supernatant was then removed, the washing process repeated and the tissue finally counted on a gamma counter. The amount of compound bound to the tissue was determined as a percentage of the initial activity according to the following formula:

$$\% \text{ Tissue Uptake} = \frac{\text{Counts bound to tissue}}{\text{Total counts in test tube}} \times 100$$

The data for percentage compound bound to plaque-bearing aorta is collected in Table 3.

TABLE 3

Ex-vivo blood vessel binding data

| example # | % bound |
|---|---|
| 37 | 12.8 |
| 38 | 19.1 |
| 39 | 15.8 |
| 40 | 7.2 |
| 41 | 28.7 |
| 42 | 17.9 |
| 43 | 27.1 |
| 44 | 27.3 |
| 45 | 14.4 |
| 46 | 0.9 |
| 47 | 6.6 |
| 49 | 9.1 |
| 50 | 24.2 |
| 52 | 6.9 |
| 57 | 30.6 |
| 58 | 7.3 |
| 59 | 5.2 |
| 60 | 30.9 |
| 61 | 19.9 |
| 62 | 17.1 |
| 63 | 11.7 |

EXAMPLE 66

In-Vivo ApoE Mouse Aorta Uptake Studies

The apolipoprotein E (ApoE) knockout mouse is a model of hypercholesterolemia that develops atherosclerotic lesions in the brachiocephalic artery, the aortic arch and the abdominal aorta. Mice were fed a high-fat diet to accelerate plaque formation and compounds were tested in the mice between 35-42 weeks on diet. Test compounds were administered at 0.3-0.4 mCi/kg to anesthetized mice in a single, bolus injection via the tail vein. Blood samples were collected via the tail between 0-30 min post injection for pharmacokinetic analysis and mice were euthanized by CO$_2$ at 60 min for tissue harvesting. The aorta was first flushed with saline through the left ventricle exiting via the femoral vein then removed from the heart to the renal bifurcation; additional biological samples were also collected (blood, muscle, liver, kidney, bile, urine, heart, femur, reproductive organ, lung, spleen and innominate artery). All samples were weighed and assayed for radioactivity; uptake is expressed as a percentage of injected dose per gram of tissue (% ID/g). Aorta uptake, aorta to blood ratios and aorta to heart ratios are summarized in Table 4.

TABLE 4

ApoE mouse aorta uptake, aorta:heart and aorta:blood ratios

| example # | aorta uptake (% ID/g) | aorta:heart | aorta:blood |
|---|---|---|---|
| 37 | 10.4 ± 1.4 | 16.2 | 4.2 |
| 38 | 11.6 ± 0.8 | 20.5 | 5.5 |
| 39 | 6.1 ± 0.4 | 13.6 | 11.4 |
| 40 | 3.6 ± 0.3 | 8.4 | 3.4 |
| 41 | 2.0 ± 0.1 | 20.4 | 7.2 |
| 42 | 8.1 ± 1.1 | 18.0 | 8.0 |
| 43 | 6.0 ± 1.7 | 9.0 | 2.7 |
| 44 | 8.4 ± 0.2 | 12.5 | 3.2 |
| 45 | 9.0 ± 0.2 | 12.1 | 2.1 |
| 46 | 0.9 ± 0.2 | 4.9 | 1.1 |
| 47 | 4.7 ± 0.4 | 4.8 | 0.7 |
| 49 | 4.9 ± 0.2 | 22.9 | 5.5 |
| 50 | 10.4 ± 2.4 | 13.5 | 3.7 |
| 52 | 6.1 ± 1.2 | 9.2 | 2.0 |
| 53 | 1.5 ± 0.1 | 4.2 | 0.8 |

TABLE 4-continued

ApoE mouse aorta uptake, aorta:heart and aorta:blood ratios

| example # | aorta uptake (% ID/g) | aorta:heart | aorta:blood |
|---|---|---|---|
| 54 | 2.5 ± 0.5 | 5.3 | 1.2 |
| 55 | 3.0 ± 2.3 | 8.8 | 1.0 |
| 56 | 8.5 ± 1.8 | 21.2 | 5.5 |
| 57 | 11.1 ± 0.3 | 17.8 | 5.0 |
| 58 | 6.1 ± 0.2 | 17.9 | 6.5 |
| 59 | 8.2 ± 1.3 | 15.4 | 3.7 |
| 60 | 18.4 ± 2.4 | 25.2 | 9.8 |
| 61 | 19.3 ± 0.2 | 20.4 | 10.9 |
| 62 | 11.8 ± 1.4 | 22.2 | 5.7 |
| 63 | 8.7 ± 0.4 | 13.0 | 6.0 |

EXAMPLE 67

In-Vivo Rabbit Aorta Uptake Studies

Atherosclerosis was induced in New Zealand White male rabbits (3 kg) with aortic balloon endothelial injury (vide supra) followed by feeding a 0.5% cholesterol diet for 22 weeks. Test compounds were administered at 0.01-0.05 mCi/kg to anesthetized rabbits in a single, bolus injection via the marginal ear vein. Blood samples were collected from the central ear artery at 0, 2, 5, 7, 10, 15, 30 and 60 min post injection. Rabbits were euthanized at 60 min post injection for tissue harvesting (blood, muscle, bile, urine, kidney, liver, spleen, heart, lung, colon, small intestine, stomach, testes and in some cases, sternum, ligament and right ear). Abdominal aorta (upper, middle, and lower) and left and right femoral arteries were also collected. All samples were weighed and assayed for radioactivity; uptake is expressed as percentage of injected dose per gram of tissue (% ID/g). Aorta uptake, aorta to blood ratios and aorta to heart ratios are summarized in Table 5; a comparative analysis between plaque bearing and non-plaque bearing rabbits is also provided.

TABLE 5

Rabbit aorta uptake, aorta:heart and aorta:blood ratios

| | plaque rabbit | | | control rabbit | | |
|---|---|---|---|---|---|---|
| example # | aorta (% ID/g ± SD) | aorta:heart | aorta:blood | aorta (% ID/g ± SD) | aorta:heart | aorta:blood |
| 37 | 0.087 ± 0.010 | 4.6 | 2.1 | — | — | — |
| 38 | 0.103 ± 0.002 | 5.1 | 2.4 | 0.196 ± 0.023 | 11.0 | 5.1 |
| 60 | 0.108 ± 0.012 | 4.0 | 2.4 | 0.187 ± 0.022 | 6.4 | 3.8 |
| 62 | — | — | — | 0.159 | 6.4 | 3.2 |

EXAMPLE 68

In Vivo Rabbit Aorta MR Imaging

Atherosclerosis was induced in New Zealand White male rabbits (3 kg) with aortic balloon endothelial injury (vide supra) followed by feeding a 0.5% cholesterol diet for 22 weeks. A series of pre-injection images were acquired. The rabbit was then injected with test compound (i.e., Example 31) at 0.1 mmol/kg via the marginal ear vein and images acquired at specified time intervals. All images were acquired at 4.7 T using an 8.5 cm field of view, 256×256 matrix using a black blood, flow-suppressed spin-echo method. A marked increase of relative image intensity in the aorta (ring-shaped structure) was observed shortly after injection; sample images are provided in FIG. 1.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A method of detecting, imaging, and/or monitoring a patient comprising the steps of:
   administering to the patient a chelated imaging agent; and
   acquiring an image of the site of concentration of the chelated imaging agent in the patient by a diagnostic imaging technique;
   wherein the chelated imaging agent comprises:
   an imaging agent selected from the group consisting of a non-metallic isotope, an optical reporter, a paramagnetic metal ion, a ferromagnetic metal, a gamma-emitting radioisotope, a positron-emitting radioisotope and an x-ray absorber; and
   a compound of Formula (I):

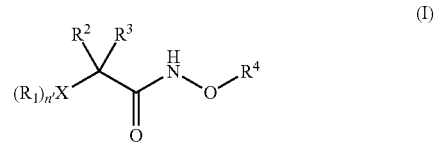

or a pharmaceutically acceptable salt thereof, wherein:
   X is N, O, S, or P;
   $R^1$ is hydrogen, alkyl, alkenyl, arylalkyl, alkylarylalkyl, alkoxyalkyl, heteroalkyl, or heterocyclylalkyl, provided that when X is N, at least one $R^1$ is H;
   $R^2$ and $R^3$ can be the same or different and are hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and
   $R^4$ is alkyl, alkenyl, cycloalkyl, alkylaryl, alkylcarbonyl, aryl, arylalkyl, alkylarylalkyl, alkoxyalkyl, alkoxycarbonyl, heteroalkyl, heterocyclyl, or heterocyclylalkyl;
   wherein each $R^1$, $R^2$, $R^3$, and $R^4$ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —$NR^{19}R^{20}$, —SH, —S(Pg), —OH, —$PR^{19}R^{20}$, —P(O)$R^{21}R^{22}$, —$CO_2H$, =O, halo, trifluoromethyl, cyano, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24}$, —$OR^{24}$, —$OC(=O)N(R^{24})_2$, —$NR^{24}C(=O)R^{24}$, —$NR^{24}C(=O)OR^{24}$, —$NR^{24}C(=O)N(R^{24})_2$, —$NR^{24}SO_2N(R^{24})_2$, —$NR^{24}SO_2R^{24}$, —$SO_3H$, —$SO_2R^{24}$, —$SR^{24}$, —$S(=O)R^{24}$, —$SO_2N(R^{24})_2$, —$N(R^{24})_2$, —$NHC(=S)NHR^{24}$, =$NOR^{24}$, $NO_2$, —$C(=O)NHOR^{24}$, —$C(=O)NHN(R^{24})_2$, —$OCH_2CO_2H$, 2-(1-morpholino)ethoxy, or a chelator moiety;

$R^{19}$ and $R^{20}$ are each independently selected from hydrogen, $C_{1-10}$alkyl substituted with 0-3 $R^{23}$, aryl substituted with 0-3 $R^{23}$, $C_{1-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;

$R^{21}$ and $R^{22}$ are each independently selected from —OH, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;

each $R^{23}$ is independently selected from =O, halo, trifluoromethyl, cyano, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24}$, —$OR^{24}$, —$OC(=O)N(R^{24})_2$, —$NR^{24}C(=O)R^{24}$, —$NR^{24}C(=O)OR^{24}$, —$NR^{24}C(=O)N(R^{24})_2$, —$NR^{24}SO_2N(R^{24})_2$, —$NR^{24}SO_2R^{24}$, —$SO_3H$, —$SO_2R^{24}$, —$SR^{24}$, —$S(=O)R^{24}$, —$SO_2N(R^{24})_2$, —$N(R^{24})_2$, —$NHC(=S)NHR^{24}$, =$NOR^{24}$, —$NO_2$, —$C(=O)NHOR^{24}$, —$C(=O)NHN(R^{24})_2$, —$OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0-2 $R^{24}$, and heterocyclyl;

each $R^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl;

Pg is a thiol protecting group; and n' is an integer from 1-3, wherein the compound of Formula (I) comprises at least one chelator moiety, wherein at least one of $R^1$, $R^2$, $R^3$, or $R^4$ is substituted with the at least one chelator moiety, and wherein the imaging agent is bound to the at least one chelator moiety.

2. The method of claim 1 comprising detecting, imaging, and/or monitoring elastin-rich tissues in the patient.

3. The method of claim 1 comprising detecting, imaging, and/or monitoring the presence of coronary plaque, carotid plaque, iliac/femoral plaque, aortic plaque, renal artery plaque, plaque of any arterial vessel, aneurism, vasculitis, other diseases of the arterial wall, and/or damage or structural changes in ligaments, uterus, lungs or skin in the patient.

4. The method of claim 1, wherein the imaging agent is a paramagnetic metal ion.

5. The method of claim 4, wherein the paramagnetic metal ion is Gd(III).

6. The method of claim 1, wherein the imaging agent is a gamma-emitting radioisotope or positron-emitting radioisotope selected from the group consisting of $^{111}$In, $^{62}$Cu, $^{64}$Cu, $^{67}$Ga, $^{68}$Ga, and $^{153}$Gd.

7. The method of claim 1, wherein the imagining agent is a non-metallic isotope selected from the group consisting of $^{11}$C, $^{14}$C, $^{13}$N, $^{18}$F, $^{123}$I, $^{124}$I, and $^{125}$I.

8. The method of claim 1, wherein at least one $R^1$ is hydrogen.

9. The method of claim 1, wherein X is nitrogen.

10. The method of claim 1, wherein:

X is nitrogen;

$R^1$ is hydrogen, alkyl, arylalkyl, or alkylarylalkyl;

$R^2$ and $R^3$ can be the same or different and are hydrogen, alkyl, alkylaryl, aryl, arylalkyl, alkylarylalkyl, or heterocyclylalkyl;

$R^4$ is alkyl, alkylaryl, aryl, arylalkyl, or alkylarylalkyl, wherein each $R^1$, $R^2$, $R^3$, and $R^4$ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —$NR^{19}R^{20}$, —SH, —S(Pg), —OH, —$PR^{19}R^{20}$, —$P(O)R^{21}R^{22}$, —$CO_2H$, =O, halo, trifluoromethyl, cyano, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24}$, —$OR^{24}$, —$OC(=O)N(R^{24})_2$, —$NR^{24}C(=O)R^{24}$, —$NR^{24}C(=O)OR^{24}$, —$NR^{24}C(=O)N(R^{24})_2$, —$NR^{24}SO_2N(R^{24})_2$, —$NR^{24}SO_2R^{24}$, —$SO_3H$, —$SO_2R^{24}$, —$SR^{24}$, —$S(=O)R^{24}$, —$SO_2N(R^{24})_2$, —$N(R^{24})_2$, —$NHC(=S)NHR^{24}$, =$NOR^{24}$, $NO_2$, —$C(=O)NHOR^{24}$, —$C(=O)NHN(R^{24})_2$, —$OCH_2CO_2H$, 2-(1-morpholino)ethoxy, or a chelator moiety;

$R^{19}$ and $R^{20}$ are each independently selected from hydrogen, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;

$R^{21}$ and $R^{22}$ are each independently selected from —OH, $C_{1-10}$alkyl substituted with 0-3 $R^{23}$, aryl substituted with 0-3 $R^{23}$, $C_{3-10}$cycloalkyl substituted with 0-3 $R^{23}$, heterocyclyl-$C_{1-10}$alkyl substituted with 0-3 $R^{23}$, $C_{6-10}$aryl-$C_{1-10}$alkyl substituted with 0-3 $R^{23}$, and heterocyclyl substituted with 0-3 $R^{23}$;

each $R^{23}$ is independently selected from =O, halo, trifluoromethyl, cyano, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24}$, —$OR^{24}$, —$OC(=O)N(R^{24})_2$, —$NR^{24}C(=O)R^{24}$, —$NR^{24}C(=O)OR^{24}$, —$NR^{24}C(=O)N(R^{24})_2$, —$NR^{24}SO_2N(R^{24})_2$, —$NR^{24}SO_2R^{24}$, —$SO_3H$, —$SO_2R^{24}$, —$SR^{24}$, —$S(=O)R^{24}$, —$SO_2N(R^{24})_2$, —$N(R^{24})_2$, —$NHC(=S)NHR^{24}$, =$NOR^{24}$, —$NO_2$, —$C(=O)NHOR^{24}$, —$C(=O)NHN(R^{24})_2$, —$OCH_2CO_2H$, 2-(1-morpholino)ethoxy, $C_{1-5}$alkyl, $C_{2-4}$alkenyl, $C_{3-6}$cycloalkyl, $C_{3-6}$cycloalkylmethyl, $C_{2-6}$alkoxyalkyl, aryl substituted with 0-2 $R^{24}$, and heterocyclyl;

each $R^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl;

Pg is a thiol protecting group; and wherein at least one of $R^1$, $R^2$, $R^3$, and $R^4$ is substituted with a chelator moiety.

11. The method of claim 1, wherein:
R² or R³ comprises the following structure,

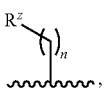

wherein:
n is 0-6; and
R$^z$ is alkyl, aryl, cycloalkyl, or heterocyclyl.

12. The method of claim 1, wherein:

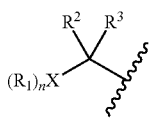

comprises the following structure:

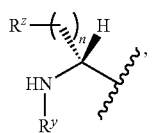

wherein:
n is 0-6;
R$^y$ is hydrogen, alkenyl, or alkyl; and
R$^z$ is alkyl, aryl, cycloalkyl, or heterocyclyl.

13. The method of claim 1, wherein R¹ is substituted with the at least one chelator moiety.

14. The method of claim 1, wherein R² or R³ is substituted with the at least one chelator moiety.

15. The method of claim 1, wherein R⁴ is substituted with the at least one chelator moiety.

16. The method of claim 1, wherein the compound of Formula (I) has a structure as in Formula (II):

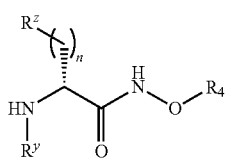

(II)

or a pharmaceutically acceptable salt thereof,
wherein:
R⁴ is alkyl, alkenyl, cycloalkyl, alkylaryl, alkylcarbonyl, aryl, arylalkyl, alkylarylalkyl, alkoxyalkyl, alkoxycarbonyl, heteroalkyl, heterocyclyl, or heterocyclylalkyl, substituted with the at least one chelator moiety;
n is 0-6;
R$^y$ is hydrogen, alkenyl, or alkyl; and
R$^z$ is alkyl, aryl, cycloalkyl, or heterocyclyl,
wherein R⁴ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —NR¹⁹R²⁰, —SH, —S(Pg), —OH, —PR¹⁹R²⁰, —P(O)R²¹R²², —CO₂H, =O, halo, trifluoromethyl, cyano, —CO₂R²⁴, —C(=O)R²⁴, —C(=O)N(R²⁴)₂, —CHO, —CH₂OR²⁴, —OC(=O)R²⁴, —OC(=O)OR²⁴, —OR²⁴, —OC(=O)N(R²⁴)₂, —NR²⁴C(=O)R²⁴, —NR²⁴C(=O)OR²⁴, —NR²⁴C(=O)N(R²⁴)₂, —NR²⁴SO₂N(R²⁴)₂, —NR²⁴SO₂R²⁴, —SO₃H, —SO₂R²⁴, —SR²⁴, —S(=O)R²⁴, —SO₂N(R²⁴)₂, —N(R²⁴)₂, —NHC(=S)NHR²⁴, =NOR²⁴, NO₂, —C(=O)NHOR²⁴, —C(=O)NHN(R²⁴)₂, —OCH₂CO₂H, 2-(1-morpholino)ethoxy, or a chelator moiety;

R¹⁹ and R²⁰ are each independently selected from hydrogen, C$_{1-10}$alkyl substituted with 0-3 R²³, aryl substituted with 0-3 R²³, C$_{3-10}$cycloalkyl substituted with 0-3 R²³, heterocyclyl-C$_{1-10}$alkyl substituted with 0-3 R²³, C$_{6-10}$aryl-C$_{1-10}$alkyl substituted with 0-3 R²³, and heterocyclyl substituted with 0-3 R²³;

R²¹ and R²² are each independently selected from —OH, C$_{1-10}$alkyl substituted with 0-3 R²³, aryl substituted with 0-3 R²³, C$_{3-10}$cycloalkyl substituted with 0-3 R²³, heterocyclyl-C$_{1-10}$alkyl substituted with 0-3 R²³, C$_{6-10}$aryl-C$_{1-10}$alkyl substituted with 0-3 R²³, and heterocyclyl substituted with 0-3 R²³;

each R²³ is independently selected from =O, halo, trifluoromethyl, cyano, —CO₂R²⁴, —C(=O)R²⁴, —C(=O)N(R²⁴)₂, —CHO, —CH₂OR²⁴, —OC(=O)R²⁴, —OC(=O)OR²⁴, —OR²⁴, —OC(=O)N(R²⁴)₂, —NR²⁴C(=O)R²⁴, —NR²⁴C(=O)OR²⁴, —NR²⁴C(=O)N(R²⁴)₂, —NR²⁴SO₂N(R²⁴)₂, —NR²⁴SO₂R²⁴, —SO₃H, —SO₂R²⁴, —SR²⁴, —S(=O)R²⁴, —SO₂N(R²⁴)₂, —N(R²⁴)₂, —NHC(=S)NHR²⁴, =NOR²⁴, —NO₂, —C(=O)NHOR²⁴, —C(=O)NHN(R²⁴)₂, —OCH₂CO₂H, 2-(1-morpholino)ethoxy, C$_{1-5}$alkyl, C$_{2-4}$alkenyl, C$_{3-6}$cycloalkyl, C$_{3-6}$cycloalkylmethyl, C$_{2-6}$alkoxyalkyl, aryl substituted with 0-2 R²⁴, and heterocyclyl;

each R²⁴ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and Pg is a thiol protecting group.

17. The method of claim 1, wherein the compound of Formula (I) has a structure as in Formula (III):

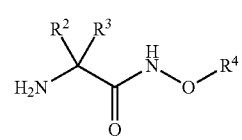

(III)

or a pharmaceutically acceptable salt thereof, wherein:
R² and R³ can be the same or different and are hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl, and at least one of R² and R³ is substituted with the at least one chelator moiety; and
R⁴ is alkyl, alkylaryl, or arylalkyl,
wherein each R², R³, and R⁴ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —NR¹⁹R²⁰, —SH, —S(Pg), —OH, —PR¹⁹R²⁰, —P(O)R²¹R²², —CO₂H, =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, NO$_2$, —C(=O)NHOR$^{24}$, —C(=O)NHN(R$^{24}$)$_2$, —OCH$_2$CO$_2$H, 2-(1-morpholino)ethoxy, or a chelator moiety;

R$^{19}$ and R$^{20}$ are each independently selected from hydrogen, C$_{1-10}$alkyl substituted with 0-3 R$^{23}$, aryl substituted with 0-3 R$^{23}$, C$_{3-10}$cycloalkyl substituted with 0-3 R$^{23}$, heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$;

R$^{21}$ and R$^{22}$ are each independently selected from —OH, C$_{1-10}$alkyl substituted with 0-3 R$^{23}$, aryl substituted with 0-3 R$^{23}$, C$_{3-10}$cycloalkyl substituted with 0-3 R$^{23}$, heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$;

each R$^{23}$ is independently selected from =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, —NO$_2$, —C(=O)NHOR$^{24}$, —C(=O)NHN(R$^{24}$)$_2$, —OCH$_2$CO$_2$H, 2-(1-morpholino)ethoxy, C$_{1-5}$alkyl, C$_{2-4}$alkenyl, C$_{3-6}$cycloalkyl, C$_{3-6}$cycloalkylmethyl, C$_{2-6}$alkoxyalkyl, aryl substituted with 0-2 R$^{24}$, and heterocyclyl;

each R$^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and Pg is a thiol protecting group.

18. The method of claim 1, wherein the compound of Formula (I) has a structure as in Formula (IV):

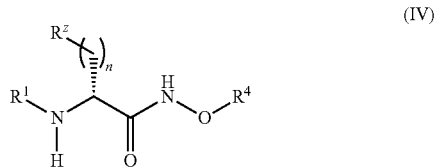

(IV)

or a pharmaceutically acceptable salt thereof, wherein:

R$^1$ is alkyl, alkenyl, cycloalkyl, arylalkyl, alkylarylalkyl, alkoxyalkyl, heteroalkyl, or heterocyclylalkyl, substituted with the at least one chelator moiety;

n is 0-6;

R$^z$ is alkyl, aryl, cycloalkyl, or heterocyclyl; and

R$^4$ is alkyl, alkylaryl, or arylalkyl, wherein each R$^1$ and R$^4$ is unsubstituted or substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, or heterocyclylalkyl, —NR$^{19}$R$^{20}$, —SH, —S(Pg), —OH, —PR$^{19}$R$^{20}$, —P(O)R$^{21}$R$^{22}$, —CO$_2$H, =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, NO$_2$, —C(=O)NHOR$^{24}$, —C(=O)NHN(R$^{24}$)$_2$, —OCH$_2$CO$_2$H, 2-(1-morpholino)ethoxy, or a chelator moiety;

R$^{19}$ and R$^{20}$ are each independently selected from hydrogen, C$_{1-10}$alkyl substituted with 0-3 R$^{23}$, aryl substituted with 0-3 R$^{23}$, C$_{3-10}$cycloalkyl substituted with 0-3 R$^{23}$, heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$;

R$^{21}$ and R$^{22}$ are each independently selected from —OH, C$_{1-10}$alkyl substituted with 0-3 R$^{23}$, aryl substituted with 0-3 R$^{23}$, C$_{3-10}$cycloalkyl substituted with 0-3 R$^{23}$, heterocyclyl-C$_{1-10}$alkyl substituted with 0-3 R$^{23}$, C$_{6-10}$aryl-C$_{1-10}$alkyl substituted with 0-3 R$^{23}$, and heterocyclyl substituted with 0-3 R$^{23}$;

each R$^{23}$ is independently selected from =O, halo, trifluoromethyl, cyano, —CO$_2$R$^{24}$, —C(=O)R$^{24}$, —C(=O)N(R$^{24}$)$_2$, —CHO, —CH$_2$OR$^{24}$, —OC(=O)R$^{24}$, —OC(=O)OR$^{24}$, —OR$^{24}$, —OC(=O)N(R$^{24}$)$_2$, —NR$^{24}$C(=O)R$^{24}$, —NR$^{24}$C(=O)OR$^{24}$, —NR$^{24}$C(=O)N(R$^{24}$)$_2$, —NR$^{24}$SO$_2$N(R$^{24}$)$_2$, —NR$^{24}$SO$_2$R$^{24}$, —SO$_3$H, —SO$_2$R$^{24}$, —SR$^{24}$, —S(=O)R$^{24}$, —SO$_2$N(R$^{24}$)$_2$, —N(R$^{24}$)$_2$, —NHC(=S)NHR$^{24}$, =NOR$^{24}$, —NO$_2$, —C(=O)NHOR$^{24}$, —C(=O)NHN(R$^{24}$)$_2$, —OCH$_2$CO$_2$H, 2-(1-morpholino)ethoxy, C$_{1-5}$alkyl, C$_{2-4}$alkenyl, C$_{3-6}$cycloalkyl, C$_{3-6}$cycloalkylmethyl, C$_{2-6}$alkoxyalkyl, aryl substituted with 0-2 R$^{24}$, and heterocyclyl;

each R$^{24}$ is independently selected from hydrogen, alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, or carbonyl; and Pg is a thiol protecting group.

19. The method of claim 1, wherein the at least one chelator moiety has the structure

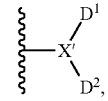

wherein X' is nitrogen and one of D$^1$ and D$^2$ is a hydrogen and the other is a chelator moiety.

20. The method of claim 19 wherein one of D$^1$ and D$^2$ is hydrogen and the other is selected from the group consisting of:

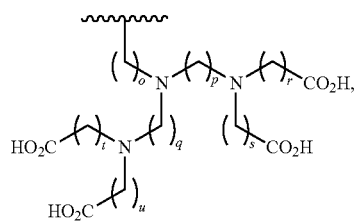

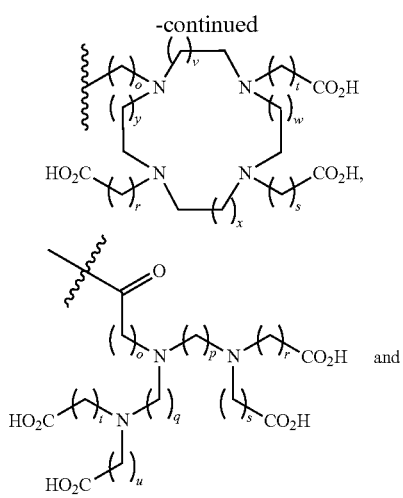
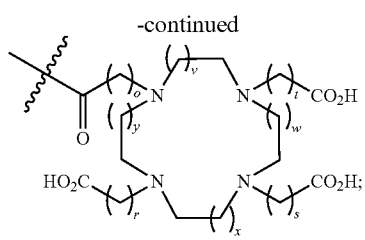
wherein:
o, p, q, r, s, t, and u are each independently 1-6; and v, w, x, and y are each independently 1-3; or
wherein o, r, s, t, and u are each 1; and p and q are each 2; or
wherein o, r, s, t, v, w, x and y are each 1.
21. The method of claim 1, wherein the chelated imaging agent has a structure selected from the group consisting of:
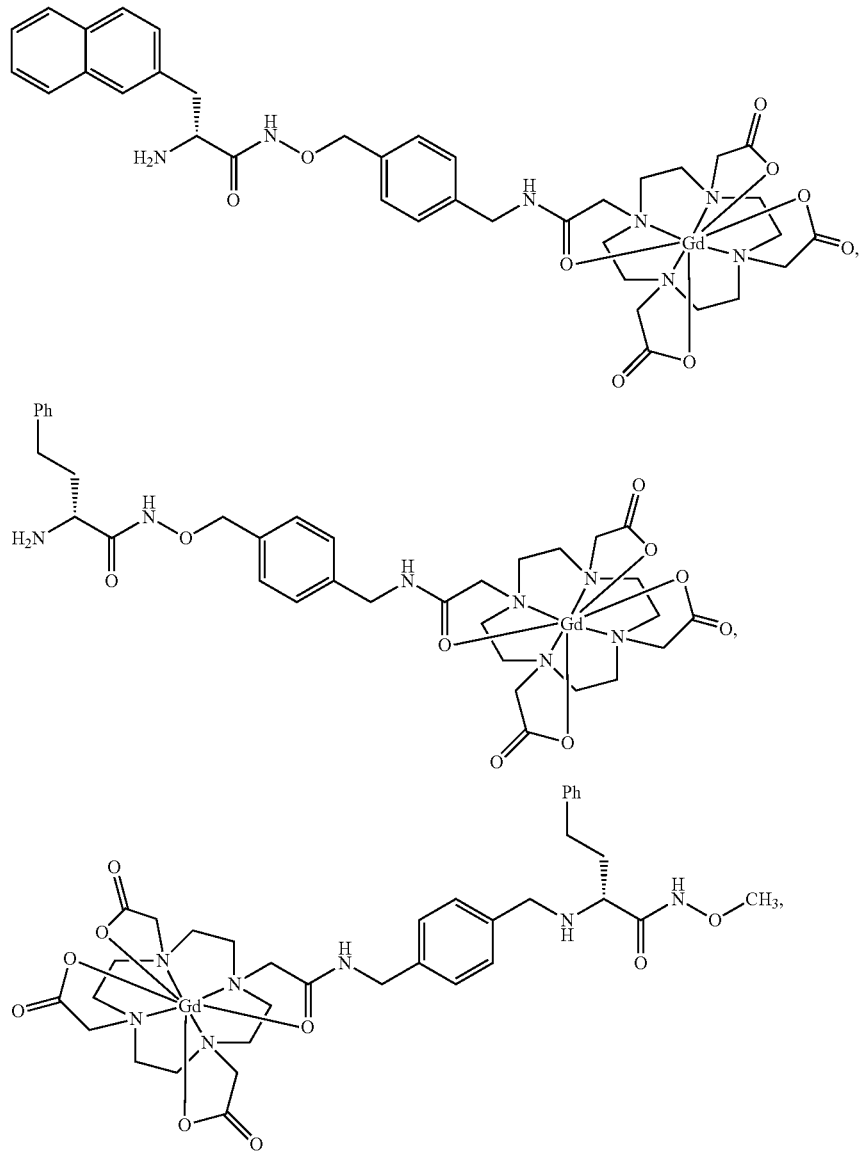

-continued
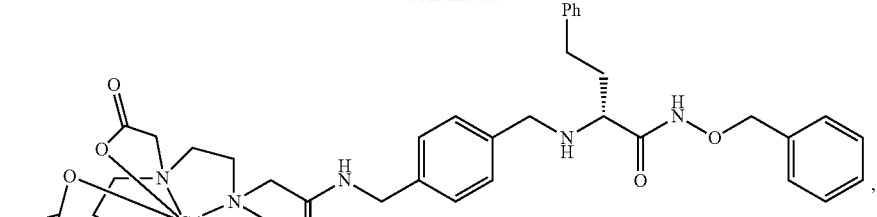
,
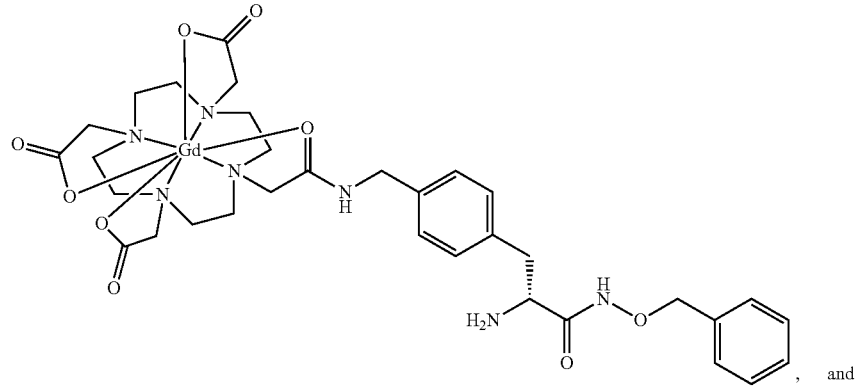
, and
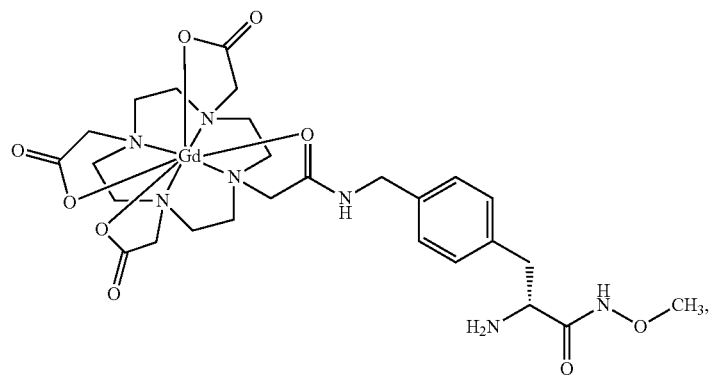
and pharmaceutically acceptable salts thereof.
* * * * *

UNITED STATES PATENT AND TRADEMARK OFFICE
CERTIFICATE OF CORRECTION

PATENT NO. : 8,852,553 B2
APPLICATION NO. : 13/723333
DATED : October 7, 2014
INVENTOR(S) : Richard R. Cesati et al.

Page 1 of 1

It is certified that error appears in the above-identified patent and that said Letters Patent is hereby corrected as shown below:

On the title page under item (*), please amend the Notice as shown below:

This patent is subject to a terminal disclaimer.

Signed and Sealed this
Twenty-sixth Day of April, 2016

Michelle K. Lee
*Director of the United States Patent and Trademark Office*